US007947261B2

(12) United States Patent
Harris et al.

(10) Patent No.: US 7,947,261 B2
(45) Date of Patent: *May 24, 2011

(54) CONJUGATES FORMED FROM POLYMER DERIVATIVES HAVING PARTICULAR ATOM ARRANGEMENTS

(75) Inventors: J. Milton Harris, Huntsville, AL (US); Antoni Kozlowski, Huntsville, AL (US); Samuel P. McManus, Huntsville, AL (US); Michael D. Bentley, Huntsville, AL (US); Stephen A. Charles, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 1402 days.

This patent is subject to a terminal disclaimer.

(21) Appl. No.: 11/389,431

(22) Filed: Mar. 23, 2006

(65) Prior Publication Data
US 2006/0275252 A1    Dec. 7, 2006

Related U.S. Application Data

(63) Continuation-in-part of application No. 10/851,691, filed on May 21, 2004.

(60) Provisional application No. 60/473,213, filed on May 23, 2003.

(51) Int. Cl.
*A61K 31/74* (2006.01)
*A61K 45/00* (2006.01)
*A61K 38/21* (2006.01)

(52) U.S. Cl. .............. 424/78.27; 424/85.1; 424/85.5; 424/85.7

(58) Field of Classification Search .............. 424/78.27, 424/85.1, 85.5, 85.6, 85.7
See application file for complete search history.

(56) References Cited

U.S. PATENT DOCUMENTS

| 3,856,830 A | 12/1974 | Kuehn |
| 3,954,584 A | 5/1976 | Miyata et al. |
| 4,179,337 A | 12/1979 | Davis et al. |
| 4,180,491 A | 12/1979 | Kim et al. |
| 5,468,365 A | 11/1995 | Menchen et al. |
| 5,643,575 A | 7/1997 | Martinez et al. |
| 5,650,234 A | 7/1997 | Dolence et al. |
| 5,919,455 A | 7/1999 | Greenwald et al. |
| 5,932,462 A | 8/1999 | Harris et al. |
| 6,048,720 A * | 4/2000 | Dalborg et al. ............ 435/219 |
| 6,113,906 A | 9/2000 | Greenwald et al. |

(Continued)

FOREIGN PATENT DOCUMENTS

CA   2 436 623   8/2002

(Continued)

OTHER PUBLICATIONS

Holtsberg et al. (Polyethylene glycol (PEG) conjugated arginine deiminase: effects of PEG formulations on its pharmnacological properties in Journal of Controlled Release, 80 (20020, 259-271).*

(Continued)

*Primary Examiner* — Blessing M Fubara
(74) *Attorney, Agent, or Firm* — Mark A. Wilson

(57) ABSTRACT

Polymeric reagents are provided comprising a moiety of atoms arranged in a specific order, wherein the moiety is positioned between a water-soluble polymer and a reactive group. The polymeric reagents are useful for, among other things, forming polymer-active agent conjugates. Related methods, compositions, preparations, and so forth are also provided.

18 Claims, 5 Drawing Sheets

1. mPEG2ButyrALD40K-rhGH; 2. mPEG2NHS40K-rhGH;
3. mPEGButyrALD30K-rhGH; 4. mPEGSMB30K-rhGH;
5. rhGH stock; 6. Sigma MW Marker

U.S. PATENT DOCUMENTS

| | | | |
|---|---|---|---|
| 6,348,558 | B1 | 2/2002 | Harris et al. |
| 6,376,604 | B2 | 4/2002 | Kozlowski |
| 6,566,506 | B2 | 5/2003 | Greenwald et al. |
| 6,624,246 | B2 | 9/2003 | Kozlowski |
| 2002/0052443 | A1 | 5/2002 | Greenwald et al. |
| 2003/0114647 | A1 | 6/2003 | Harris et al. |
| 2004/0002104 | A1 | 1/2004 | Fischer et al. |
| 2004/0115165 | A1 | 6/2004 | Rosen et al. |
| 2004/0147687 | A1 | 7/2004 | Rosen et al. |
| 2005/0003448 | A1 | 1/2005 | Zhao et al. |

FOREIGN PATENT DOCUMENTS

| | | | |
|---|---|---|---|
| CA | 2436623 | * | 8/2002 |
| DE | 101 14 134 | | 11/2002 |
| DE | 10114134 | | 11/2002 |
| EP | 0 761 780 | | 3/1997 |
| EP | 0 779 894 | | 6/2003 |
| WO | 96/17626 | | 6/1996 |
| WO | 00/75105 | | 12/2000 |
| WO | 01/05873 | | 1/2001 |
| WO | 01/23420 | | 4/2001 |
| WO | 01/93914 | | 12/2001 |
| WO | 03/049699 | | 6/2003 |
| WO | 2004/044224 | | 5/2004 |
| WO | 2004/108070 | | 12/2004 |
| WO | WO 2005000360 | | 1/2005 |

OTHER PUBLICATIONS

Gillies et al., "Designing Macromolecules for Therapeutic Applications: Polyester Dendrimer-Poly(ethylene oxide) "Bow-Tie" Hybrids with Tunable Molecular Weight and Architecture", J. Am. Chem. Soc., 2002; pp. 14137-14146, vol. 124.

Monfardini et al., "A Branched Monomethoxypoly(ethylene glycol) for Protein Modification", Bioconjugate Chemistry, 1995; pp. 62-69, vol. 6, No. 1.

Zalipsky et al., "Evaluation of a New Reagent for Covalent Attachment of Polyethylene Glycol to Proteins", Biotech and Applied Biochem., 1992; pp. 100-114, vol. 15.

Zhoa et al., "Novel Degradable Poly(ethylene glycol) Hydrogels for Controlled Release of Protein", J. of Pharmaceutical Sci., 1998; pp. 1450-1458, vol. 87, No. 11.

Enzon Pharmaceuticals, Macromolecular Engineering Technologies, pp. 1-14, (2004).

NEKTAR™—Transforming Therapeutics, Nektar Molecule Engineering: Polyethylene Glycol and Derivatives for Advanced PEGylation, pp. 1-20, (Catalog—2003).

NEKTAR™—Transforming Therapeutics, Nektar Advanced PEGylation: Polyethylene Glycol and Derivatives for Advanced PEGylation, pp. 1-24, (Catalog—2004).

NOF Corporation, "PEG Derivatives, Phospholipid and Drug Delivery Materials for Pharmaceuticals", pp. 1-46, (Catalogue 2003-1$^{st}$).

NOF Corporation, "PEG Derivatives, Phospholipid and Drug Delivery Materials for Pharmaceuticals", pp. 1-50, (Catalogue 2003-2$^{nd}$).

NOF Corporation, "PEG Derivatives, Phospholipids and Drug Delivery Materials for Pharmaceutical Products and Formulations", pp. 1-59, (Catalogue Ver. 8—Apr. 2006).

Polypure, Products; PEG amines; PEG acids and amino acids; PEG thiols and disulfides; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEG™, pp. 1-38, (Mar. 12, 2004).

Quanta Biodesign, Labeling, Modification and Crosslinking Reagents incorporating our unique monodispersed dPEG™ Technology, pp. 1-31, (Nov. 5, 2004).

Quanta Biodesign, Ltd., Leading innovator, producer and provider of monodisperse discrete PEG™ (dPEG™) derivatives, (Product Catalog), pp. 1-51, (Updated: Jul. 18, 2005).

Quanta Biodesign, Ltd., Leading innovator, producer and provider of monodisperse discrete PEG™ dPEG™) derivatives, (Product Catalog), pp. 1-51, (Updated: Nov. 17, 2005).

Shearwater Polymers, Inc., p. 2-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—2000).

Shearwater Corporation, Polyethylene Glycol and Derivatives for Biomedical Applications, pp. 1-17, (Catalog—2001).

Zalipsky, et al., "Long circulating, cationic liposomes containing amino-PEG-phosphatidylethanolamine", FEBS Letters, vol. 353, pp. 71-74, (1994).

Australian Examiner's First Report corresponding to Australian Patent Application No. 2004251602 dated Aug. 18, 2008.

Chinese First Office Action corresponding to Chinese Patent Application No. 200480004064.3 date of notification Apr. 27, 2007.

Chinese Second Office Action corresponding to Chinese Patent Application No. 200480004064.3 date of notification Feb. 1, 2008.

Chinese Rejection Decision corresponding to Chinese Patent Application No. 200480004064.3 date of notification Aug. 14, 2009.

Eurasian Official Letter corresponding to Eurasia Patent Application No. 200501863 dated Feb. 20, 2007.

Eurasian Official Letter corresponding to Eurasia Patent Application No. 200501863 dated Aug. 9, 2007.

Eurasian Official Letter corresponding to Eurasia Patent Application No. 200501863 dated May 6, 2008.

Indian First Examination Report corresponding to Indian Patent Application No. 3171/DELNP/2005 dated Aug. 4, 2008.

Japanese Notice of Reasons for Rejection corresponding to Japanese Patent Application No. 2006-533335 mailing date Oct. 13, 2009.

Mexican Office Action corresponding to Mexican Patent Application No. PA/a/2005/007628 dated Sep. 2, 2009.

New Zealand Examination Report corresponding to New Zealand Patent Application No. 541374 dated Jun. 11, 2007.

PCT Invitation to Pay Additional Fees Partial International Search corresponding to PCT Application No. PCT/US2004/016212 date of mailing Jan. 10, 2005.

PCT International Search Report corresponding to PCT Application No. PCT/US2004/016212 date of mailing Apr. 26, 2005.

PCT International Preliminary Report on Patentability corresponding to PCT/US2004/016212 date of issuance of report Nov. 25, 2005.

Heylin, "Chemistry Grads Post Gains in 2005", C & EN Washington, pp. 43-52, Jul. 2006.

U.S. Office Action Summary corresponding to U.S. Appl. No. 10/851,691 mail date Mar. 29, 2010.

Dorwald, "Side Reaction In Organic Synthesis. A Guide To Successful Synthesis Design", Weinheim, Wiley-VCH Verlag GmbH & Co. KGaA, Preface, (2005).

Jordan, "Tamoxifen: A Most Unlikely Pioneering Medicine", Nat. Rev., vol. 2, pp. 205-213, (Mar. 2003).

* cited by examiner 1. mPEG2ButyrALD40K-rhGH; 2. mPEG2NHS40K-rhGH;
3. mPEGButyrALD30K-rhGH; 4. mPEGSMB30K-rhGH;
5. rhGH stock; 6. Sigma MW Marker

SEQUENCE LISTING

```
<160> NUMBER OF SEQ ID NOS: 226

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)
<223> OTHER INFORMATION: His, Arg or Tyr
<220> FEATURE:
<221> NAME/KEY: MOD_RES
<222> LOCATION: (2)
<223> OTHER INFORMATION: Ser, Gly, Ala or Thr
<220> FEATURE:
<221> NAME/KEY: MOD_RES
<222> LOCATION: (3)
<223> OTHER INFORMATION: Asp or Glu
<220> FEATURE:
<221> NAME/KEY: MOD_RES
<222> LOCATION: (6)
<223> OTHER INFORMATION: Phe, Tyr or naphthylalanine
<220> FEATURE:
```

-continued

```
<221> NAME/KEY: MOD_RES
<222> LOCATION: (7)
<223> OTHER INFORMATION: Thr or Ser
<220> FEATURE:
<221> NAME/KEY: MOD_RES
<222> LOCATION: (8)
<223> OTHER INFORMATION: Ser or Thr
<220> FEATURE:
<221> NAME/KEY: MOD_RES
<222> LOCATION: (9)
<223> OTHER INFORMATION: Asp or Glu
<220> FEATURE:
<221> NAME/KEY: MOD_RES
<222> LOCATION: (10)
<223> OTHER INFORMATION: Leu, Ile, Val, pentylglycine or Met
<220> FEATURE:
<221> NAME/KEY: MOD_RES
<222> LOCATION: (14)
<223> OTHER INFORMATION: Leu, Ile, pentylglycine, Val or Met
<220> FEATURE:
<221> NAME/KEY: MOD_RES
<222> LOCATION: (22)
<223> OTHER INFORMATION: Phe, Tyr or naphthylalanine
<220> FEATURE:
<221> NAME/KEY: MOD_RES
<222> LOCATION: (23)
<223> OTHER INFORMATION: Ile, Val, Leu, pentylglycine, tert-butylglycine
      or Met
<220> FEATURE:
<221> NAME/KEY: MOD_RES
<222> LOCATION: (24)
<223> OTHER INFORMATION: Glu or Asp
<220> FEATURE:
<221> NAME/KEY: MOD_RES
<222> LOCATION: (25)
<223> OTHER INFORMATION: Trp, Phe, Tyr or naphtylalanine
<220> FEATURE:
<221> NAME/KEY: MOD_RES
<222> LOCATION: (31)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: MOD_RES
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: MOD_RES
<222> LOCATION: (39)
<223> OTHER INFORMATION: Ser, Thr or Tyr
<220> FEATURE:
<223> OTHER INFORMATION: may be c-term amidated

<400> SEQUENCE: 1

Xaa Xaa Xaa Gly Thr Xaa Xaa Xaa Xaa Xaa Ser Lys Gln Xaa Glu Glu
 1               5                  10                  15

Glu Ala Val Arg Leu Xaa Xaa Xaa Xaa Leu Lys Asn Gly Gly Xaa Ser
             20                  25                  30

Ser Gly Ala Xaa Xaa Xaa Xaa
            35

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
             20                  25                  30
```

```
<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 3

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Val Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 5
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 5

His Ser Asp Ala Val Phe Thr Glu Asn Tyr Thr Lys Leu Arg Lys Gln
1                5                  10                  15

Asn Ile Glu Ala Ala Lys Lys Tyr Leu Asn Asp Leu Lys Lys Gly Gly
            20                  25                  30

Thr

<210> SEQ ID NO 6
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 6

His Ser Asp Ala Val Phe Thr Glu Asn Tyr Thr Lys Leu Arg Lys Gln
 1               5                  10                  15

Leu Ala Ala Lys Lys Tyr Leu Asn Asp Leu Lys Lys Gly Gly Thr
            20                  25                  30

<210> SEQ ID NO 7
<211> LENGTH: 31
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (10)
<223> OTHER INFORMATION: CH30-Tyr
<220> FEATURE:
<223> OTHER INFORMATION: c-term amidated

<400> SEQUENCE: 9

His Ser Asp Ala Val Phe Thr Glu Asn Tyr Thr Lys Leu Arg Lys Gln
1               5                   10                  15

Asn Ile Glu Ala Ala Lys Lys Tyr Leu Asn Asp Leu Lys Lys
            20                  25                  30

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<223> OTHER INFORMATION: c-term amidated

<400> SEQUENCE: 11

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys
            20                  25

<210> SEQ ID NO 12
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys Gly Gly Thr
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Leu Asn Gly Gly Thr
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

His Ser Asp Ala Val Phe Thr Asp Asn Tyr Thr Lys Leu Arg Lys Gln
1               5                   10                  15

Leu Ala Ala Lys Lys Tyr Leu Asn Asp Ile Leu Asn Gly Gly Thr
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gly Gly Thr
            20                  25                  30

<210> SEQ ID NO 16
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 16

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys
            20                  25

<210> SEQ ID NO 17
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

His Ser Asp Ala Val Phe Thr Asp Asn Tyr Thr Arg Leu Arg Lys Gln
1               5                   10                  15

Met Ala Val Lys Lys Tyr Leu Asn Asp Leu Lys Lys Gly Gly Thr
            20                  25                  30

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

His Ser Asp Ala Val Phe Thr Glu Asn Tyr Thr Lys Leu Arg Lys Gln
1               5                   10                  15

Leu Ala Ala Lys Lys Tyr Leu Asn Asp Leu Lys Lys Gly Gly Thr Ser
            20                  25                  30

Trp Cys Glu Pro Gly Trp Cys Arg
        35                  40

<210> SEQ ID NO 19
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

His Ser Asp Ala Val Phe Thr Asp Asn Tyr Thr Arg Leu Arg Lys Gln
1               5                   10                  15

Met Ala Ala Lys Lys Tyr Leu Asn Asp Ile Lys Lys Gly Gly Thr
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 20

His Ser Asp Ala Val Phe Thr Asp Asn Tyr Thr Arg Leu Arg Lys Gln
1               5                   10                  15

Leu Ala Val Lys Lys Tyr Leu Asn Asp Ile Lys Lys Gly Gly Thr
            20                  25                  30

<210> SEQ ID NO 21
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

His Ser Asp Ala Val Phe Thr Asp Asn Tyr Thr Arg Leu Arg Lys Gln
1               5                   10                  15

Leu Ala Ala Lys Lys Tyr Leu Asn Ser Ile Lys Lys Gly Gly Thr
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Asn Gly Gly Thr
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

His Ser Asp Ala Val Phe Thr Asp Asn Tyr Thr Arg Leu Arg Lys Gln
1               5                   10                  15

Leu Ala Val Lys Lys Tyr Leu Asn Ser Ile Lys Lys Gly Gly Thr
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Gly Gly Thr
            20                  25                  30

<210> SEQ ID NO 25
<211> LENGTH: 31
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 25

His Ser Asp Ala Val Phe Thr Asp Asn Tyr Thr Arg Leu Arg Lys Gln
1               5                   10                  15

Leu Ala Val Lys Lys Tyr Leu Asn Asp Ile Lys Asn Gly Gly Thr
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

His Ser Asp Ala Val Phe Thr Asp Asn Tyr Thr Arg Leu Arg Lys Gln
1               5                   10                  15

Leu Ala Ala Lys Lys Tyr Leu Asn Ser Ile Lys Asn Gly Gly Thr
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gly Gly
            20                  25                  30

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gly
            20                  25

<210> SEQ ID NO 29
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys
            20                  25
```

```
<210> SEQ ID NO 30
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Gln
            20                  25

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Asn Gln
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Lys Lys Arg Tyr
            20                  25                  30

<210> SEQ ID NO 33
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys
            20                  25

<210> SEQ ID NO 34
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Asn
                20                  25

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Lys
                20                  25

<210> SEQ ID NO 36
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

His Ser Asp Ala Val Phe Thr Asp Asn Tyr Thr Glu Leu Arg Lys Gln
1               5                   10                  15

Met Ala Val Lys Lys Tyr Leu Asn Ser Ile Leu Asn
                20                  25

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

His Ser Asp Ala Val Phe Thr Asp Asn Tyr Thr Arg Leu Arg Glu Gln
1               5                   10                  15

Met Ala Val Lys Lys Tyr Leu Asn Ser Ile Leu Asn
                20                  25

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
                20                  25

<210> SEQ ID NO 39
<211> LENGTH: 28
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 39

His Ser Asp Ala Val Phe Thr Asp Asn Tyr Thr Arg Leu Arg Lys Gln
1               5                   10                  15

Met Ala Ala Lys Lys Tyr Leu Asn Ser Ile Leu Asn
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

His Ser Asp Ala Val Phe Thr Asp Asn Tyr Thr Arg Leu Arg Lys Gln
1               5                   10                  15

Met Ala Val Lys Lys Tyr Leu Asn Asp Ile Leu Asn
            20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn
            20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

His Ser Asp Ala Val Phe Thr Asp Asn Tyr Thr Arg Leu Arg Lys Gln
1               5                   10                  15

Met Ala Ala Lys Lys Tyr Leu Asn Ser Ile Leu Lys
            20                  25

<210> SEQ ID NO 43
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys
            20                  25
```

-continued

```
<210> SEQ ID NO 44
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Lys Arg Tyr
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Lys Arg
            20                  25                  30

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Lys Lys
            20                  25

<210> SEQ ID NO 47
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Arg Tyr
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

His Ser Asp Ala Val Phe Thr Asp Asn Tyr Thr Arg Leu Arg Lys Gln
1               5                   10                  15
```

```
Met Ala Val Lys Lys Tyr Leu Asn Ser Ile Lys Lys Lys Arg Tyr
            20                  25                  30
```

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Lys Lys Arg
            20                  25                  30
```

<210> SEQ ID NO 50
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Asp Ala Val Phe Thr Asp Asn Tyr Thr Arg Leu Arg Lys Gln Met Ala
1               5                   10                  15

Val Lys Lys Tyr Leu Asn Ser Ile Lys Lys Lys
            20                  25
```

<210> SEQ ID NO 51
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Asn Lys Arg Tyr
            20                  25                  30
```

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Lys
            20                  25
```

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 53

His Ser Asp Ala Val Phe Thr Asp Asn Tyr Thr Arg Leu Arg Lys Gln
1               5                   10                  15

Ile Ala Ala Lys Lys Tyr Leu Gln Thr Ile Lys Lys
            20                  25

<210> SEQ ID NO 54
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

His Ser Asp Gly Ile Phe Thr Glu Ser Tyr Ser Arg Tyr Arg Lys Gln
1               5                   10                  15

Met Ala Val Lys Lys Tyr Leu Ala Ala Leu Lys Lys Arg Tyr Lys
            20                  25                  30

Gln Arg Val Lys Asn Lys
        35

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 55

His Ser Asp Ala Val Phe Thr Glu Asn Tyr Thr Arg Leu Arg Lys Gln
1               5                   10                  15

Met Ala Val Lys Lys Tyr Leu Asn Ser Leu Lys Lys
            20                  25

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 56

His Ser Asp Gly Ile Phe Thr Asp Ser Tyr Ser Arg Tyr Arg Lys Gln
1               5                   10                  15

Met Ala Val Lys Lys Tyr Leu Ser Ala Val Arg His Gly Gln Thr
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 57

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys Gln Gly Gly Thr
            20                  25                  30

<210> SEQ ID NO 58
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 58

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys Lys Tyr Leu Ala Ala
            20                  25                  30

Val Arg His Gly
        35

<210> SEQ ID NO 59
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ser Trp Cys Glu Pro Gly Trp Cys Arg His Ser Asp Ala Val Phe Thr
1               5                   10                  15

Glu Asn Tyr Thr Lys Leu Arg Lys Gln Leu Ala Ala Lys Lys Tyr Leu
            20                  25                  30

Asn Asp Leu Lys Lys Gly Gly Thr
        35                  40

<210> SEQ ID NO 60
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Leu Lys Gly Gly Thr
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

His Ser Asp Ala Val Phe Thr Asp Asn Tyr Thr Arg Leu Arg Lys Gln
1               5                   10                  15

Leu Ala Ala Lys Lys Tyr Leu Asn Asp Ile Leu Asn Gly Gly Thr

```
                25                  30
```

<210> SEQ ID NO 62
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
His Ser Asp Ala Val Phe Thr Asp Asn Tyr Thr Arg Leu Arg Lys Gln
1               5                  10                  15

Leu Ala Val Lys Lys Tyr Leu Asn Asp Ile Leu Lys Gly Gly Thr
            20                  25                  30
```

<210> SEQ ID NO 63
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
His Ser Asp Gly Ile Phe Thr Asp Ser Tyr Ser Arg Tyr Arg Lys Gln
1               5                  10                  15

Leu Ala Ala Lys Lys Tyr Leu Ala Asp Val Lys Lys Gly Gly Thr
            20                  25                  30
```

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
His Ser Asp Gly Ile Phe Thr Asp Ser Tyr Ser Arg Tyr Arg Lys Gln
1               5                  10                  15

Leu Ala Ala Lys Lys Tyr Leu Ala Asp Val Lys Lys
            20                  25
```

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
His Ser Asp Gly Ile Phe Thr Asp Ser Tyr Ser Arg Tyr Arg Lys Gln
1               5                  10                  15

Leu Ala Val Lys Lys Tyr Leu Ala Ala Val Lys Lys
            20                  25
```

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys Lys
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Lys
            20                  25

<210> SEQ ID NO 68
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Arg
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr
            20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

His Ser Asp Ala Val Phe Thr Asp Asn Tyr Thr Arg Leu Arg Lys Gln
1               5                   10                  15

Leu Ala Ala Lys Lys Tyr Leu Asn Thr Ile Lys Asn Lys Arg Tyr
            20                  25                  30

<210> SEQ ID NO 71
<211> LENGTH: 31
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 71

His Ser Asp Ala Val Phe Thr Asp Asn Tyr Thr Arg Leu Arg Lys Gln
1               5                   10                  15

Val Ala Ala Lys Lys Tyr Leu Asn Ser Ile Lys Asn Lys Arg Tyr
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

His Ser Asp Ala Val Phe Thr Asp Asn Tyr Thr Arg Leu Arg Lys Gln
1               5                   10                  15

Met Ala Ala Lys Lys Tyr Leu Gln Ser Ile Lys Asn Lys Arg Tyr
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

His Ser Asp Ala Val Phe Thr Asp Asn Tyr Thr Arg Leu Arg Lys Gln
1               5                   10                  15

Met Ala Ala Lys Lys Tyr Leu Asn Thr Ile Lys Asn Lys Arg Tyr
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

His Ser Asp Ala Val Phe Thr Asp Gln Tyr Thr Arg Leu Arg Lys Gln
1               5                   10                  15

Met Ala Ala Lys Lys Tyr Leu Asn Ser Ile Lys Asn Lys Arg Tyr
            20                  25                  30

<210> SEQ ID NO 75
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

His Ser Asp Ala Val Phe Thr Asp Gln Tyr Thr Arg Leu Arg Lys Gln
1               5                   10                  15

Leu Ala Ala Lys Lys Tyr Leu Asn Thr Ile Lys Asn Lys Arg Tyr
            20                  25                  30
```

```
<210> SEQ ID NO 76
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

His Ser Asp Ala Val Phe Thr Asp Asn Tyr Thr Arg Leu Arg Lys Gln
1               5                   10                  15

Met Ala Ala His Lys Tyr Leu Asn Ser Ile Lys Asn Lys Arg Tyr
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

His Ser Asp Ala Val Phe Thr Asp Asn Tyr Thr Arg Leu Arg Lys Gln
1               5                   10                  15

Met Ala Ala Lys His Tyr Leu Asn Ser Ile Lys Asn Lys Arg Tyr
            20                  25                  30

<210> SEQ ID NO 78
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

His Ser Asp Ala Val Phe Thr Asp Gln Tyr Thr Arg Leu Arg Lys Gln
1               5                   10                  15

Leu Ala Ala His Lys Tyr Leu Asn Thr Ile Lys Asn Lys Arg Tyr
            20                  25                  30

<210> SEQ ID NO 79
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

His Ser Asp Ala Val Phe Thr Asp Gln Tyr Thr Arg Leu Arg Lys Gln
1               5                   10                  15

Leu Ala Ala Lys His Tyr Leu Asn Thr Ile Lys Asn Lys Arg Tyr
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

His Ser Asp Ala Val Phe Thr Asp Asn Tyr Thr Arg Leu Arg Lys Gln
```

```
1               5                  10                  15
Val Ala Ala Lys Lys Tyr Leu Gln Ser Ile Lys Lys Arg
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

His Ser Asp Ala Val Phe Thr Asp Asn Tyr Thr Arg Leu Arg Lys Gln
1               5                  10                  15

Val Ala Ala Lys Lys Tyr Leu Asn Ser Ile Lys Lys Arg
            20                  25                  30

<210> SEQ ID NO 82
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

His Ser Asp Ala Val Phe Thr Asp Asn Tyr Thr Arg Leu Arg Lys Gln
1               5                  10                  15

Val Ala Ala Lys Lys Tyr Leu Asn Ser Ile Lys Asn Lys Arg Tyr
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

His Ser Asp Ala Val Phe Thr Asp Asn Tyr Thr Arg Leu Arg Lys Gln
1               5                  10                  15

Val Ala Val Lys Lys Tyr Leu Gln Ser Ile Lys Lys Lys Arg
            20                  25                  30

<210> SEQ ID NO 84
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

His Ser Asp Ala Val Phe Thr Asp Asn Tyr Thr Arg Leu Arg Lys Gln
1               5                  10                  15

Val Ala Val Lys Lys Tyr Leu Gln Ser Ile Lys Lys Lys
            20                  25

<210> SEQ ID NO 85
<211> LENGTH: 31
<212> TYPE: PRT
<213> ORGANISM: Artificial Sequence
<220> FEATURE:
<223> OTHER INFORMATION: Description of Artificial Sequence: Synthetic
```

```
                       polypeptide

<400> SEQUENCE: 85

His Ser Asp Ala Val Phe Thr Asp Asn Tyr Thr Arg Leu Arg Lys Gln
1               5                   10                  15

Val Ala Val Lys Lys Tyr Leu Gln Ser Ile Lys Asn Lys Arg Tyr
            20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Lys Lys Arg Tyr
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Lys Lys Arg
            20                  25                  30

<210> SEQ ID NO 88
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Lys Lys
            20                  25

<210> SEQ ID NO 89
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys
            20                  25

<210> SEQ ID NO 90
```

```
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

His Ser Asp Ala Val Phe Thr Asp Asn Tyr Thr Arg Leu Arg Lys Gln
1               5                   10                  15

Val Ala Val Lys Lys Tyr Leu Gln Ser Ile Leu Lys Lys Arg Tyr
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

His Ser Asp Ala Val Phe Thr Asp Asn Tyr Thr Arg Leu Arg Lys Gln
1               5                   10                  15

Val Ala Val Lys Lys Tyr Leu Gln Ser Ile Leu Lys Lys Arg
            20                  25                  30

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

His Ser Asp Ala Val Phe Thr Asp Asn Tyr Thr Arg Leu Arg Lys Gln
1               5                   10                  15

Val Ala Val Lys Lys Tyr Leu Gln Ser Ile Leu Lys Lys
            20                  25

<210> SEQ ID NO 93
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Asn Lys Arg Tyr
            20                  25                  30

<210> SEQ ID NO 94
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

His Ser Asp Ala Val Phe Thr Asp Asn Tyr Thr Arg Leu Arg Lys Gln
1               5                   10                  15
```

Val Ala Ala Lys Lys Tyr Leu Gln Ser Ile Leu Asn Lys Arg
            20                  25                  30

<210> SEQ ID NO 95
<211> LENGTH: 29
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

His Ser Asp Ala Val Phe Thr Asp Asn Tyr Thr Arg Leu Arg Lys Gln
1               5                   10                  15

Val Ala Ala Lys Lys Tyr Leu Gln Ser Ile Leu Asn Lys
            20                  25

<210> SEQ ID NO 96
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

His Ser Asp Ala Val Phe Thr Asp Asn Tyr Thr Arg Leu Arg Lys Gln
1               5                   10                  15

Met Ala Cys Lys Lys Tyr Leu Asn Ser Ile Lys Asn Lys Arg
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

His Ser Asp Ala Val Phe Thr Asp Asn Tyr Thr Arg Leu Arg Lys Gln
1               5                   10                  15

Met Ala Asp Lys Lys Tyr Leu Asn Ser Ile Lys Asn Lys Arg
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

His Ser Asp Ala Val Phe Thr Asp Asn Tyr Thr Arg Leu Arg Lys Gln
1               5                   10                  15

Met Ala Glu Lys Lys Tyr Leu Asn Ser Ile Lys Asn Lys Arg
            20                  25                  30

<210> SEQ ID NO 99
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 99

His Ser Asp Ala Val Phe Thr Asp Asn Tyr Thr Arg Leu Arg Lys Gln
1               5                   10                  15

Met Ala Phe Lys Lys Tyr Leu Asn Ser Ile Lys Asn Lys Arg
            20                  25                  30

<210> SEQ ID NO 100
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

His Ser Asp Ala Val Phe Thr Asp Asn Tyr Thr Arg Leu Arg Lys Gln
1               5                   10                  15

Met Ala Gly Lys Lys Tyr Leu Asn Ser Ile Lys Asn Lys Arg
            20                  25                  30

<210> SEQ ID NO 101
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

His Ser Asp Ala Val Phe Thr Asp Asn Tyr Thr Arg Leu Arg Lys Gln
1               5                   10                  15

Met Ala His Lys Lys Tyr Leu Asn Ser Ile Lys Asn Lys Arg
            20                  25                  30

<210> SEQ ID NO 102
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

His Ser Asp Ala Val Phe Thr Asp Asn Tyr Thr Arg Leu Arg Lys Gln
1               5                   10                  15

Met Ala Ile Lys Lys Tyr Leu Asn Ser Ile Lys Asn Lys Arg
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

His Ser Asp Ala Val Phe Thr Asp Asn Tyr Thr Arg Leu Arg Lys Gln
1               5                   10                  15

Met Ala Lys Lys Lys Tyr Leu Asn Ser Ile Lys Asn Lys Arg
            20                  25                  30

<210> SEQ ID NO 104
<211> LENGTH: 30
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 104

His Ser Asp Ala Val Phe Thr Asp Asn Tyr Thr Arg Leu Arg Lys Gln
1               5                   10                  15

Met Ala Leu Lys Lys Tyr Leu Asn Ser Ile Lys Asn Lys Arg
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

His Ser Asp Ala Val Phe Thr Asp Asn Tyr Thr Arg Leu Arg Lys Gln
1               5                   10                  15

Met Ala Met Lys Lys Tyr Leu Asn Ser Ile Lys Asn Lys Arg
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

His Ser Asp Ala Val Phe Thr Asp Asn Tyr Thr Arg Leu Arg Lys Gln
1               5                   10                  15

Met Ala Asn Lys Lys Tyr Leu Asn Ser Ile Lys Asn Lys Arg
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

His Ser Asp Ala Val Phe Thr Asp Asn Tyr Thr Arg Leu Arg Lys Gln
1               5                   10                  15

Met Ala Pro Lys Lys Tyr Leu Asn Ser Ile Lys Asn Lys Arg
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

His Ser Asp Ala Val Phe Thr Asp Asn Tyr Thr Arg Leu Arg Lys Gln
1               5                   10                  15

Met Ala Gln Lys Lys Tyr Leu Asn Ser Ile Lys Asn Lys Arg
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

His Ser Asp Ala Val Phe Thr Asp Asn Tyr Thr Arg Leu Arg Lys Gln
1               5                   10                  15

Met Ala Arg Lys Lys Tyr Leu Asn Ser Ile Lys Asn Lys Arg
            20                  25                  30

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

His Ser Asp Ala Val Phe Thr Asp Asn Tyr Thr Arg Leu Arg Lys Gln
1               5                   10                  15

Met Ala Ser Lys Lys Tyr Leu Asn Ser Ile Lys Asn Lys Arg
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

His Ser Asp Ala Val Phe Thr Asp Asn Tyr Thr Arg Leu Arg Lys Gln
1               5                   10                  15

Met Ala Thr Lys Lys Tyr Leu Asn Ser Ile Lys Asn Lys Arg
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

His Ser Asp Ala Val Phe Thr Asp Asn Tyr Thr Arg Leu Arg Lys Gln
1               5                   10                  15

Met Ala Val Lys Lys Tyr Leu Asn Ser Ile Lys Asn Lys Arg
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

His Ser Asp Ala Val Phe Thr Asp Asn Tyr Thr Arg Leu Arg Lys Gln
1               5                   10                  15

Met Ala Trp Lys Lys Tyr Leu Asn Ser Ile Lys Asn Lys Arg
            20                  25                  30

<210> SEQ ID NO 114
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

His Ser Asp Ala Val Phe Thr Asp Asn Tyr Thr Arg Leu Arg Lys Gln
1               5                   10                  15

Met Ala Tyr Lys Lys Tyr Leu Asn Ser Ile Lys Asn Lys Arg
            20                  25                  30

<210> SEQ ID NO 115
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

His Ser Asp Ala Val Phe Thr Asp Asn Tyr Thr Arg Leu Arg Lys Gln
1               5                   10                  15

Met Ala Ala Lys Lys Tyr Leu Asn Ser Ile Ala Asn Lys Arg
            20                  25                  30

<210> SEQ ID NO 116
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

His Ser Asp Ala Val Phe Thr Asp Asn Tyr Thr Arg Leu Arg Lys Gln
1               5                   10                  15

Met Ala Ala Lys Lys Tyr Leu Asn Ser Ile Cys Asn Lys Arg
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

His Ser Asp Ala Val Phe Thr Asp Asn Tyr Thr Arg Leu Arg Lys Gln
1               5                   10                  15

Met Ala Ala Lys Lys Tyr Leu Asn Ser Ile Asp Asn Lys Arg
            20                  25                  30

<210> SEQ ID NO 118
<211> LENGTH: 30
<212> TYPE: PRT
<213> ORGANISM: Artificial Sequence
<220> FEATURE:

-continued

```
<223> OTHER INFORMATION: Description of Artificial Sequence: Synthetic
      polypeptide

<400> SEQUENCE: 118

His Ser Asp Ala Val Phe Thr Asp Asn Tyr Thr Arg Leu Arg Lys Gln
1               5                   10                  15

Met Ala Ala Lys Lys Tyr Leu Asn Ser Ile Glu Asn Lys Arg
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

His Ser Asp Ala Val Phe Thr Asp Asn Tyr Thr Arg Leu Arg Lys Gln
1               5                   10                  15

Met Ala Ala Lys Lys Tyr Leu Asn Ser Ile Phe Asn Lys Arg
            20                  25                  30

<210> SEQ ID NO 120
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

His Ser Asp Ala Val Phe Thr Asp Asn Tyr Thr Arg Leu Arg Lys Gln
1               5                   10                  15

Met Ala Ala Lys Lys Tyr Leu Asn Ser Ile Gly Asn Lys Arg
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

His Ser Asp Ala Val Phe Thr Asp Asn Tyr Thr Arg Leu Arg Lys Gln
1               5                   10                  15

Met Ala Ala Lys Lys Tyr Leu Asn Ser Ile His Asn Lys Arg
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

His Ser Asp Ala Val Phe Thr Asp Asn Tyr Thr Arg Leu Arg Lys Gln
1               5                   10                  15

Met Ala Ala Lys Lys Tyr Leu Asn Ser Ile Ile Asn Lys Arg
            20                  25                  30
```

```
<210> SEQ ID NO 123
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

His Ser Asp Ala Val Phe Thr Asp Asn Tyr Thr Arg Leu Arg Lys Gln
1               5                   10                  15

Met Ala Ala Lys Lys Tyr Leu Asn Ser Ile Met Asn Lys Arg
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

His Ser Asp Ala Val Phe Thr Asp Asn Tyr Thr Arg Leu Arg Lys Gln
1               5                   10                  15

Met Ala Ala Lys Lys Tyr Leu Asn Ser Ile Asn Asn Lys Arg
            20                  25                  30

<210> SEQ ID NO 125
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

His Ser Asp Ala Val Phe Thr Asp Asn Tyr Thr Arg Leu Arg Lys Gln
1               5                   10                  15

Met Ala Ala Lys Lys Tyr Leu Asn Ser Ile Pro Asn Lys Arg
            20                  25                  30

<210> SEQ ID NO 126
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

His Ser Asp Ala Val Phe Thr Asp Asn Tyr Thr Arg Leu Arg Lys Gln
1               5                   10                  15

Met Ala Ala Lys Lys Tyr Leu Asn Ser Ile Gln Asn Lys Arg
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

His Ser Asp Ala Val Phe Thr Asp Asn Tyr Thr Arg Leu Arg Lys Gln
1               5                   10                  15
```

```
Met Ala Ala Lys Lys Tyr Leu Asn Ser Ile Arg Asn Lys Arg
            20                  25                  30

<210> SEQ ID NO 128
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

His Ser Asp Ala Val Phe Thr Asp Asn Tyr Thr Arg Leu Arg Lys Gln
1               5                   10                  15

Met Ala Ala Lys Lys Tyr Leu Asn Ser Ile Ser Asn Lys Arg
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

His Ser Asp Ala Val Phe Thr Asp Asn Tyr Thr Arg Leu Arg Lys Gln
1               5                   10                  15

Met Ala Ala Lys Lys Tyr Leu Asn Ser Ile Thr Asn Lys Arg
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

His Ser Asp Ala Val Phe Thr Asp Asn Tyr Thr Arg Leu Arg Lys Gln
1               5                   10                  15

Met Ala Ala Lys Lys Tyr Leu Asn Ser Ile Val Asn Lys Arg
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

His Ser Asp Ala Val Phe Thr Asp Asn Tyr Thr Arg Leu Arg Lys Gln
1               5                   10                  15

Met Ala Ala Lys Lys Tyr Leu Asn Ser Ile Trp Asn Lys Arg
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 132

His Ser Asp Ala Val Phe Thr Asp Asn Tyr Thr Arg Leu Arg Lys Gln
1               5                   10                  15

Met Ala Ala Lys Lys Tyr Leu Asn Ser Ile Tyr Asn Lys Arg
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Ala Arg
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Cys Arg
            20                  25                  30

<210> SEQ ID NO 135
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Asp Arg
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Glu Arg
            20                  25                  30

<210> SEQ ID NO 137
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Phe Arg
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Gly Arg
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn His Arg
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Ile Arg
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Leu Arg
```

```
                    20                  25                  30

<210> SEQ ID NO 142
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Met Arg
                    20                  25                  30

<210> SEQ ID NO 143
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Asn Arg
                    20                  25                  30

<210> SEQ ID NO 144
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Pro Arg
                    20                  25                  30

<210> SEQ ID NO 145
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Gln Arg
                    20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146
```

```
His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Arg Arg
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Ser Arg
            20                  25                  30

<210> SEQ ID NO 148
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Thr Arg
            20                  25                  30

<210> SEQ ID NO 149
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Val Arg
            20                  25                  30

<210> SEQ ID NO 150
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Trp Arg
            20                  25                  30

<210> SEQ ID NO 151
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 151

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Tyr Arg
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Ala
            20                  25                  30

<210> SEQ ID NO 153
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Asp
            20                  25                  30

<210> SEQ ID NO 154
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Glu
            20                  25                  30

<210> SEQ ID NO 155
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Phe
            20                  25                  30
```

-continued

```
<210> SEQ ID NO 156
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Gly
            20                  25                  30

<210> SEQ ID NO 157
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys His
            20                  25                  30

<210> SEQ ID NO 158
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Ile
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Lys
            20                  25                  30

<210> SEQ ID NO 160
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

His Ser Asp Ala Val Phe Thr Asp Asn Tyr Thr Arg Leu Arg Lys Gln
```

```
                 1               5                  10                 15
Met Ala Ala Lys Lys Tyr Leu Asn Ser Ile Lys Asn Lys Leu
                20                 25                 30

<210> SEQ ID NO 161
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Met
                20                  25                  30

<210> SEQ ID NO 162
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Asn
                20                  25                  30

<210> SEQ ID NO 163
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Pro
                20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Gln
                20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Description of Artificial Sequence: Synthetic
```

-continued

```
      polypeptide

<400> SEQUENCE: 165

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Ser
            20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Thr
            20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Val
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Trp
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

His Ser Asp Ala Val Phe Thr Asp Asn Tyr Thr Arg Leu Arg Lys Gln
1               5                   10                  15

Met Ala Ala Lys Lys Tyr Leu Asn Ser Ile Lys Asn Lys Tyr
            20                  25                  30

<210> SEQ ID NO 170
```

```
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

His Ser Asp Ala Val Phe Thr Asp Asn Tyr Thr Arg Leu Arg Lys Gln
1               5                   10                  15

Val Ala Ala Lys Lys Tyr Leu Gln Ser Ile Lys Asn Lys Arg Tyr Ser
            20                  25                  30

Trp Cys Glu Pro Gly Trp Cys Arg
        35                  40

<210> SEQ ID NO 171
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

His Ser Asp Ala Val Phe Thr Asp Asp Tyr Thr Arg Leu Arg Lys Glu
1               5                   10                  15

Val Ala Ala Lys Lys Tyr Leu Glu Ser Ile Lys Asp Lys Arg Tyr
            20                  25                  30

<210> SEQ ID NO 172
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 172

Glu Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 173
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 173

His Lys Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 174
<211> LENGTH: 27
<212> TYPE: PRT
<213> ORGANISM: Artificial Sequence
<220> FEATURE:
<223> OTHER INFORMATION: Description of Artificial Sequence: Synthetic
```

-continued polypeptide
<220> FEATURE:
<223> OTHER INFORMATION: c-term amidated

<400> SEQUENCE: 174

His Ser Lys Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 175
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 175

His Ser Asp Lys Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 176
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 176

His Ser Asp Gly Lys Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 177
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 177

His Ser Asp Gly Ile Lys Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 178
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

```
<400> SEQUENCE: 178

His Ser Asp Gly Ile Phe Lys Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 179
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 179

His Ser Asp Gly Ile Phe Thr Lys Ser Tyr Ser Arg Tyr Arg Lys Gln
1               5                   10                  15

Met Ala Val Lys Lys Tyr Leu Ala Ala Val Leu
            20                  25

<210> SEQ ID NO 180
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 180

His Ser Asp Gly Ile Phe Thr Asp Lys Tyr Ser Arg Tyr Arg Lys Gln
1               5                   10                  15

Met Ala Val Lys Lys Tyr Leu Ala Ala Val Leu
            20                  25

<210> SEQ ID NO 181
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 181

His Ser Asp Gly Ile Phe Thr Asp Ser Lys Ser Arg Tyr Arg Lys Gln
1               5                   10                  15

Met Ala Val Lys Lys Tyr Leu Ala Ala Val Leu
            20                  25

<210> SEQ ID NO 182
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 182

His Ser Asp Gly Ile Phe Thr Asp Ser Tyr Lys Arg Tyr Arg Lys Gln
1               5                   10                  15
```

Met Ala Val Lys Lys Tyr Leu Ala Ala Val Leu
            20                  25

<210> SEQ ID NO 183
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 183

His Ser Asp Gly Ile Phe Thr Asp Ser Tyr Ser Glu Tyr Arg Lys Gln
1               5                   10                  15

Met Ala Val Lys Lys Tyr Leu Ala Ala Val Leu
            20                  25

<210> SEQ ID NO 184
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 184

His Ser Asp Gly Ile Phe Thr Asp Ser Tyr Ser Arg Lys Arg Lys Gln
1               5                   10                  15

Met Ala Val Lys Lys Tyr Leu Ala Ala Val Leu
            20                  25

<210> SEQ ID NO 185
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 185

His Ser Asp Gly Ile Phe Thr Asp Ser Tyr Ser Arg Tyr Glu Lys Gln
1               5                   10                  15

Met Ala Val Lys Lys Tyr Leu Ala Ala Val Leu
            20                  25

<210> SEQ ID NO 186
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 186

His Ser Asp Gly Ile Phe Thr Asp Ser Tyr Ser Arg Tyr Arg Glu Gln
1               5                   10                  15

Met Ala Val Lys Lys Tyr Leu Ala Ala Val Leu
            20                  25

<210> SEQ ID NO 187
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 187

His Ser Asp Gly Ile Phe Thr Asp Ser Tyr Ser Arg Tyr Arg Lys Lys
1               5                   10                  15

Met Ala Val Lys Lys Tyr Leu Ala Ala Val Leu
            20                  25

<210> SEQ ID NO 188
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 188

His Ser Asp Gly Ile Phe Thr Asp Ser Tyr Ser Arg Tyr Arg Lys Gln
1               5                   10                  15

Lys Ala Val Lys Lys Tyr Leu Ala Ala Val Leu
            20                  25

<210> SEQ ID NO 189
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 189

His Ser Asp Gly Ile Phe Thr Asp Ser Tyr Ser Arg Tyr Arg Lys Gln
1               5                   10                  15

Met Lys Val Lys Lys Tyr Leu Ala Ala Val Leu
            20                  25

<210> SEQ ID NO 190
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 190

His Ser Asp Gly Ile Phe Thr Asp Ser Tyr Ser Arg Tyr Arg Lys Gln
1               5                   10                  15

Met Ala Lys Lys Lys Tyr Leu Ala Ala Val Leu
            20                  25

<210> SEQ ID NO 191
<211> LENGTH: 27
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 191

His Ser Asp Gly Ile Phe Thr Asp Ser Tyr Ser Arg Tyr Arg Lys Gln
1               5                   10                  15

Met Ala Val Glu Lys Tyr Leu Ala Ala Val Leu
            20                  25

<210> SEQ ID NO 192
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 192

His Ser Asp Gly Ile Phe Thr Asp Ser Tyr Ser Arg Tyr Arg Lys Gln
1               5                   10                  15

Met Ala Val Lys Glu Tyr Leu Ala Ala Val Leu
            20                  25

<210> SEQ ID NO 193
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 193

His Ser Asp Gly Ile Phe Thr Asp Ser Tyr Ser Arg Tyr Arg Lys Gln
1               5                   10                  15

Met Ala Val Lys Lys Lys Leu Ala Ala Val Leu
            20                  25

<210> SEQ ID NO 194
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 194

His Ser Asp Gly Ile Phe Thr Asp Ser Tyr Ser Arg Tyr Arg Lys Gln
1               5                   10                  15

Met Ala Val Lys Lys Tyr Lys Ala Ala Val Leu
            20                  25

<210> SEQ ID NO 195
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<223> OTHER INFORMATION: c-term amidated

<400> SEQUENCE: 195

His Ser Asp Gly Ile Phe Thr Asp Ser Tyr Ser Arg Tyr Arg Lys Gln
1               5                   10                  15

Met Ala Val Lys Lys Tyr Leu Lys Ala Val Leu
            20                  25

<210> SEQ ID NO 196
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 196

His Ser Asp Gly Ile Phe Thr Asp Ser Tyr Ser Arg Tyr Arg Lys Gln
1               5                   10                  15

Met Ala Val Lys Lys Tyr Leu Ala Lys Val Leu
            20                  25

<210> SEQ ID NO 197
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 197

His Ser Asp Gly Ile Phe Thr Asp Ser Tyr Ser Arg Tyr Arg Lys Gln
1               5                   10                  15

Met Ala Val Lys Lys Tyr Leu Ala Ala Lys Leu
            20                  25

<210> SEQ ID NO 198
<211> LENGTH: 27
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 198

His Ser Asp Gly Ile Phe Thr Asp Ser Tyr Ser Arg Tyr Arg Lys Gln
1               5                   10                  15

Met Ala Val Lys Lys Tyr Leu Ala Ala Val Lys
            20                  25

<210> SEQ ID NO 199
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

His Ser Asp Ala Val Phe Thr Asp Asn Tyr Thr Arg Leu Arg Lys Gln
```

```
1               5                  10                 15
Met Ala Ala Lys Lys Tyr Leu Asn Ser Ile Lys Asn Arg Ile
         20                 25                 30

<210> SEQ ID NO 200
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

His Ser Asp Ala Val Phe Thr Asp Asn Tyr Thr Arg Leu Arg Lys Gln
1               5                  10                 15

Met Ala Gly Lys Lys Tyr Leu Asn Ser Ile Lys Asn Arg Ile
         20                 25                 30

<210> SEQ ID NO 201
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

His Ser Asp Ala Val Phe Thr Asp Asn Tyr Thr Arg Leu Arg Lys Gln
1               5                  10                 15

Met Ala Lys Lys Lys Tyr Leu Asn Ser Ile Lys Asn Arg Ile
         20                 25                 30

<210> SEQ ID NO 202
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

His Ser Asp Ala Val Phe Thr Asp Asn Tyr Thr Arg Leu Arg Lys Gln
1               5                  10                 15

Met Ala Arg Lys Lys Tyr Leu Asn Ser Ile Lys Asn Arg Ile
         20                 25                 30

<210> SEQ ID NO 203
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

His Ser Asp Ala Val Phe Thr Asp Asn Tyr Thr Arg Leu Arg Lys Gln
1               5                  10                 15

Met Ala Ser Lys Lys Tyr Leu Asn Ser Ile Lys Asn Arg Ile
         20                 25                 30

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
            polypeptide

<400> SEQUENCE: 204

His Ser Asp Ala Val Phe Thr Asp Asn Tyr Thr Arg Leu Arg Lys Gln
1               5                   10                  15

Met Ala Ala Lys Lys Tyr Leu Asn Ser Ile Pro Asn Arg Ile
            20                  25                  30

<210> SEQ ID NO 205
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

His Ser Asp Ala Val Phe Thr Asp Asn Tyr Thr Arg Leu Arg Lys Gln
1               5                   10                  15

Met Ala Gly Lys Lys Tyr Leu Asn Ser Ile Pro Asn Arg Ile
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

His Ser Asp Ala Val Phe Thr Asp Asn Tyr Thr Arg Leu Arg Lys Gln
1               5                   10                  15

Met Ala Lys Lys Lys Tyr Leu Asn Ser Ile Pro Asn Arg Ile
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

His Ser Asp Ala Val Phe Thr Asp Asn Tyr Thr Arg Leu Arg Lys Gln
1               5                   10                  15

Met Ala Arg Lys Lys Tyr Leu Asn Ser Ile Pro Asn Arg Ile
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

His Ser Asp Ala Val Phe Thr Asp Asn Tyr Thr Arg Leu Arg Lys Gln
1               5                   10                  15

Met Ala Ser Lys Lys Tyr Leu Asn Ser Ile Pro Asn Arg Ile
            20                  25                  30

<210> SEQ ID NO 209
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

His Ser Asp Ala Val Phe Thr Asp Asn Tyr Thr Arg Leu Arg Lys Gln
1               5                   10                  15

Met Ala Ala Lys Lys Tyr Leu Asn Ser Ile Gln Asn Arg Ile
            20                  25                  30

<210> SEQ ID NO 210
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

His Ser Asp Ala Val Phe Thr Asp Asn Tyr Thr Arg Leu Arg Lys Gln
1               5                   10                  15

Met Ala Gly Lys Lys Tyr Leu Asn Ser Ile Gln Asn Arg Ile
            20                  25                  30

<210> SEQ ID NO 211
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

His Ser Asp Ala Val Phe Thr Asp Asn Tyr Thr Arg Leu Arg Lys Gln
1               5                   10                  15

Met Ala Lys Lys Lys Tyr Leu Asn Ser Ile Gln Asn Arg Ile
            20                  25                  30

<210> SEQ ID NO 212
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

His Ser Asp Ala Val Phe Thr Asp Asn Tyr Thr Arg Leu Arg Lys Gln
1               5                   10                  15

Met Ala Arg Lys Lys Tyr Leu Asn Ser Ile Gln Asn Arg Ile
            20                  25                  30

<210> SEQ ID NO 213
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

His Ser Asp Ala Val Phe Thr Asp Asn Tyr Thr Arg Leu Arg Lys Gln
1               5                   10                  15
```

```
Met Ala Ser Lys Lys Tyr Leu Asn Ser Ile Gln Asn Arg Ile
            20                  25                  30
```

<210> SEQ ID NO 214
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

```
His Ser Asp Ala Val Phe Thr Asp Asn Tyr Thr Arg Leu Arg Lys Gln
1               5                   10                  15

Met Ala Ala Lys Lys Tyr Leu Asn Ser Ile Arg Asn Arg Ile
            20                  25                  30
```

<210> SEQ ID NO 215
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

```
His Ser Asp Ala Val Phe Thr Asp Asn Tyr Thr Arg Leu Arg Lys Gln
1               5                   10                  15

Met Ala Gly Lys Lys Tyr Leu Asn Ser Ile Arg Asn Arg Ile
            20                  25                  30
```

<210> SEQ ID NO 216
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
His Ser Asp Ala Val Phe Thr Asp Asn Tyr Thr Arg Leu Arg Lys Gln
1               5                   10                  15

Met Ala Lys Lys Lys Tyr Leu Asn Ser Ile Arg Asn Arg Ile
            20                  25                  30
```

<210> SEQ ID NO 217
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

```
His Ser Asp Ala Val Phe Thr Asp Asn Tyr Thr Arg Leu Arg Lys Gln
1               5                   10                  15

Met Ala Arg Lys Lys Tyr Leu Asn Ser Ile Arg Asn Arg Ile
            20                  25                  30
```

<210> SEQ ID NO 218
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

His Ser Asp Ala Val Phe Thr Asp Asn Tyr Thr Arg Leu Arg Lys Gln
1               5                   10                  15

Met Ala Ser Lys Lys Tyr Leu Asn Ser Ile Arg Asn Arg Ile
            20                  25                  30

<210> SEQ ID NO 219
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 219

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 220
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 220

Lys Lys Lys Lys Lys Lys His Gly Glu Gly Thr Phe Thr Ser Asp Leu
1               5                   10                  15

Ser Lys Gln Met Glu Glu Glu Ala Arg Leu Phe Ile Glu Trp Leu Lys
            20                  25                  30

Asn Gly Gly Pro Ser Ser Gly Ala Pro Pro Ser Lys Lys Lys Lys Lys
        35                  40                  45

Lys

<210> SEQ ID NO 221
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 221

His Gly Glu Gly Thr Phe Thr Ser Asp Leu Ser Lys Gln Met Glu Glu
1               5                   10                  15

Glu Ala Val Arg Leu Phe Ile Glu Trp Leu Trp Leu Lys Asn Gly Gly
            20                  25                  30

Pro Ser Ser Gly Ala Ser
        35

<210> SEQ ID NO 222
<211> LENGTH: 42
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 222

Lys Lys Lys Lys Lys Lys His Gly Glu Gly Thr Phe Thr Ser Asp Leu
  1               5                  10                  15

Ser Lys Gln Met Glu Glu Ala Val Arg Leu Phe Ile Glu Trp Leu
             20                  25                  30

Lys Asn Gly Gly Pro Ser Ser Gly Ala Ser
         35                  40

<210> SEQ ID NO 223
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 223

Asn Glu Glu Glu Glu Glu His Gly Glu Gly Thr Phe Thr Ser Asp Leu
  1               5                  10                  15

Ser Lys Gln Met Glu Glu Ala Val Arg Leu Phe Ile Glu Trp Leu
             20                  25                  30

Lys Asn Gly Gly Pro Ser Ser Gly Ala Ser
         35                  40

<210> SEQ ID NO 224
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 224

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
             20                  25                  30

Ser Gly Ala Ser Lys Lys Lys Lys Lys Lys
         35                  40

<210> SEQ ID NO 225
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 225

Lys Lys Lys Lys Lys Lys His Gly Glu Gly Thr Phe Thr Ser Asp Leu
  1               5                  10                  15

Ser Lys Gln Met Glu Glu Ala Val Arg Leu Phe Ile Glu Trp Leu
             20                  25                  30
```

```
Lys Asn Gly Gly Pro Ser Ser Gly Ala Ser Lys Lys Lys Lys Lys
        35              40              45

<210> SEQ ID NO 226
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: c-term amidated

<400> SEQUENCE: 226

Asp Glu Glu Glu Glu Glu His Gly Glu Gly Thr Phe Thr Ser Asp Leu
 1               5                  10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser Lys Lys Lys Lys Lys
        35              40              45
```

CONJUGATES FORMED FROM POLYMER DERIVATIVES HAVING PARTICULAR ATOM ARRANGEMENTS

CROSS REFERENCE TO RELATED APPLICATIONS

This application is a continuation-in-part of U.S. patent application Ser. No. 10/851,691, filed May 21, 2004, which claims the benefit of priority to provisional application Ser. No. 60/493,213, filed May 23, 2003, the disclosures of which are hereby incorporated herein by reference.

FIELD OF THE INVENTION

The present invention relates generally to novel polymeric reagents comprising a particular internal structural orientation, as well as to conjugates of these novel polymeric reagents. In addition, the invention relates to methods for synthesizing the polymeric reagents and methods for conjugating the polymer reagents to active agents and other substances. Moreover, the invention also relates to pharmaceutical preparations as well as to methods for administering the conjugates to patients.

BACKGROUND OF THE INVENTION

Scientists and clinicians face a number of challenges in their attempts to develop active agents into forms suited for delivery to a patient. Active agents that are polypeptides, for example, are often delivered via injection rather than the oral route. In this way, the polypeptide is introduced into the systemic circulation without exposure to the proteolytic environment of the stomach. Injection of polypeptides, however, has several drawbacks. For example, many polypeptides have a relatively short half-life, thereby necessitating repeated injections, which are often inconvenient and painful. Moreover, some polypeptides may elicit one or more immune responses with the consequence that the patient's immune system may be activated to degrade the polypeptide. Thus, delivery of active agents such as polypeptides is often problematic even when these agents are administered by injection.

Some success has been achieved in addressing the problems of delivering active agents via injection. For example, conjugating the active agent to a water-soluble polymer has resulted in polymer-active agent conjugates having reduced immunogenicity and antigenicity. In addition, these polymer-active agent conjugates often have greatly increased half-lives compared to their unconjugated counterparts as a result of decreased clearance through the kidney and/or decreased enzymatic degradation in systemic circulation. As a result of having greater half-life, the polymer-active agent conjugate requires less frequent dosing, which in turn reduces the overall number of painful injections and inconvenient visits to a health care professional. Moreover, active agents that are only marginally soluble often demonstrate a significant increase in water solubility when conjugated to a water-soluble polymer.

Due to its documented safety as well as its approval by the FDA for both topical and internal use, polyethylene glycol has been conjugated to active agents. When an active agent is conjugated to a polymer of polyethylene glycol or "PEG," the conjugated active agent is conventionally referred to as having been "PEGylated." The commercial success of PEGylated active agents such as PEGASYS® PEGylated interferon alpha-2a (Hoffmann-La Roche, Nutley, N.J.), PEG-INTRON® PEGylated interferon alpha-2b (Schering Corp., Kenilworth, N.J.), and NEULASTA™ PEG-filgrastim (Amgen Inc., Thousand Oaks, Calif.) demonstrates that administration of a conjugated form of an active agent can have significant advantages over the unconjugated counterpart. Small molecules such as distearoylphosphatidylethanolamine (Zalipsky (1993) *Bioconjug. Chem.* 4(4):296-299) and fluorouracil (Ouchi et al. (1992) *Drug Des. Discov.*9(1): 93-105) conjugated to poly(ethylene glycol) have also been prepared. Harris et al. have provided a review of the effects of PEGylation on pharmaceuticals. Harris et al. (2003) *Nat. Rev. Drug Discov.* 2(3):214-221.

Despite these successes, conjugation of a water-soluble polymer to an active agent remains challenging. One such challenge is the deactivation of the active agent upon attachment to a relatively long polyethylene glycol molecule. Although a relatively long polyethylene glycol molecule would provide the corresponding active agent-polymer conjugate with greater water solubility, conjugates bearing such long polyethylene glycol moieties have been known to be substantially inactive in vivo. It has been hypothesized that these conjugates are inactive due to the length of the relatively polyethylene glycol chain, which effectively "wraps" itself around the entire active agent, thereby blocking access to potential ligands required for activity.

The problem associated with inactive conjugates bearing a relatively large polyethylene glycol moiety has been solved, in part, by using "branched" forms of a polymer. An example of such a "branched" polymer is described in U.S. Pat. No. 5,932,462 to Harris et al. As described therein, "mPEG2-N-hydroxysuccinimide" can be attached to an accessible amino group (e.g., an amino group that is not physically blocked due to conformational structure) on a biologically active protein. This branched polymer (having a molecular weight of about 40,000 Daltons) is available from Nektar Therapeutics (Huntsville, Ala.) and has the following structure:

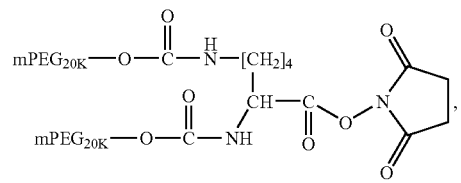

wherein mPEG$_{20K}$ represents a methoxy-end capped polyethylene glycol derivative having a molecular weight of about 20,000 Daltons.

Coupling of this branched polymer to interferon alpha-2a results in a conjugate containing an amide bond linking interferon alpha-2a to the polymer. Schematically, the conjugate can be represented as follows:

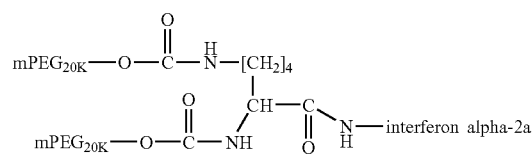

This conjugate, available commercially as PEGASYS® brand of PEGylated-interferon alpha-2a (Hoffmann-La Roche, Nutley, N.J.), is indicated for the treatment of hepatitis C in adults.

Although utilizing a branched polymer may solve some of the problems associated with relatively large linear polymers, other challenges to preparing useful conjugates persist. For example, the in vivo rate of degradation of the conjugate is often unacceptably either too long or too short. Specifically, the in vivo rate of degradation is generally (although not necessarily) partially governed by the rate of hydrolysis occurring at some point in the series of atoms that link the active agent to the polymer. Thus, a relatively quick hydrolytic rate can result in a unacceptable conjugate having too short of an in vivo half-life while relatively slow hydrolysis can result in a unacceptable conjugate having too long of an in vivo half-life. Consequently, polymers having a unique series of atoms (both in the polymer itself as well as in the corresponding conjugate) can result in unique rates of hydrolysis, which in turn influence the in vivo rate of degradation of the conjugate.

Hydrolysis of conjugates of certain active agents and mPEG2-N-hydroxysuccinimide occurs in the chain of atoms that connects one mPEG "branch" to the other, given that one of the metabolites has a molecular weight of about twenty thousand Daltons. One likely location in the chain of atoms for such a cleavage is within the

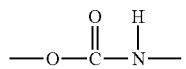

moiety located immediately adjacent to one of the MPEG portions in the polymer. The

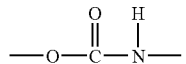

moiety represents the most likely location for cleavage because the only other atoms in the chain connecting one mPEG branch to the other are a series of carbon atoms comprised of methylene groups, which are relatively more stable to in vivo degradation than the

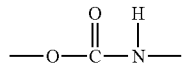

moiety. Upon cleavage, the separated form of the polymer is mPEG-OH. Thus, based at least in part on the favorability of forming mPEG-OH, a unique rate of hydrolysis results.

It would be desirable, however, to be able to provide polymers such that their hydrolysis rates could be "customized." For example, with respect to the typical weekly administration of PEGylated interferon alpha-2a, a slower rate of hydrolysis might provide for even longer periods between administrations. In addition, conjugates having too long of an in vivo half life could be improved by increasing the conjugates' susceptibility to hydrolysis.

An expanded palette of polymers having unique hydrolysis rates would enable researchers and scientists to provide active agent-polymer conjugates "customized" to provide (among other things) the desired increase in water solubility and/or rate of degradation in vivo. Moreover, polymers having unique hydrolysis rates could be used not only for branched polymers, but other forms (e.g., linear or multiarm) as well. Thus, there remains a need for polymers that provide (among other things) a unique series of atoms to provide "customized" degradation rates. To the best of applicants' knowledge, the presently described polymers, conjugates, preparations, and methods are novel and completely unsuggested by the art.

SUMMARY OF THE INVENTION

Accordingly, it is a primary object of this invention to provide a polymeric reagent comprising the following structure:

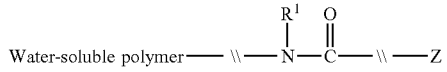

Formula (I)

wherein: the "Water-soluble polymer" is a water soluble polymer, each "-\\-" independently represents a direct covalent bond or a spacer moiety; $R^1$ is H or an organic radical; and Z is a reactive group. As depicted in Formula (I), the water-soluble polymer is proximal to the nitrogen atom of the

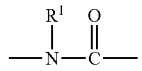

moiety and the reactive group, Z, is proximal to the carbonyl carbon atom of the

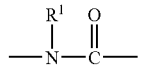

moiety. Although polymeric reagents bearing a

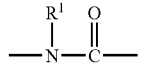

moiety are encompassed by the present invention, it is preferred to have an oxygen atom adjacent to the carbonyl carbon atom of the

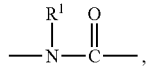

thereby resulting in a

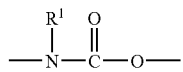

moiety, often referred to as a "carbamate" or "urethane" group. Other functional groups can also be present within or on the polymeric reagent.

It is another object of the invention to provide such a polymeric reagent wherein $R^1$ is H.

It is still another object of the invention to provide such a polymeric reagent wherein a sulfur atom is attached to the carbonyl carbon atom of the

moiety, thereby resulting in a

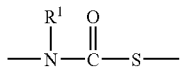

moiety.

It is still yet another object of the invention to provide such a polymeric reagent wherein a —N(R²)— moiety is attached to the carbonyl carbon atom of the

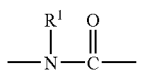

moiety, thereby providing a

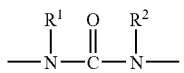

moiety wherein R² is H or an organic radical.

It is a still another object of the invention to provide a polymeric reagent wherein the water-soluble polymer is a poly(alkylene oxide).

It is a further object of the invention to provide a method for preparing the above-described polymeric reagents wherein the method comprises the steps of (i) providing a precursor molecule comprised of a protected reactive group or a precursor to a reactive group and one or more hydroxyl groups; (ii) activating at least one of the one or more hydroxyl groups of the precursor molecule for reaction with an amino group to form an activated precursor molecule; (iii) contacting under covalent coupling conditions at least one of the one or more activated hydroxyl groups with a water-soluble polymer having an amino group, thereby forming a polymer comprised of a water-soluble polymer portion and the protected reactive group or the precursor to a reactive group; and (iv) deprotecting the protected reactive group when present.

It is still a further object of the invention to provide a polymer conjugate comprising a water-soluble polymer, a

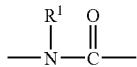

moiety, and a pharmacologically active agent, wherein: (i) the water-soluble polymer is linked to the nitrogen atom of the

moiety through either a direct covalent bond or through a first spacer moiety; (ii) the pharmacologically active agent is linked to the carbonyl carbon atom of the

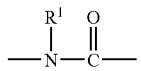

moiety through either a direct covalent bond or a second spacer moiety; and (iii) R¹ is H or an organic radical.

It is an additional object of the invention to provide a method for preparing a conjugate comprising the step of contacting a polymeric reagent as provided herein with an active agent under suitable conditions to thereby form the conjugate. Typically, the active agent covalently attaches to the polymer via reaction between a reactive group on the polymeric reagent with a functional group (e.g., an amine) on the active agent.

It is still an additional object of the invention to provide a pharmaceutical preparation comprising the active agent-polymer conjugate as provided herein in combination with a pharmaceutical excipient.

It is an additional object to provide a method for delivering a pharmacologically active agent comprising the step of administering a therapeutically effective amount of an active agent-polymer conjugate as provided herein.

Additional objects, advantages and novel features of the invention will be set forth in the description that follows, and in part, will become apparent to those skilled in the art upon the following, or may be learned by practice of the invention.

In one embodiment then, a polymeric reagent is provided comprising a

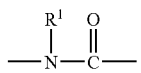

moiety positioned between a water-soluble polymer and a reactive group. The internal structural arrangement is such that (i) the nitrogen in the

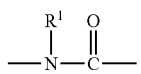

moiety is proximal to the water-soluble polymer, (ii) the carbonyl carbon atom of the

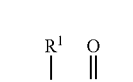

moiety is proximal to the reactive group, and (iii) R¹ is H or an organic radical, wherein the organic radical is typically selected from the group consisting of alkyl, substituted alkyl, alkenyl, substituted alkenyl, alkynyl, substituted alkynyl, aryl and substituted aryl.

The polymeric reagents of the invention also comprise a water-soluble polymer, a

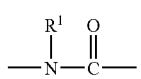

moiety, and a reactive group, wherein: (i) the water-soluble polymer is linked to the nitrogen atom of the

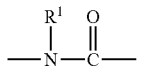

moiety through either a direct covalent bond or through a first spacer moiety; (ii) the reactive group is linked to the carbonyl carbon atom of the

moiety through either a direct covalent bond or a second spacer moiety; and (iii) $R^1$ is as previously defined.

For the polymeric reagents of the present invention, any water-soluble polymer can serve as the water-soluble polymer in the polymeric reagent and the invention is not limited in this regard. Preferred polymers, however, are end-capped on one terminus. In addition, polymers having a mass average molecular weight of less than about 120,000 Daltons are preferred.

In another embodiment, a method for preparing the polymeric reagents of the invention is provided. Briefly, the method involves providing a precursor molecule comprised of a protected reactive group or a precursor to a reactive group and one or more hydroxyl groups. At least one of the one or more hydroxyl groups of the precursor molecule is activated (thereby forming an activated precursor molecule) such that at least one of the one or more hydroxyl groups will react with an amino group. Thereafter, the activated precursor molecule is placed under covalent coupling conditions and is allowed contact a water-soluble polymer having an amino group, thereby allowing the two to react chemically. The ensuing reaction results in the formation of a covalent bond between the water-soluble polymer and the activated precursor molecule, which, in turn, forms a polymer comprised of a water-soluble polymer portion and the protected reactive group or precursor to a reactive group. Typically, this polymer can be further reacted with various reagents in order to functionalize the polymer with, for example, a desired reactive group. When the precursor molecule comprises a protected reactive group, the method advantageously includes a deprotecting step to remove the group protecting the reactive group. Optionally, a step for isolating the polymer is performed to so that the polymer can be provided in a more pure form.

In still another embodiment of the invention, a conjugate is provided comprising a water-soluble polymer, a

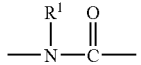

moiety, and an active agent, wherein: (i) the water-soluble polymer is linked to the nitrogen atom of the

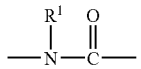

moiety through either a direct covalent bond or through a first spacer moiety; (ii) the pharmacologically active agent is linked to the carbonyl carbon of the

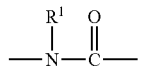

moiety through either a direct covalent bond or a second spacer moiety; and (iii) $R^1$ is H or an organic radical. Advantageously, any active agent that can be coupled to the polymeric reagents provided herein can be used and the invention is not limited with respect to the specific active agent used.

In still another embodiment of the invention, a method of preparing a conjugate is provided comprising the step of contacting a polymeric reagent as provided herein with an active agent under conditions suitable to provide a conjugate.

In still another embodiment of the invention, pharmaceutical preparations are provided comprising a conjugate of the invention in combination with a pharmaceutical excipient. The pharmaceutical preparations encompass all types of formulations and in particular those that are suited for injection, e.g., powders that can be reconstituted as well as suspensions and solutions.

In an additional embodiment of the invention, a method for administering a conjugate is provided comprising the step of administering to a patient a therapeutically effective amount of a conjugate provided herein. Typically, although not necessarily, the conjugate is provided as part of a pharmaceutical preparation. Any approach to administer the conjugate can be used and the invention is not limited in this regard. It is preferred, however, that the conjugate is administered via injection.

BRIEF DESCRIPTION OF THE FIGURES

FIG. 2A is a reproduction of a size exclusion chromatography (SEC)-HPLC chromatagram of an exemplary hGH conjugate reaction mixture prepared by reacting hGH with mPEG-2-NHS, as described in greater detail in Example 26. FIG. 2B shows the preparative profile of the reaction mixture shown in FIG. 2A following purification by anion-exchange chromatography. FIG. 2C is a reproduction of the SEC-HPLC chromatogram of a purified monoPEGylated hGH conjugate ("1-mer"), designated "mono(mPEG-2-NHS-40k) hGH", as described in greater detail in Example 26. FIG. 2D is a reproduction of the SEC-HPLC chromatogram of a purified diPEGylated conjugate ("2-mer"), designated "di(mPEG-2-NHS-40k) hGH", as described in greater detail in Example 26.

DETAILED DESCRIPTION OF THE INVENTION

Figure 1:
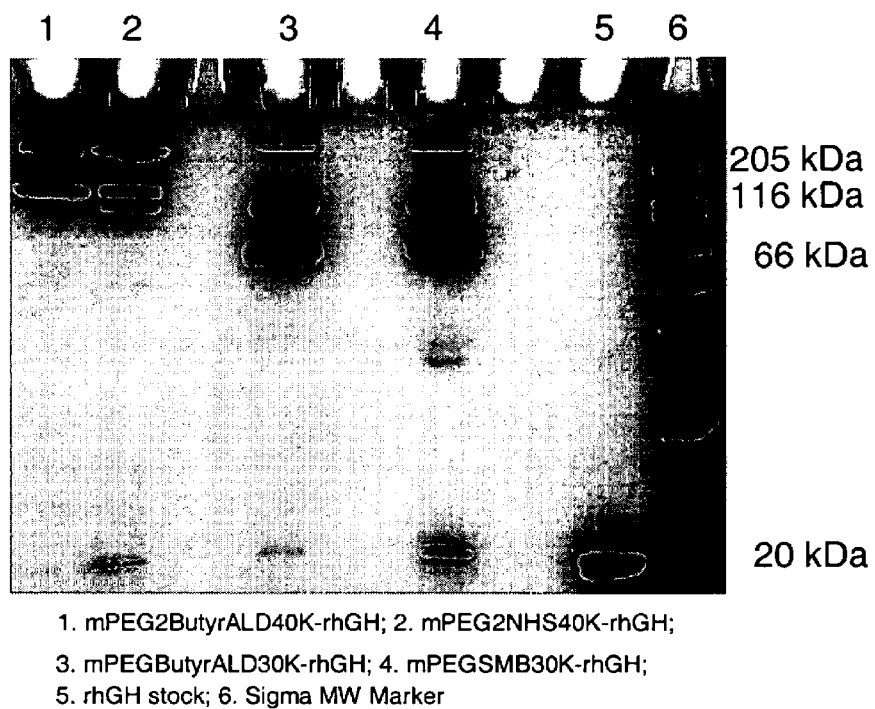
FIG. 1 is a reproduction of the SDS-PAGE analysis of various conjugates as described in Examples 1 to 4. Lane 1 corresponds to mPEG-2-ButyrALD-40 kD hGH (Example 27); Lane 2 corresponds to mPEG-2-NHS-40 kD hGH (Example 26); Lanes 3 and 4 correspond to hGH conjugates formed with reagents other than those described herein; Lane 5 corresponds to a hGH stock solution; and Lane 6 corresponds to a Sigma molecular weight marker.

Before describing the present invention in detail, it is to be understood that this invention is not limited to the particular polymers, synthetic techniques, active agents, and the like as such may vary.

It must be noted that, as used in this specification and the claims, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide) and can be used interchangeably. Typically, PEGs for use in the present invention will comprise "—(OCH$_2$CH$_2$)$_m$—" or "—O(CH$_2$CH$_2$O)$_m$—" where (m) is 2 to 4000, and the terminal groups and architecture of the overall PEG may vary. As used herein, PEG also includes "—CH$_2$—CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. "PEG" means a polymer that contains a majority, that is to say, greater than 50%, of subunits that are —CH$_2$CH$_2$O—. One commonly employed PEG is end-capped PEG. Specific PEG forms for use in the invention include PEGs having a variety of molecular weights, structures or geometries (e.g., branched, linear, forked PEGs, multifunctional, multiarmed and the like), to be described in greater detail below.

The terms "end-capped" or "terminally capped" are interchangeably used herein to refer to a terminal or endpoint of a polymer having an end-capping moiety. Typically, with respect to PEG, the end-capping moiety comprises a hydroxy or C$_{1-20}$ alkoxy group. Thus, examples of end-capping moieties include alkoxy (e.g., methoxy, ethoxy and benzyloxy), as well as aryl, heteroaryl, cyclo, heterocyclo, and the like. It should be remembered that the terminal hydroxy and alkoxy groups may include the terminal oxygen atom of a repeating ethylene oxide monomer when the structure is drawn out, depending on how the repeating ethylene oxide monomer is defined [e.g., "—(OCH$_2$CH$_2$)$_m$" or "—CH$_2$CH$_2$O (CH$_2$CH$_2$O)$_m$—CH$_2$CH$_2$—". In addition, saturated, unsaturated, substituted and unsubstituted forms of each of the foregoing end-capping moieties are envisioned. Moreover, the end-capping group can also be a silane or a lipid (e.g., a phospholipid. The end-capping group can also advantageously comprise a detectable label. When the polymer has an end-capping group comprising a detectable label, the amount or location of the polymer and/or the moiety (e.g., active agent) to which the polymer is coupled to of interest can be determined by using a suitable detector. Such labels include, without limitation, fluorescers, chemiluminescers, moieties used in enzyme labeling, calorimetric (e.g., dyes), metal ions, radioactive moieties, and the like. Suitable detectors include photometers, films, spectrometers, and the like.

"Non-naturally occurring" with respect to a polymer means a polymer that in its entirety is not found in nature. A non-naturally occurring polymer may however contain one or more subunits or segments of subunits that are naturally occurring, so long as the overall polymer structure is not found in nature.

The term "water soluble" as in a "water-soluble polymer" is a polymer that is soluble in water at room temperature. Typically, a solution of a water-soluble polymer will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

Molecular weight in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymeric reagents of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

As used herein, the term "carboxylic acid" is a moiety having a

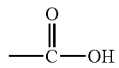

functional group [also represented as a "—COOH" or —C(O)OH], as well as moieties that are derivatives of a carboxylic acid, such derivatives including, for example, protected carboxylic acids. Thus, unless the context clearly dictates otherwise, the term carboxylic acid includes not only the acid form, but corresponding esters and protected forms as well. Exemplary protecting groups for carboxylic acids and other protecting groups are described in Greene et al., "PROTECTIVE GROUPS IN ORGANIC SYNTHESIS," Chapter 6, 3$^{rd}$ Edition, John Wiley and Sons, Inc., New York, 1999 (p. 454-493).

The term "reactive" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected," "protecting group" and "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene et al., supra.

"Activated carboxylic acid" means a functional derivative of a carboxylic acid that is more reactive than the parent carboxylic acid, in particular, with respect to nucleophilic acyl substitution. Activated carboxylic acids include but are not limited to acid halides (such as acid chlorides), anhydrides, amides and esters.

As used herein, the term "functional group" or any synonym thereof is meant to encompass protected forms thereof.

The terms "spacer" and "spacer moiety" are used herein to refer to an atom or a collection of atoms optionally used to link interconnecting moieties such as a terminus of a water-soluble polymer portion and a functional group. The spacer moiety may be hydrolytically stable or may include a physiologically hydrolyzable or enzymatically degradable linkage.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include ethyl, propyl, butyl, pentyl, 1-methylbutyl (i.e., 2-pentyl), 1-ethylpropyl (i.e., 3-pentyl), 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, iso-butyl, and tert-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, phenyl; substituted phenyl; and the like. "Substituted aryl" is aryl having one or more non-interfering groups as a substituent. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, benzyloxy, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-butynyl, isopentynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion or atom or collection of atoms, which may be ionic, having an electrophilic center, i.e., a center that is electron seeking, capable of reacting with a nucleophile.

"Nucleophile" refers to an ion or atom or collection of atoms, which may be ionic, having a nucleophilic center, i.e., a center that is seeking an electrophilic center or with an electrophile.

A "physiologically cleavable" or "hydrolyzable" or "degradable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

The terms "active agent," "biologically active agent" and "pharmacologically active agent" are used interchangeably herein and are defined to include any agent, drug, compound, composition of matter or mixture that provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" and "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a polymer-active agent conjugate—typically present in a pharmaceutical preparation—that is needed to provide a desired level of active agent and/or conjugate in the bloodstream or in the target tissue. The exact amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multifunctional" in the context of a polymer of the invention means a polymer having 3 or more functional groups contained therein, where the functional groups may be the same or different. Multifunctional polymers of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone. A "difunctional" polymer means a polymer having two functional groups contained therein, either the same (i.e., homodifunctional) or different (i.e., heterodifunctional).

"Forked," in reference to the geometry or overall structure of a polymer, refers to a difunctional polymer having one polymer "arm" (i.e., a single water-soluble polymer) wherein both functional groups are attached (either directly or through one or more atoms) to an atom serving as a branching atom, which in turn is attached (either directly or through one or more atoms) to the water-soluble polymer.

"Branched," in reference to the geometry or overall structure of a polymer, refers to polymer having 2 or more polymer "arms." A branched polymer may possess 2 polymer arms, 3 polymer arms, 4 polymer arms, 6 polymer arms, 8 polymer arms or more. One particular type of highly branched polymer is a dendritic polymer or dendrimer, which, for the purposes of the invention, is considered to possess a structure distinct from that of a branched polymer.

A "dendrimer" or dendritic polymer is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers, including branched polymers.

A basic or acidic reactant described herein includes neutral, charged, and any corresponding salt forms thereof.

The term "patient," refers to a living organism suffering from or prone to a condition that can be prevented or treated by administration of a conjugate as provided herein, and includes both humans and animals.

An "organic radical" is a carbon-containing moiety that can be attached via a covalent bond to another atom. Exemplary organic radical include those that are selected from the group consisting of alkyl, substituted alkyl, alkenyl, substituted alkenyl, alkynyl, substituted alkynyl, aryl and substituted aryl.

"Optional" or "optionally" means that the subsequently described circumstance may or may not occur, so that the description includes instances where the circumstance occurs and instances where it does not.

As used herein, the "halo" designator (e.g., fluoro, chloro, iodo, bromo, and so forth) is generally used when the halogen is attached to a molecule, while the suffix "ide" (e.g., fluoride, chloride, iodide, bromide, and so forth) is used when the ionic form is used when the halogen exists in its independent ionic form (e.g., such as when a leaving group leaves a molecule).

In the context of the present discussion, it should be recognized that the definition of a variable provided with respect to one structure or formula is applicable to the same variable repeated in a different structure, unless the context dictates otherwise. Thus, for example, the definitions of "POLY," "a spacer moiety," "(Z)," and so forth with respect to a polymeric reagent are equally applicable to a water-soluble polymer conjugate provided herein.

Turning to a first embodiment of the invention then, a unique polymeric reagent is provided. Although not wishing to be bound by theory, applicants believe the distinctive properties of the polymeric reagents described herein are attributable to the unique orientation of atoms. For example, when a polymeric reagent described herein is coupled to an active agent to form a conjugate, the conjugate's rate of hydrolysis in vivo is different than the rate of hydrolysis of a conjugate that has the same atoms, but arranged in a different sequence. In addition to providing alternative rates of hydrolysis, the polymeric reagents provided herein have additional advantages over prior art polymeric reagents.

The polymers of the invention comprise three separate components oriented in a specific manner. The three components are as follows: a water-soluble polymer comprising repeating monomer units; a moiety comprising a nitrogen atom covalently bound to the carbon atom of a carbonyl; and a reactive group. The three components of the polymer are specifically oriented such that the nitrogen atom of the aforementioned moiety is proximal to the repeating monomer portion of the polymer while the carbon atom is proximal to the reactive group. It will be understood that the term "proximal" in the present context refers to "nearest" following the closest path of linking atoms rather than nearest in terms of spatial or absolute distance.

Thus, the polymers can schematically be represented by the following formula:

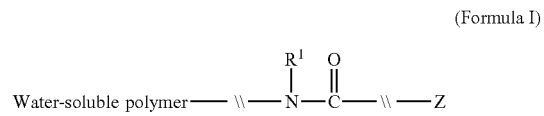

(Formula I)

wherein: the "Water-soluble polymer" is a water-soluble polymer comprising repeating monomer units; each "-\\-" independently is a direct covalent bond or a spacer moiety; R¹ is H or an organic radical; and Z is a reactive group. As depicted in Formula I, the nitrogen of the

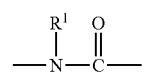

moiety is proximal to the water-soluble polymer and the carbon atom of the carbonyl is proximal to the reactive group "Z."

The polymeric reagents of the invention therefore comprise a

moiety positioned between a water-soluble polymer and a reactive group, wherein: (i) the nitrogen atom in the

moiety is proximal to the water-soluble polymer; (ii) the carbonyl carbon atom of the

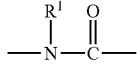

moiety is proximal to the reactive group; and (iii) $R^1$ is as defined previously. The water-soluble polymer is linked to the nitrogen atom of the

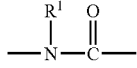

moiety through either a direct covalent bond or through a first spacer moiety. The reactive group is linked to the carbonyl carbon atom of the

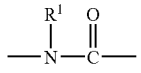

moiety through either a direct covalent bond or a second spacer moiety.

In addition, the polymeric reagents of the invention can be described as comprising a water-soluble polymer, a

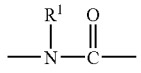

moiety, and a reactive group, wherein: (i) the water-soluble polymer is linked to the nitrogen atom of the

moiety through either a direct covalent bond or through a first spacer moiety; (ii) the reactive group is linked to the carbonyl carbon atom of the

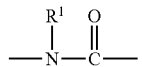

moiety through either a direct covalent bond or a second spacer moiety; and (iii) $R^1$ is as defined previously.

The

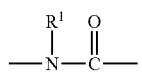

moiety (wherein $R^1$ is H or an organic radical) may be considered an amide moiety when considered in isolation and apart from adjacent atoms. It must be remembered, however, that the

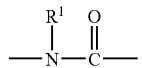

moiety in the polymer is part of a larger structure. For example, an oxygen atom can be—and preferably is—directly attached to the carbonyl carbon atom of the

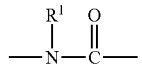

moiety, thereby providing a

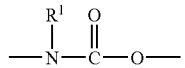

moiety that is often referred to as a "carbamate" or "urethane." Similarly, a sulfur atom can optionally be attached to the carbonyl carbon atom of the

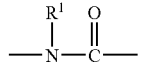

moiety, thereby providing a

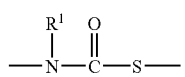

moiety. In addition, a —N($R^2$)— moiety can be attached to the carbonyl carbon of the

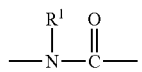

moiety, thereby providing a

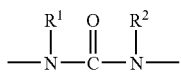

moiety wherein R² is H or an organic radical. Finally, in all instances in which reference to the

moiety is made, a

moiety can be substituted therefore and the invention is not limited to merely

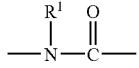

moieties.

Thus, for purposes of describing chemical structures hereinafter, reference will generally be made to a

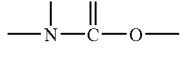

moiety. For purposes of the present description, however, each of a

moiety (wherein an oxygen atom is not attached to the carbonyl carbon atom), a

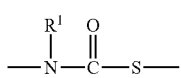

moiety, a

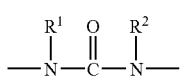

moiety, a

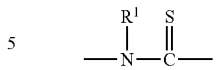

moiety, a

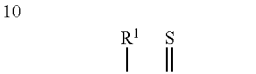

moiety, a

moiety and a

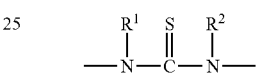

moiety, can be substituted when a

moiety is referenced.

With respect to the

moiety, one bond of the nitrogen atom attaches to the carbon atom of the adjacent carbonyl carbon (the "carbonyl carbon"), another bond attaches either directly to the water-soluble polymer or to a spacer moiety, and a third bond attaches to a substituent, "R¹." R¹ is any non-interfering substituent. R¹ is typically, although not necessarily, H or an organic radical. It is, however, preferred that R¹ is H. In those instances when R¹ is an organic radical, preferred organic radicals include those selected from the group consisting of selected from the group consisting of alkyl, substituted alkyl, alkenyl, substituted alkenyl, alkynyl, substituted alkynyl, aryl and substituted aryl. Specific examples of preferred organic radicals include those selected from the group consisting of methyl, ethyl, n-propyl, isopropyl, n-butyl, sec-butyl, isobutyl, tert-butyl, n-pentyl, isopentyl, neopentyl, tert-pentyl, and piperidonyl.

With respect to the reactive group, "Z," this group can be any group that reacts with a suitable reagent under the appropriate conditions. Preferred reactive moieties are selected from the group consisting of electrophiles and nucleophiles. Examples of such reactive groups include, but are not limited to those selected from the group consisting of hydroxyl (—OH), ester, ester, orthoester, carbonate, carbonate, acetal, aldehyde, aldehyde hydrate, ketone, vinyl ketone, ketone hydrate, thione, monothiohydrate, dithiohydrate, hemiketal, monothioketal hemiketal, dithiohemiketal, ketal, dithioketal, alkenyl, acrylate, methacrylate, acrylamide, sulfone, sulfone, amine, hydrazide, thiol, disulfide, thiol hydrate, carboxylic acid, isocyanate, isothiocyanate, maleimide

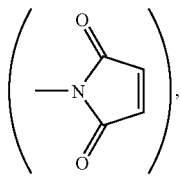

succinimide

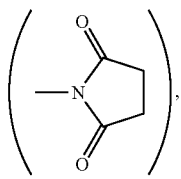

benzotriazole

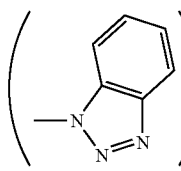

vinylsulfone, chloroethylsulfone, dithiopyridine, vinylpyridine, iodoacetamide, epoxide, glyoxals, diones, mesylates, tosylates, thiosulfonate, tresylate, silane, —$(CH_2)_rCO_2H$, —$(CH_2)_rCO_2NS$, —$(CH_2)_rCO_2Bt$, —$(CH_2)_rCH(OR)_2$, —$(CH_2)_rCHO$, —$(CH_2)_2$—$NH_2$, —$(CH_2)_rM$, —$(CH_2)_{r'}$—S—$SO_2$—R, where (r) is 1-12, (r') is 0-5, R is aryl or alkyl, NS is N-succinimidyl, Bt is 1-benzotriazolyl, and M is N-maleimidyl, and protected and activated forms of any of the foregoing.

With respect to any reactive group, and in particular maleimide and aldehyde, an optional linker can link the reactive group to the polymer. Thus, for example, the linker can link the reactive group to a spacer moiety or a branching moiety (when present). In addition, when neither a spacer moiety nor branching moiety is present, the linker can link the reactive group directly to the carbonyl carbon of the

moiety. The linker can comprise straight chain saturated acyclic hydrocarbons comprising at least four carbon atoms, such as tetramethylene, pentamethylene, and hexamethylene, as well as branched saturated acyclic hydrocarbons comprising at least four carbon atoms. In one embodiment, the hydrocarbon portion of the linkage has the structure —$(CR^3R^4)_g$—, wherein each $R^3$ is independently H, alkyl, or cycloalkyl, each $R^4$ is independently H, alkyl, or cycloalkyl, and (g) is 3 to about 20, preferably 4 to about 12. In one preferred embodiment, each $R^3$ and $R^4$ is H. In branched acyclic hydrocarbon embodiments, it is preferable for the branching to occur at one or more of the two carbon atoms closest to the reactive group (e.g., maleimide) in order to maximize steric hindrance. In another embodiment, the hydrocarbon portion of the linkage includes a saturated bivalent alicyclic hydrocarbon and has the structure —$(CR^3R^4)_p$—$C_{3-12}$cycloalkyl-$(CR^3R^4)_q$—, wherein p and q are each independently 0 to about 10, preferably 0 to about 6 (e.g., 0, 1, 2, 3, 4, 5 or 6) and $R^3$ and $R^4$ are as defined previously. The bivalent cycloalkyl (e.g., cycloalkylene) group is preferably $C_{3-8}$ cycloalkylene, such as various isomeric forms of cyclopropadiyl (e.g., 1,1-, cis-1,2-, or trans-1,2-cyclopropylene), cyclobutadiyl, cyclopentadiyl, cyclohexadiyl, and cycloheptadiyl. The cycloalkylene group can be substituted with one or more alkyl groups, preferably $C_{1-6}$ alkyl groups.

With respect to the water-soluble polymer, the polymeric reagents of the invention also comprise at least one water-soluble polymer segment. Water-soluble polymers that are nonpeptidic and water-soluble, with from 2 to about 300 termini, are particularly useful in the invention. Examples of suitable water-soluble polymers include, but are not limited to, poly(alkylene glycols), such as poly(ethylene glycol) ("PEG"), copolymers of ethylene glycol and propylene glycol having water-solubility, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384. In some applications where relatively high water solubility is desired, the water-soluble polymer is not poly(propylene oxide).

The repeating units in each of water-soluble polymer can have a number of different arrangements including, but not limited to, those selected from the group consisting of homopolymer (wherein each monomer unit comprising the water-soluble polymer is the same), alternating copolymer (wherein a first monomer unit consistently alternates with a second monomer unit within the water-soluble polymer), random copolymer (wherein a first monomer unit inconsistently alternates with a second monomer unit within the water-soluble polymer), block copolymer, (wherein two or more first monomer units alternate with two or more second monomer units within the water-soluble polymer), alternating tripolymer, random tripolymer, and block tripolymer.

The water-soluble polymer is preferably, although not necessarily, a poly(ethylene glycol) ("PEG") or a derivative thereof. It should be understood, however, that related polymers are also suited for use in the practice of this invention and that the use of the term "PEG" or "poly(ethylene glycol)" is intended to be inclusive and not exclusive in this respect. Consequently, the term "PEG" includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

In one form useful in the present invention, free or non-bound PEG is a linear polymer terminated at each end with hydroxyl groups:

(m') typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

—CH$_2$CH$_2$O—(CH$_2$CH$_2$O)$_{m'}$—CH$_2$CH$_2$— where (m') is as defined as above.

Another type of PEG useful in the present invention is methoxy-PEG-OH, or mPEG in brief, in which one terminus is the relatively inert methoxy group, while the other terminus is a hydroxyl group. The structure of mPEG is given below.

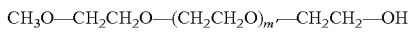
CH$_3$O—CH$_2$CH$_2$O—(CH$_2$CH$_2$O)$_{m'}$—CH$_2$CH$_2$—OH where (m') is as described above.

In addition to the above-described forms of PEG, the polymer can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

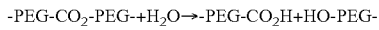
-PEG-CO$_2$-PEG-+H$_2$O→-PEG-CO$_2$H+HO-PEG-

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(l):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Although the molecular weight of the water-soluble polymer (as well as the polymeric reagent) can vary, the molecular weight will satisfy one or more of the following values: greater than 100 Daltons; greater than 200 Daltons; greater than 400 Daltons; greater than 500 Daltons, greater than 750 Daltons; greater than 900 Daltons; greater than 1,000 Daltons, greater than 1,400 Daltons; greater than 1,500 Daltons, greater than 1,900 Daltons; greater than 2,000 Daltons; greater than 2,200 Daltons; greater than 2,500 Daltons; greater than 3,000 Daltons; greater than 4,000 Daltons; greater than 4,900 Daltons; greater than 5,000 Daltons; greater than 6,000 Daltons; greater than 7,000 Daltons; greater than 7,500 Daltons, greater than 9,000 Daltons; greater than 10,000 Daltons; greater than 11,000 Daltons; greater than 14,000 Daltons; greater than 15,000 Daltons; greater than 16,000 Daltons; greater than 19,000 Daltons; greater than 20,000 Daltons; greater than 21,000 Daltons; greater than 22,000 Daltons, greater than 25,000 Daltons; and greater than 30,000 Daltons. It is understood that the maximum limit of molecular weight for any given water-soluble polymer segment useful herein is about 300,000 Daltons.

The molecular weight of the water-soluble polymer (as well as the entire polymeric reagent) can also be expressed as being a value within a range of molecular weights. Exemplary ranges include: from about 100 Daltons to about 100,000 Daltons; from about 500 Daltons to about 80,000 Daltons; from about 1,000 Daltons to about 60,000 Daltons; from about 2,000 Daltons to about 50,000 Daltons; and from about 5,000 Daltons to about 40,000 Daltons.

Exemplary molecular weights for any given water-soluble polymer (as well as the entire polymeric reagent) within a polymeric reagent include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, about 75,000 Daltons, and about 80,000 Daltons.

With respect to PEG, wherein a structure comprising a repeating ethylene oxide monomer, such as "—(CH$_2$CH$_2$O)$_m$—" or "—(OCH$_2$CH$_2$)$_m$," can be provided, preferred values for (m) include: from about 3 to about 3,000; from about 10 to about 3,000; from about 15 to about 3,000; from about 20 to about 3,000; from about 25 to about 3,000; from about 30 to about 3,000; from about 40 to about 3,000; from about 50 to about 3,000; from about 55 to about 3,000; from about 75 to about 3,000; from about 100 to about 3,000; and from about 225 to about 3,000.

As used herein, the term "water-soluble polymer" includes those water-soluble polymers that are biocompatible and nonimmunogenic and specifically excludes any water-soluble polymer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer segments described herein as well as conjugates are biocompatible and nonimmunogenic.

Those of ordinary skill in the art will recognize that the foregoing discussion concerning substantially water-soluble polymer is by no means exhaustive and is merely illustrative, and that all polymeric materials having the qualities described above are contemplated. As used herein, the term "polymeric reagent" generally refers to an entire molecule, which can comprise a water-soluble polymer and a functional group. The term "water-soluble polymer" is generally reserved for use in discussing one portion of a larger molecular structure such as a polymeric reagent, precursor molecule, conjugate, and so forth.

Each portion (e.g., functional group, active agent, water-soluble polymer, and so forth) of the polymeric reagent and other structures described herein can be directly attached to each other via a direct covalent bond. More typically, however, each portion is attached through a spacer moiety comprised of one or more atoms serving to tether each portion together into a unified whole.

Preferred spacer moieties through which the various portions of the polymeric reagents and other structures described herein include a chain of atoms made of carbon, nitrogen, oxygen, and/or sulfur atoms. Attached to this chain of atoms, can be one or more other atoms such as carbon, nitrogen, oxygen, sulfur, and hydrogen. The chain can be short and comprise as few as a chain of two to five atoms. Longer chains, for example, a chain of atoms of ten, fifteen, or more in length are also contemplated. In addition, the spacer moiety can comprise a ring of atoms that can be saturated, unsaturated, as well as being aromatic. When present, a spacer moiety preferably comprises a sequence of about 1-20 atoms excluding any branching atoms. Preferably, the atoms making up the spacer moiety (including any branching atoms) comprise some combination of oxygen, carbon, nitrogen, sulfur and hydrogen atoms. Each spacer moiety (e.g., first spacer moiety, second spacer moiety, third spacer moiety, and so forth) in the polymeric reagent can be the same as or different from any other spacer moiety present in the polymer.

Nonlimiting examples of a spacer moiety are those selected from the group consisting of —O—, —S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—CH$_2$—, —CH$_2$—CH$_2$—NH—C(O)—CH$_2$—CH$_2$—NH—C(O)—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, —CH$_2$—, —O—C(O)—CH$_2$—CH$_2$—CH$_2$—, —CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^2$)—, —CH$_2$—CH$_2$—CH$_2$—C(O)—NH—CH$_2$—CH$_2$—NH—C(O)—CH$_2$—CH$_2$—, O—C(O)—NH—[CH$_2$]$_f$—(OCH$_2$CH$_2$)$_n$—, and combinations of two or more of any of the foregoing, wherein (f) is 0 to 6, (n) is 0 to 20 (preferably 0 to 10, e.g., 0, 1, 2, 3, 4, 5, 6, 7, 8, 9 or 10, and more preferably 4), R$^2$ is H or an organic radical. Preferred bivalent cycloalkyl groups have the structure —(CR$^3$R$^4$)$_p$—C$_{3-12}$cycloalkyl-(CR$^3$R$^4$)$_q$—, wherein p and q are each independently 0 to about 10, preferably 0 to about 6 (e.g., 0, 1, 2, 3, 4, 5 or 6), each R$^3$ is independently H, alkyl, or another cycloalkyl, and each R$^4$ is independently H, alkyl, or another cycloalkyl. Other bivalent cycloalkyl (e.g., cycloalkylene) groups include C$_{3-8}$ cycloalkyl, such as various isomers of cyclopropadiyl (e.g., 1,1-, cis- 11,2-, or trans-1,2-cyclopropylene), cyclobutadiyl, cyclopentadiyl, cyclohexadiyl, and cycloheptadiyl. The cycloalkylene group can be substituted with one or more alkyl groups, preferably C$_1$-C$_6$ alkyl groups.

For any given spacer moiety that comprises both a carbonyl and a carbon atom adjacent thereto, the spacer moiety optionally includes an organic radical attached to the carbon atom adjacent to the carbonyl. Conventionally, the carbon atom immediately adjacent to the carbonyl carbon is called the alpha carbon. Thus, an alpha carbon in any given spacer moiety can have an organic radical such as a small alkyl group (e.g., methyl group) attached thereto.

The overall structure of the polymeric reagent can take any number of different forms. For example, the polymeric reagent can be linear, branched, multi-armed, dendritic, or forked. Linear structures according to the present invention correspond to Formulae II and IIa below. It is preferred, however, that the polymeric reagent has either a branched or multiarmed structure. Generally speaking, such polymers possess two or more water-soluble polymers and create a larger, more dense polymer "cloud" surrounding an active agent, thereby reducing the effective number of attachment sites available coupling. Formulae III, IIIa, IIIb, and IIIb$_1$ below branched structures comprising two water-soluble polymers. Branched structures may also comprise three water-soluble polymers. Multiarmed polymers, on the other hand, comprise four or more such water-soluble polymers. Dendritic forms of the polymers have several (e.g., 3 to 50) separate water-soluble polymers ultimately connected to a core comprising one or more atoms. For any particular polymeric reagent that comprises two or more water-soluble polymers, each water-soluble polymer can be the same or different. Moreover, combinations of the same and different water-soluble polymers can be used when the polymeric reagent comprises three or more water-soluble polymers, although it is preferred that each water-soluble polymer in the polymer is the same as the other(s).

With respect to branched forms of the polymeric reagent, exemplary ranges of suitable sizes for the total molecular weight of the polymer (as based essentially on the combined weights of the two water-soluble polymer portions) include the following (again, expressed in terms of molecular mass): from about 200 Daltons to about 200,000 Daltons; from about 1,000 Daltons to about 100,000 Daltons; from about 2,000 Daltons to about 120,000 Daltons; from about 4,000 Daltons to about 100,000 Daltons; from about 5,000 Dalton to about 90,000 Daltons from about 10,000 Daltons to about 80,000 Daltons, and from about 15,000 Daltons to about 60,000 Daltons. More particularly, total molecular mass (in Daltons) of a branched version of the polymer of the invention corresponds to one of the following: about 400; about 1,000; about 1,500; about 2,000; about 3000; about 4,000; about 10,000;

about 15,000; about 20,000; about 30,000; about 40,000; about 50,000; about 60,000; about 80,000, about 90,000, about 100,000, about 120,000, about 160,000, or about 200,000.

In considering the general structure of the polymeric reagents described herein, one will recognize certain differences with respect to polymeric reagents described in the prior art. For example, many of the prior art polymeric reagents suffer from a number of problems that make them unsuited for coupling to an active agent. For example, some prior art polymer reagents lack a readily displaceable functional group, such as a reactive group (e.g., ester). Even if one were to attempt to couple a polymeric reagent lacking a readily displaceable functional group (e.g., a methylene ($-CH_2-$) group), the conditions required to do so would be very harsh (e.g., strongly alkaline conditions), thereby likely degrading the active agent. Furthermore, some prior art polymeric reagents have two groups (e.g., carbonyl groups) substituted on the potential site of attachment, which often leads to incomplete conjugation due to steric effects and/or reduced reactivity as a consequence of the proximity of the groups.

When only a single water-soluble polymer is present in the overall structure of the polymer, the structure of the polymer preferably corresponds to Formula (II):

$$POLY^1-(X^1)_a-\underset{R^1}{\underset{|}{N}}-\underset{O}{\underset{\|}{C}}-O-(X^2)_b-Z$$ (Formula II)

wherein:
POLY$^1$ is a water-soluble polymer (e.g., PEG or MPEG);
(a) is 0, 1, 2 or 3 (and preferably 0 or 1);
(b) is 0, 1, 2 or 3 (and preferably 0 or 1);
R$^1$ is H or an organic radical (e.g., selected from the group consisting of alkyl, substituted alkyl, alkenyl, substituted alkenyl, alkynyl, substituted alkynyl, aryl and substituted aryl);
X$^1$, when present, is a first spacer moiety;
X$^2$, when present, is a second spacer moiety; and
Z is a reactive group.

Moreover, when the polymer comprises only a single water-soluble portion in the overall structure, the structure can also correspond to Formula IIa:

$$Z-(X^4)_d-O-\underset{O}{\underset{\|}{C}}-\underset{R^1}{\underset{|}{N}}-(X^3)_c-POLY^1-(X^1)_a-\underset{R^1}{\underset{|}{N}}-\underset{O}{\underset{\|}{C}}-O-(X^2)_b-Z$$ (Formula IIa)

wherein:
POLY$^1$ is a water-soluble polymer (e.g., PEG or mPEG);
(a) is 0, 1, 2 or 3 (and preferably 0 or 1);
(b) is 0, 1, 2 or 3 (and preferably 0 or 1);
(c) is 0, 1, 2 or 3 (and preferably 0 or 1);
(d) is 0, 1, 2 or 3 (and preferably 0 or 1);
Each R$^1$ is independently H or an organic radical (e.g., selected from the group consisting of alkyl, substituted alkyl, alkenyl, substituted alkenyl, alkynyl, substituted alkynyl, aryl and substituted aryl;
X$^1$, when present, is a first spacer moiety;
X$^2$, when present, is a second spacer moiety;
X$^3$, when present, is a third spacer moiety;
X$^4$, when present, is a fourth spacer moiety; and
each Z is independently a reactive group.

In addition, when two water-soluble polymers are present in the overall structure of the polymeric reagent, the structure can correspond to Formula III:

$$\begin{array}{c}POLY^1-(X^1)_a-\underset{R^1}{\underset{|}{N}}-\underset{O}{\underset{\|}{C}}-O-(X^2)_b\\ \phantom{POLY^1-(X^1)_a-}\phantom{XXXXXXXXXX}R^5-(X^7)_{g'}-(CH_2CH_2O)_j-(X^8)_h-Z\\ POLY^2-(X^5)_e-\underset{R^1}{\underset{|}{N}}-\underset{O}{\underset{\|}{C}}-O-(X^6)_{f'}\end{array}$$ (Formula III)

wherein:
POLY$^1$ is a water-soluble polymer (e.g., PEG or MPEG);
POLY is a water-soluble polymer (e.g., PEG or MPEG);
(a) is 0, 1, 2 or 3 (and preferably 0 or 1);
(b) is 0, 1, 2 or 3 (and preferably 0 or 1);
(e) is 0, 1, 2 or 3 (and preferably 0 or 1);
(f') is 0, 1, 2 or 3 (and preferably 0 or 1);
(g') is 0, 1, 2 or 3 (and preferably 0 or 1);
(h) is 0, 1, 2 or 3 (and preferably 0 or 1);
(j) is 0 to 20 (i.e., 0, 1, 2, 3, 4, 5, 6, 7, 8, 9, 10, 11, 12, 13, 14, 15, 16, 17, 18, 19 or 20);
Each R$^1$ is independently H or an organic radical (e.g., selected from the group consisting of alkyl, substituted alkyl, alkenyl, substituted alkenyl, alkynyl, substituted alkynyl, aryl and substituted aryl;
X$^1$, when present, is a first spacer moiety;
X$^2$, when present, is a second spacer moiety;
X$^5$, when present, is a fifth spacer moiety;
X$^6$, when present, is a sixth spacer moiety;
X$^7$, when present, is a seventh spacer moiety;
X$^8$, when present, is an eighth spacer moiety;
R$^5$ is a branching moiety; and
Z is a reactive group.

Preferred polymeric reagents having structures encompassed by Formulae II, (IIa), and III are those wherein each water-soluble polymer (i.e., POLY$^1$ and/or POLY$^2$) is a poly (alkyene oxide) such as poly(ethylene oxide). Preferably, although not necessarily, the poly(ethylene oxide) will be end-capped at one terminus with a group such as methyl, benzyl or hydroxyl. A particularly preferred end-capped poly (ethylene oxide) is one that corresponds to one of the following structures: $H_3C-(OCH_2CH_2)_m-$ or $H_3C-(OCH_2CH_2)_m-O-C(O)-NH-[CH_2]_f-(OCH_2CH_2)_n-$, wherein (m) is 2 to 4000, (f) is 0 to 6, (n) is 0 to 20.

Each spacer moiety (whether it is a first spacer moiety, second spacer moiety or third spacer moiety) appearing in a polymer and encompassed by Formulas II, IIa or III is independently defined as above with respect to spacer moieties generally. It is preferred, however, that each spacer moieties such as those designated as "X$^1$" and "X$^5$" is selected from the group consisting of $-O-$, $-O-CH_2-$, $-O-CH_2-CH_2-$, $-O-C(O)-NH-CH_2-CH_2-$, and $-O-C(O)-NH-CH_2-CH_2-(OCH_2CH_2)_2-$. With respect to spacer moieties designated as "X$^2$" and "X$^6$", the spacer moiety is preferably selected from the group consisting of $-CH_2-$, $-CH_2-CH_2-$, $-CH_2-CH_2(OR^2)-$, $-CH_2-CH(OR^2)-CH(OR^2)-$, $-N(R^2)-$, and R$^2$ is H or an organic radical selected from the group consisting of alkyl, substituted alkyl, alkenyl, substituted alkenyl, alkynyl, substituted alkynyl, aryl and substituted aryl. With respect to a spacer moiety designated at "X$^8$," the spacer moiety is preferably selected from the group consisting of $-O-$, $-O-CH_2-$, $-O-CH_2-CH_2-$, $-O-CH_2-CH_2-CH_2-$, $-O-CH_2-CH_2-CH_2-C(O)-$, $-CH_2-$, —CH$_2$—CH$_2$—, —CH$_2$—CH$_2$—CH$_2$—, —CH$_2$—CH$_2$—CH$_2$—C(O)—, —CH$_2$—CH$_2$—CH$_2$—C(O)—NH—CH$_2$—CH$_2$—NH—C(O)—CH$_2$—CH$_2$—, and —CH$_2$—CH$_2$—CH$_2$—C(O)—NH—(CH$_2$CH$_2$O)$_n$—CH$_2$—CH$_2$—CH$_2$—, wherein (n) is 0 to 20. Optionally, X$^8$ can include a further branching point or several branching points wherein additional reactive groups can be present, thereby providing a "forked" arrangement. Other "forked" arrangements that can be used in the present polymers are described more fully in International Application No. PCT/US99/05333.

The branching moiety R$^5$ in Formula III can be any branching moiety that can provide coupling to at least three atoms. Preferably, however, R$^5$ is selected from the group consisting of saturated alkyl, substituted saturated alkyl,

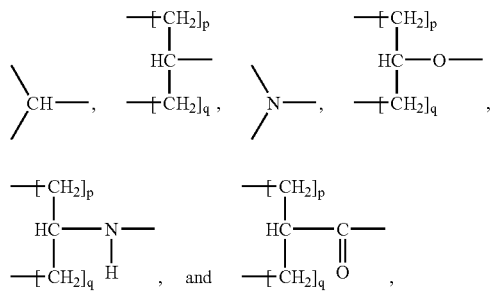

wherein (p) is 1-10(e.g., 1, 2, 3, 4, 5, 6, 7, 8, 9 or 10) and (q) is 1-10(e.g., 1, 2, 3, 4, 5, 6, 7, 8, 9 or 10).

Although the reactive group "Z" as shown in Formulae II, IIa and III can be any reactive group described above, it is preferred that the reactive group is selected from the group consisting of carboxylic acid, aldehyde, sulfone, ester, succinimide, and maleimide. Illustrative examples of a spacer moiety (e.g., X$^2$, X$^4$ and X$^8$) and Z combinations include

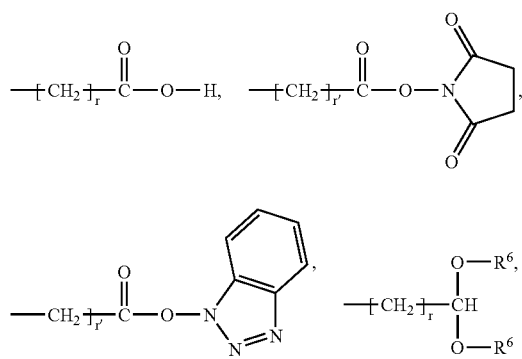

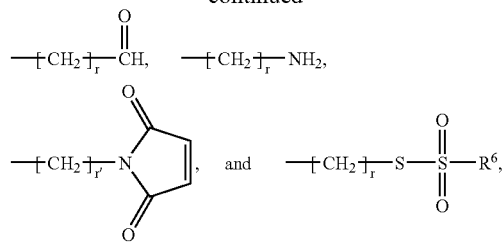

wherein (r) is 1-12 (e.g., 1, 2, 3, 4, 5, 6, 7, 8, 9, 10, 11 or 12), (r') is 0-5 (e.g., 0, 1, 2, 3, 4 or 5), and R$^6$ is aryl or alkyl.

As will be appreciated by one of ordinary skill in the art, the present invention encompasses a large number of polymers. Nonlimiting examples of polymers according to the present invention are provided below.

For example, starting with Formula III and defining and R$^5$ as

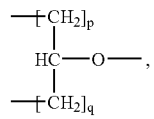

wherein each of (p) and (q) is one, and each of (b) and (f') as zero, results in a polymer having a structure corresponding to Formula (IIIa), below.

(Formula IIIa)

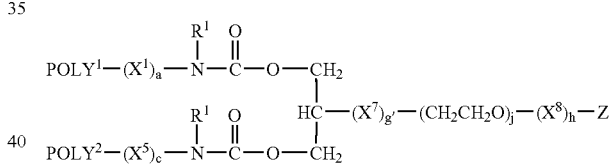

wherein POLY$^1$, POLY$^2$, (a), (c), (g'), (j), (h), R$^1$, X$^7$, X$^8$, and Z are as previously defined.

Formula IIIa can, in turn, be further defined to provide a polymeric reagent having a structure corresponding to Formula IIIb. Specifically, starting from Formula IIIa and defining each R$^1$ as H, each of POLY$^1$ and POLY$^2$ as H$_3$C—(OCH$_2$CH$_2$)$_m$— wherein (m) is 2 to 4000, each of (a) and (e) as one, each of X$^1$ and X$^5$ as —O—C(O)—NH—[CH$_2$]$_f$—(OCH$_2$CH$_2$)$_n$— where (f) is 0 to 6 and (n) is 0 to 20, results in a polymeric reagent having a structure corresponding to Formula IIIb:

(Formula IIIb)

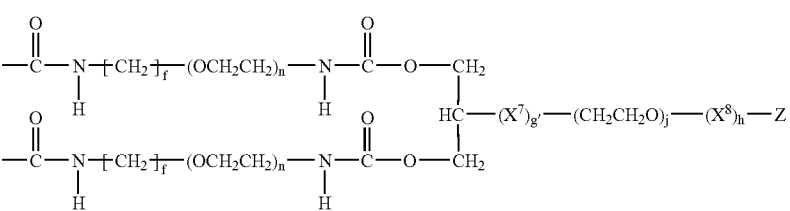

wherein each (m) is 2 to 4000, each (f) is independently 0 to 6, and each (n) is independently 0 to 20, and (g'), (h), (j), $X^7$, $X^8$ and Z are as previously defined.

Formula IIIb can, in turn, be further defined to provide a polymeric reagent having a structure corresponding to Formula IIIc. Specifically, starting from Formula IIIb and defining each of (g') and (j) as zero, (h) as one, $X^8$ as —$CH_2$—$CH_2$—$CH_2$—, and Z as a carboxylic acid results in a polymer having a structure corresponding to Formula IIIc, below.

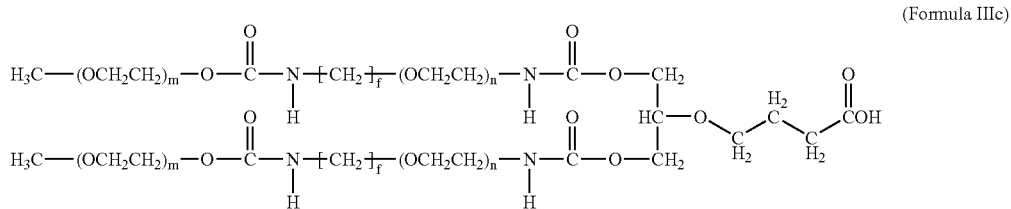
(Formula IIIc)

wherein each (m) is 2 to 4000, each (f) is independently 0 to 6, and each (n) is independently 0 to 20 (e.g., 0, 1, 2, 3, 4, 5, 6, 7, 8, 9, 10, 11, 12, 13, 14, 15, 16, 17, 18, 19 or 20).

Optionally, Formula IIIc can also include an alkyl group connected to either the alpha or beta carbon of the carboxylic acid. With respect to the alkyl group (e.g., methyl) on the alpha carbon of the carboxylic acid of the, the structure corresponds to Formula $IIIb_1$.

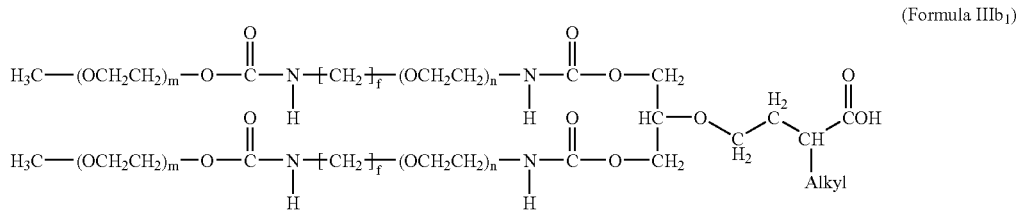
(Formula $IIIb_1$)

In addition, Formula IIIa can be further defined to provide another preferred polymer. Specifically, starting from Formula IIIa and defining each of $POLY^1$ and $POLY^2$ as $H_3C$—$(OCH_2CH_2)_m$— wherein (m) is 2 to 4000, each of (a), (c), (g'), and (j) as zero, (h) as one, $X^8$ as —$CH_2$—$CH_2$—$CH_2$—C(O)—NH—$CH_2$—$CH_2$—NH—C(O)—$CH_2$—$CH_2$—, and Z as

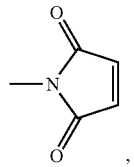

results in a polymer having the following structure:

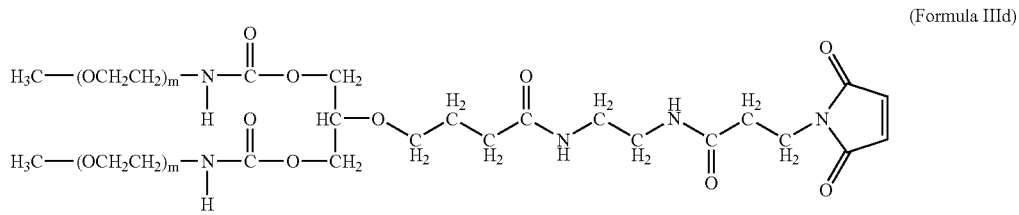
(Formula IIId)

wherein each (m) is 2 to 4000.

Additional polymeric reagents of the invention are as follows:
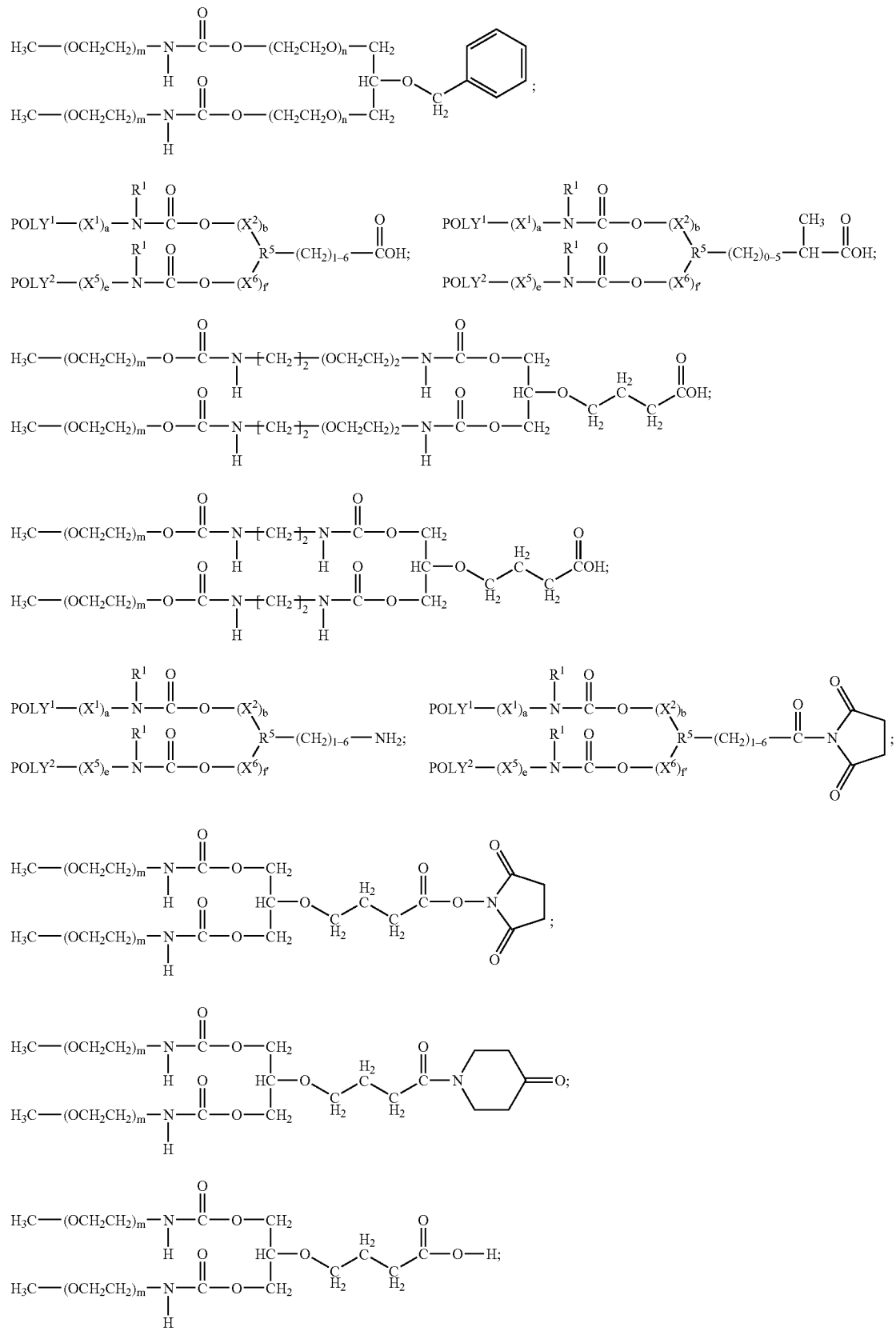

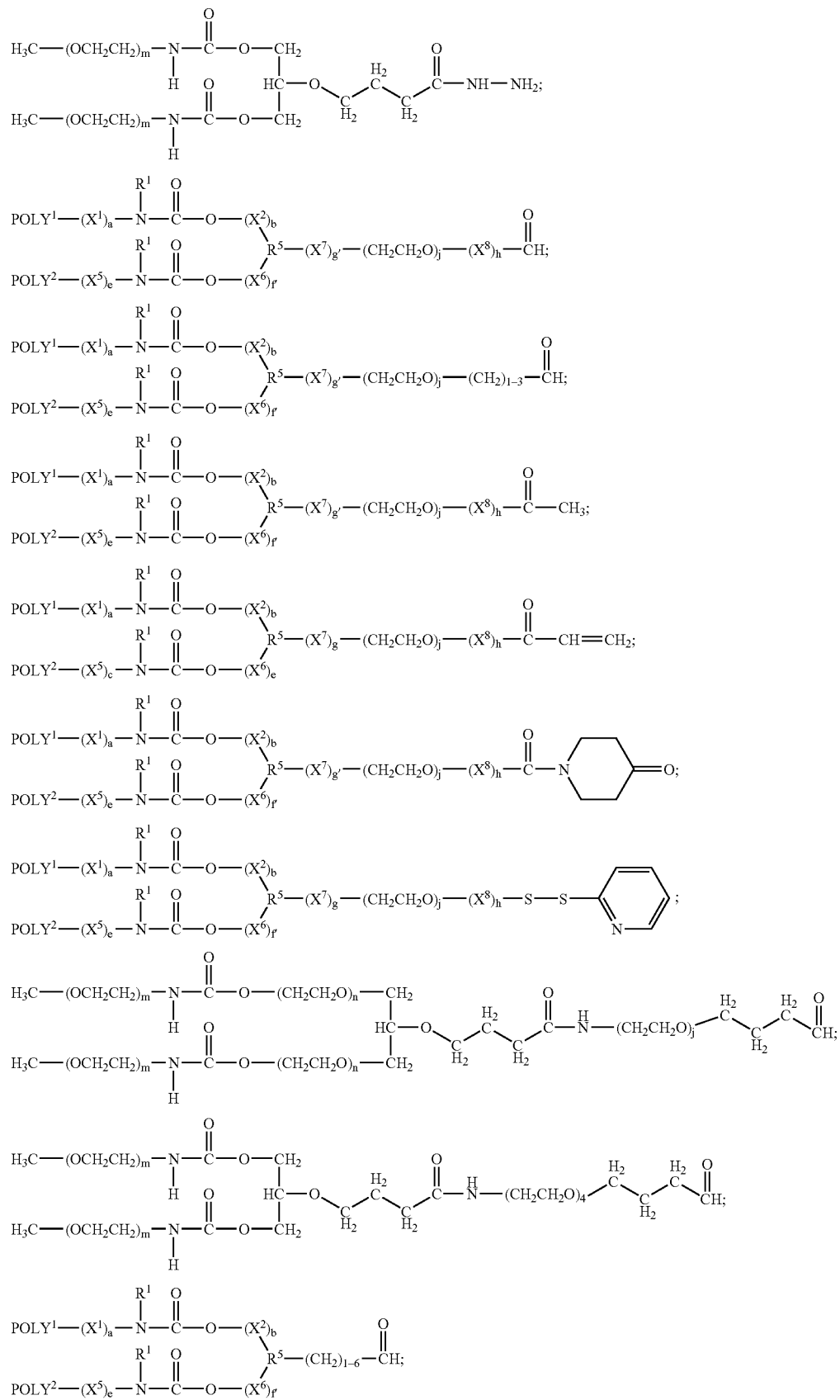

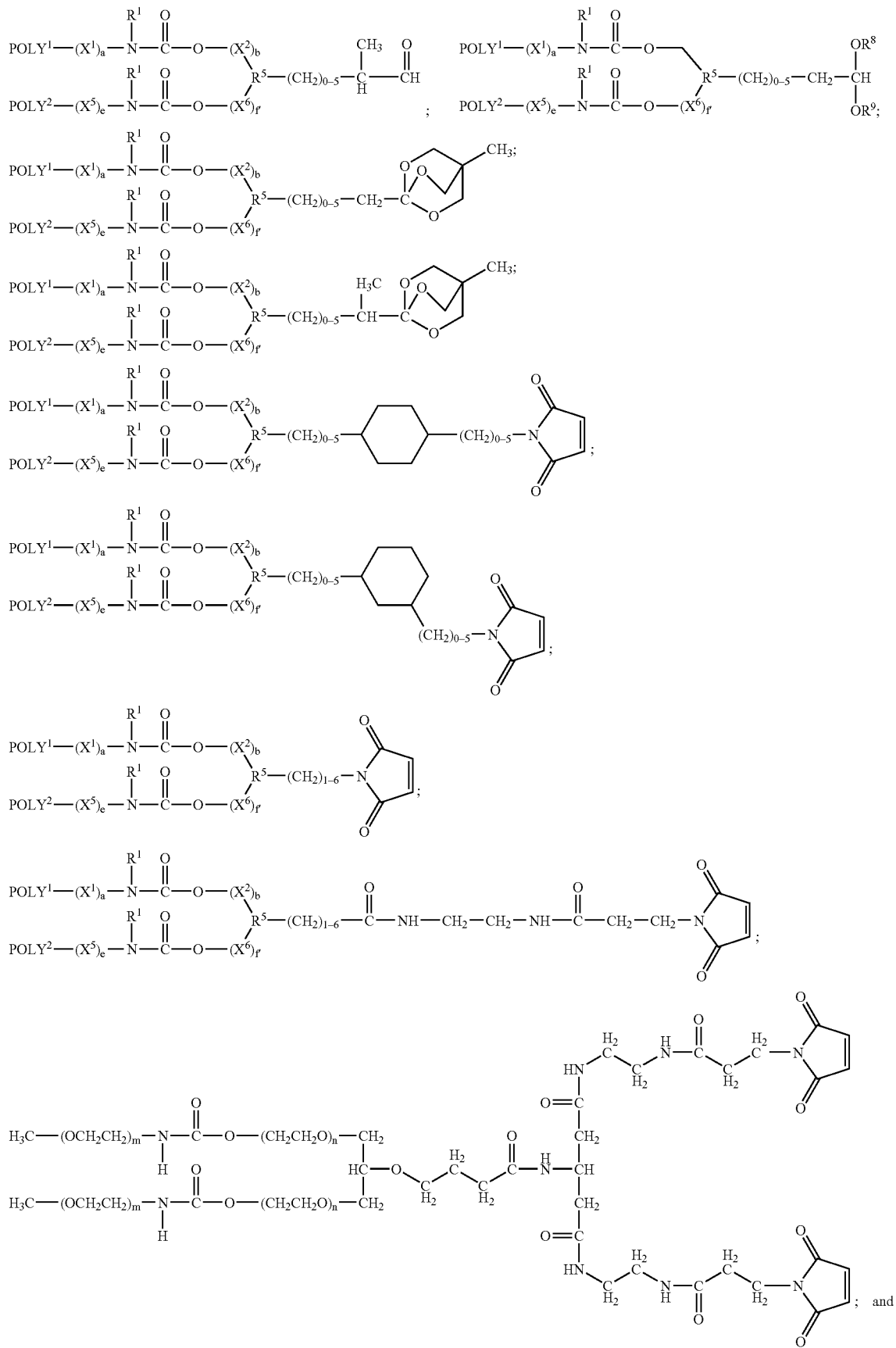

-continued
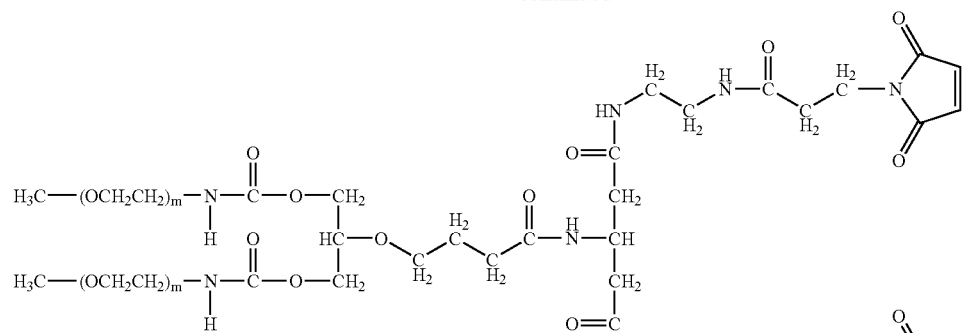
,
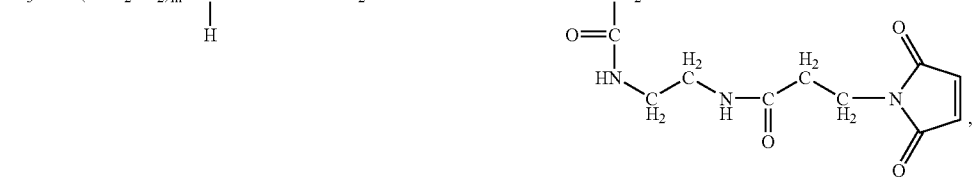
;
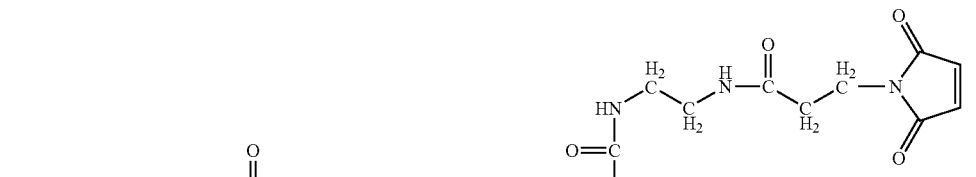
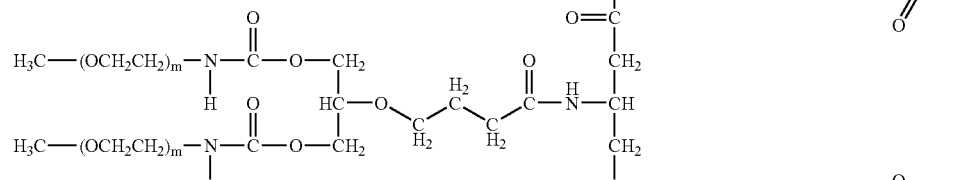
;
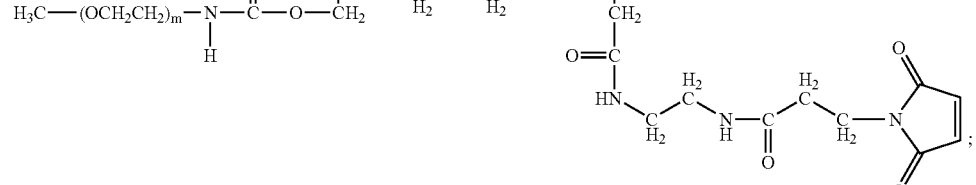

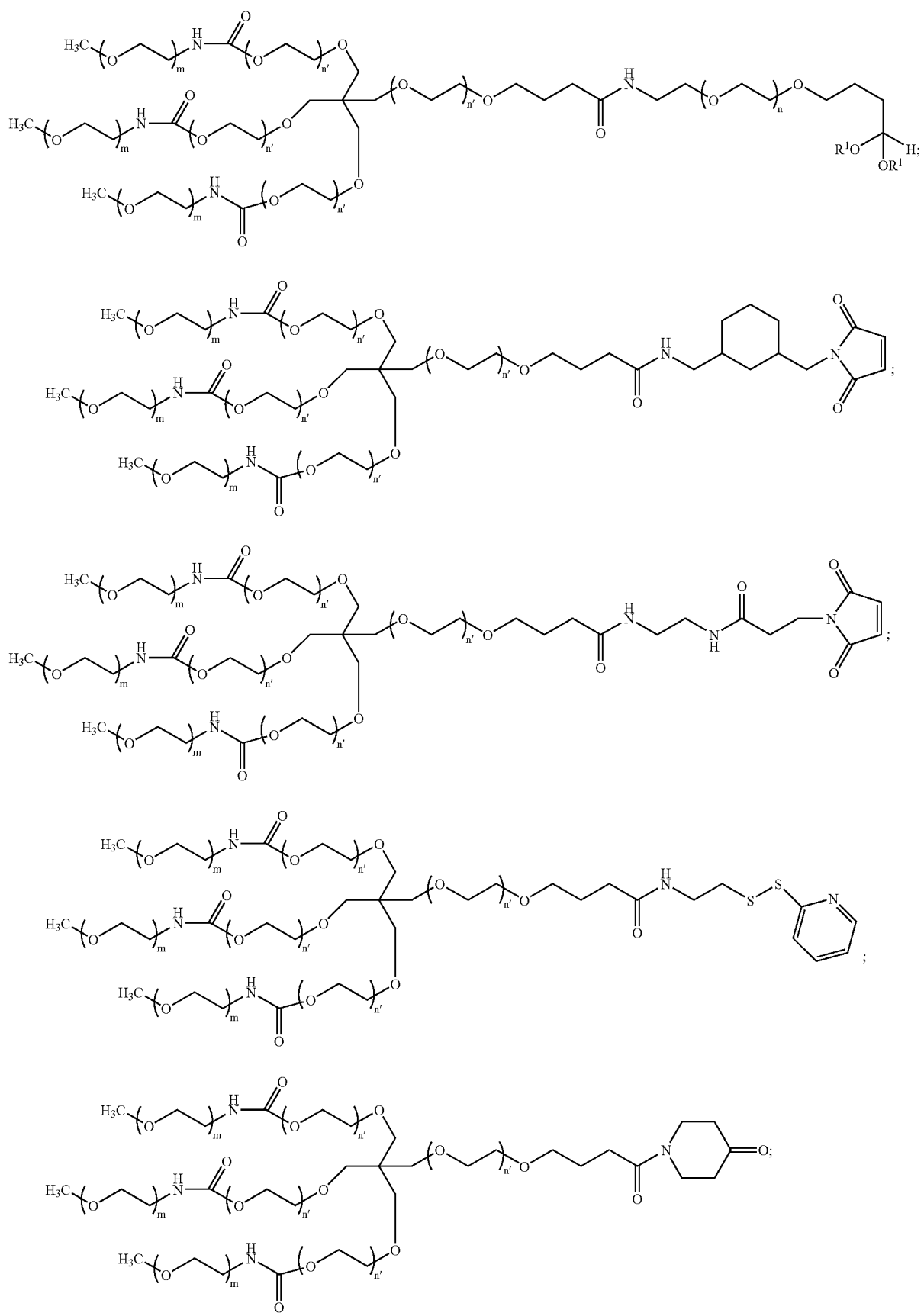

-continued

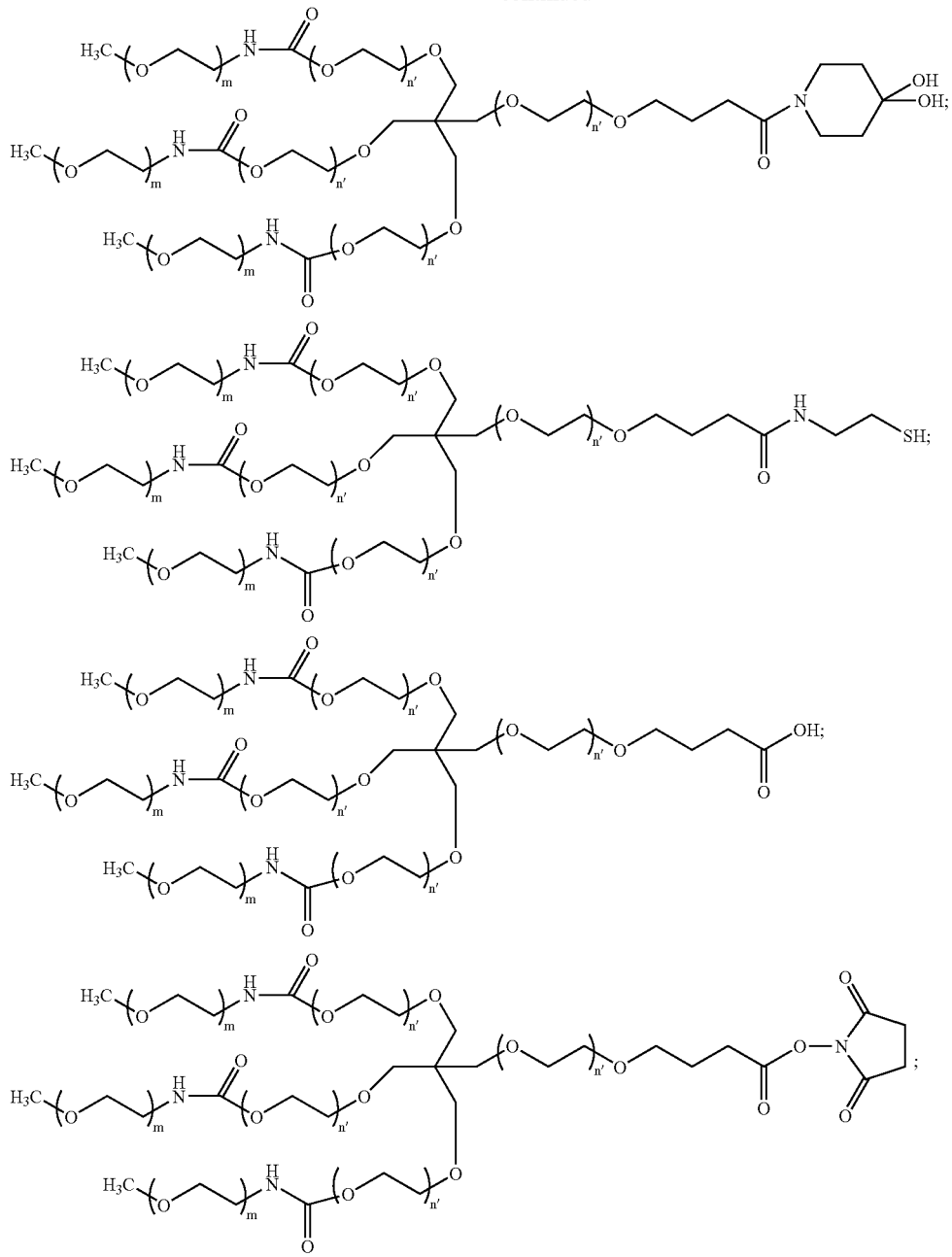

wherein all variables are as previously defined, wherein each (n') is 0-100, more preferably 0-40, and most preferably 0-20.

In certain instances, the polymeric reagents of the invention do not include a ketone moiety, i.e., a moiety wherein two separate carbon atoms are each attached to a carbon atom of a carbonyl moiety. In addition, it is preferred that the

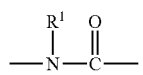

moiety is not part of a ringed structure (such as a maleimide) in some instances. Moreover, it is also preferred that the

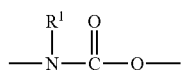

is closer to the water-soluble polymer than the reactive group, as measured, for example, in terms of the number of atoms required to reach the reactive group starting from the nearest atom in the water-soluble polymer compared to the number of atoms to reach the reactive group starting from the nearest atom in the reactive group.

The invention also includes a method for preparing the polymeric reagents provided herein. The method comprises the step of (i) providing a precursor molecule comprised of a protected reactive group (or unprotected reactive group is such reactive group can remain unaltered when carrying out the method steps) or a precursor to a reactive group and one or more hydroxyl groups. Some precursor molecules that are comprised of a protected reactive group or precursor reactive group and one or more hydroxyl groups can be obtained commercially. In addition, the unprotected forms of the precursor molecule can be synthesized and then protected (if necessary) using conventional techniques.

Although there are many forms of suitable precursor molecules, and the invention is not limited in this regard, a preferred precursor molecule has two hydroxyl groups. An example of a preferred suitable precursor molecule corresponds to Formula (IV), below.

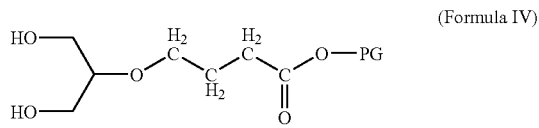

(Formula IV)

wherein PG is a protecting group. This reagent can be prepared synthetically, as described, for example, in Example 1.

Examples of preferred protecting groups include those selected from the group consisting of methyl, ethyl, t-butyl, and benzyl. A particularly preferred protecting group is methyl.

A method for preparing a polymeric reagent according to the present invention includes the step of (ii) activating at least one of the one or more hydroxyl groups of the precursor molecule for reaction with an amino group to form an activated precursor molecule. Although any suitable art-known activating reagent can be used, it is preferred to use an activating agent selected from the group consisting of di(N-succinimidyl) carbonate (DSC), N,N'-dicyclohexylcarbodiimide (DCC), N,N'-diisopropylcarbodiimide, N-(3-dimethylaminopropyl)-N'ethylcarbodiimide, 1,1'-carbonyldiimidazole (CDI), 1,1'-carbonyld(1,2,4-triazole) (CDT), bis(4-nitrophenyl) carbonate, p-nitrophenyl chlorocarbonate, 4-dimethylaminopyridine (DMAP), phosgene, triphosgene, 1-hydroxybenzotriazole (HOBt), dibenzotriazolyl carbonate (diBTC), N-hydroxysuccinimide and DCC, N-hydroxyphthalimide and DCC, and thiazolidine thione. Typically, the activating agent is added to a vessel containing the precursor molecule so that the activating agent is allowed to come into contact with the one or more hydroxyl groups of the precursor molecule.

Another step of the method for preparing the polymeric reagents of the invention includes (iii) contacting under covalent coupling conditions at least one of the one or more activated hydroxyl groups with a water-soluble polymer having an amino group, thereby forming a polymer comprised of the water-soluble polymer portion and the protected reactive group or precursor to a reactive group. Those of ordinary skill in the can determine through routine experimentation which conditions of pH, temperature, and so forth are appropriate for achieving covalent coupling. For example, the coupling step can be conducted several times, each time under a different set of conditions (e.g., different pH's, different temperatures, solvents, and so on). By determining the amount of the polymer comprised of the water-soluble polymer portion and the protected reactive group (by, for example, size-exclusion chromatography) resulting from each set of conditions, it is possible to determine which set(s) of conditions are most appropriate for carrying out the coupling step.

Although most any water-soluble polymer having an amine group can be used, it is particularly preferred to use one of the following polymers:

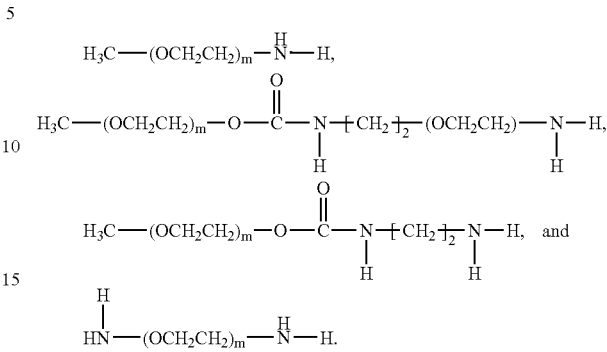

wherein (m) is 2 to 4000. Water-soluble polymers having an amine group can be synthesized de novo using techniques well known to those of ordinary skill in the art and can be obtained commercially through suppliers such as Nektar Therapeutics (Huntsville, Ala.).

When a protecting group is present in the precursor molecule, the method for preparing the polymeric reagents also includes the step of (iv) deprotecting the protected reactive group, thereby forming the polymer. The deprotecting step can be carried out using any approach suited for the removing the particular protecting group. For any specific protecting group, an appropriate deprotecting approach will be known by those of ordinary skill in the art. In addition, suitable deprotecting approaches are described in the relevant literature, such as, for example, Greene et al., supra. A preferred method for deprotecting an acid group protected as an alkyl group ester (e.g., a methyl ester) is exposing the molecule bearing the protected group to base-catalyzed hydrolysis. Examples of suitable bases to add to the reaction vessel containing the molecule bearing the protected reactive group include, without limitation, inorganic hydroxides such as sodium hydroxide, potassium hydroxide, and metal salts of weak acids such as sodium acetate, sodium carbonate, sodium bicarbonate, sodium phosphate, potassium carbonate, potassium bicarbonate, potassium citrate, potassium acetate, and so forth. Acid-catalyzed hydrolysis can also be effected with ortho esters although one may use a combination of acid-catalyzed hydrolysis followed by base-catalyzed hydrolysis with those derivatives. With acetals, acid-catalyzed hydrolysis is efficient while base-catalyzed hydrolysis is ineffective. With benzyl esters or benzyl ethers, catalytic reduction is effective although acid- or base-catalyzed hydrolysis is also effective the esters.

The method of preparing the polymeric reagents optionally comprises an additional step of isolating the polymeric reagent once it is formed. Known methods can be used to isolate the polymer, but it is particularly preferred to use chromatography, e.g., ion exchange chromatography or size exclusion chromatography. Alternately or in addition, the method includes the step of purifying the polymer once it is formed. Again, standard art-known purification methods can be used to purify the polymer.

For any given polymer prepared by the present method, the method advantageously provides the ability to further transform the polymer (either prior or subsequent to any deprotection step) so that it bears a specific reactive group. Thus, using techniques well known in the art, the polymer can be functionalized to include a reactive group (e.g., active ester, thiol, maleimide, aldehyde, ketone, and so forth).

The various steps for making a polymeric reagent are carried out in a suitable solvent. One of ordinary skill in the art can determine whether any specific solvent is appropriate for any given reaction step. Often, however, the solvent is preferably a nonpolar solvent or a polar solvent. Nonlimiting examples of nonpolar solvents include benzene, xylene and toluene. Particularly preferred nonpolar solvents include toluene, xylene, dioxane, tetrahydrofuran, and t-butyl alcohol. Exemplary polar solvents include, but are not limited to, dioxane, tetrahydrofuran (THF), t-butyl alcohol, DMSO (dimethyl sulfoxide), HMPA (hexamethylphosphoramide), DMF (dimethylformamide), DMA (dimethylacetamide), and NMP (N-methylpyrrolidinone).

The present invention also includes conjugates comprising a water-soluble polymer portion, a

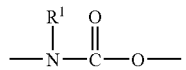

moiety, and a pharmacologically active agent. The conjugates have the following internal structural orientation: (i) the water-soluble polymer portion is linked to the nitrogen atom of the

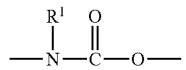

moiety through either a direct covalent bond or through a first spacer moiety; (ii) the pharmacologically active agent is linked to the carbonyl carbon atom of the

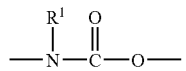

moiety through either a direct covalent bond or a second spacer moiety; and (iii) $R^1$ is H or an organic radical.

When only a single water-soluble polymer is present in the overall structure of the conjugate, the structure of the conjugate will preferably correspond to Formula V:

(Formula V)

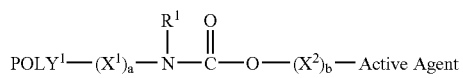

wherein:
POLY$^1$ is a water-soluble polymer (e.g., PEG or MPEG);
(a) is 0, 1, 2 or 3 (and preferably 0 or 1);
(b) is 0, 1, 2 or 3 (and preferably 0 or 1);
$R^1$ is H or an organic radical (e.g., selected from the group consisting of alkyl, substituted alkyl, alkenyl, substituted alkenyl, alkynyl, substituted alkynyl, aryl and substituted aryl;
$X^1$, when present, is a first spacer moiety;
$X^2$, when present, is a second spacer moiety; and
Active Agent is a pharmacologically active agent.

In addition, when two water-soluble polymers are present in the overall structure of the conjugate, the structure of the conjugate will preferably correspond to Formula VI:

(Formula VI)

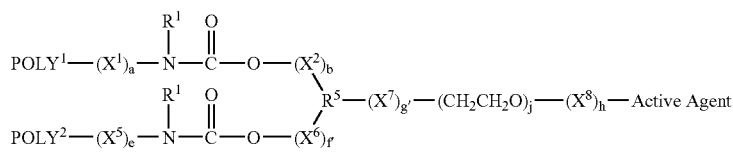

wherein:
POLY$^1$ is a water-soluble polymer (e.g., PEG or mPEG);
POLY$^2$ is a water-soluble polymer (e.g., PEG or mPEG);
(a) is 0, 1, 2 or 3 (and preferably 0 or 1);
(b) is 0, 1, 2 or 3 (and preferably 0 or 1);
(e) is 0, 1, 2 or 3 (and preferably 0 or 1);
(f') is 0, 1, 2 or 3 (and preferably 0 or 1);
(g') is 0, 1, 2 or 3 (and preferably 0 or 1);
(h) is 0, 1, 2 or 3 (and preferably 0 or 1);
is 0 to 20 (i.e., 0, 1, 2, 3, 4, 5, 6, 7, 8, 9, 10, 11, 12, 13, 14, 15, 16, 17, 18, 19 or 20);
each $R^1$ is independently H or an organic radical (e.g., selected from the group consisting of alkyl, substituted alkyl, alkenyl, substituted alkenyl, alkynyl, substituted alkynyl, aryl and substituted aryl);
$X^1$, when present, is a first spacer moiety;
$X^2$, when present, is a second spacer moiety;
$X^5$, when present, is a fifth spacer moiety;
$X^6$, when present, is a sixth spacer moiety;
$X^7$, when present, is a seventh spacer moiety;
$X^8$, when present, is an eighth spacer moiety;
$R^5$ is a branching moiety; and
Active Agent is a pharmacologically active agent.

The polymeric reagents described herein are useful for conjugation to biologically active agents or surfaces. Preferred groups suited for reaction with the polymeric reagents described herein are electrophilic and nucleophilic groups. Exemplary groups include primary amines (e.g., primary amines from the side chain of a lysine residue or the N-terminus of a polypeptide), alcohols (e.g., a primary alcohol from the side chain of a serine or threonine residue), thiols, hydrazines, hydrazides, and sulfhydryls. Such groups suited to react with the polymeric reagents described herein are known to those of ordinary skill in the art. Thus, the invention provides a method for making a conjugate comprising the step of contacting, under conjugation conditions, an active agent with a polymeric reagent described herein.

Suitable conjugation conditions are those conditions of time, temperature, pH, reagent concentration, reagent functional group(s), available functional groups on the active agent, solvent, and the like sufficient to effect conjugation between a polymeric reagent and an active agent. As is known in the art, the specific conditions depend upon, among other things, the active agent, the type of conjugation desired, the presence of other materials in the reaction mixture, and so forth. Sufficient conditions for effecting conjugation in any particular case can be determined by one of ordinary skill in the art upon a reading of the disclosure herein, reference to the relevant literature, and/or through routine experimentation.

For example, when the polymeric reagent contains an N-hydroxysuccinimide active ester (e.g., succinimidyl succinate, succinimidyl propionate, and succinimidyl butanoate), and the active agent contains an amine group (e.g., a terminal amine group on a polypeptide and/or an epsilon amine of a lysine-containing polypeptide), conjugation can be effected at a pH of from about 7.5 to about 9.5 at room temperature. In addition, when the polymeric reagent contains a vinylsulfone reactive group or a maleimide group and the pharmacologically active agent contains a sulfhydryl group (e.g., a sulfhydryl group of a cyteine-containing or methionine-containing polypeptide), conjugation can be effected at a pH of from about 7 to about 8.5 at room temperature. Moreover, when the reactive group associated with the polymeric reagent is an aldehyde or ketone and the pharmacologically active agent contains a primary amine, conjugation can be effected by reductive amination wherein the primary amine of the pharmacologically active agent reacts with the aldehyde or ketone of the polymer. Taking place at pH's of from about 6 to about 9.5, reductive amination initially results in a conjugate wherein the pharmacologically active agent and polymer are linked via an imine bond. Subsequent treatment of the imine-containing conjugate with a suitable reducing agent such as NaCNBH$_3$ reduces the imine to a secondary amine. For additional information concerning these and other conjugation reactions, reference is made to Hermanson "Bioconjugate Techniques," Academic Press, 1996.

Exemplary conjugation conditions include carrying out the conjugation reaction at a pH of from about 4 to about 10, and at, for example, a pH of about 4.0, 4.5, 5.0, 5.5, 6.0, 6.5, 7.0, 7.5, 8.0, 8.5, 9.0, 9.5, or 10.0. The reaction is allowed to proceed from about 5 minutes to about 72 hours, preferably from about 30 minutes to about 48 hours, and more preferably from about 4 hours to about 24 hours. The temperature under which conjugation can take place is typically, although not necessarily, in the range of from about 0° C. to about 40° C., and is often at room temperature or less. The conjugation reactions are often carried out using a phosphate buffer solution, sodium acetate, or similar system.

With respect to reagent concentration, an excess of the polymeric reagent is typically combined with the active agent. In some cases, however, it is preferred to have stoichiometic amounts of reactive groups on the polymeric reagent to the reactive groups of the active agent. Thus, for example, one mole of a polymeric reagent bearing two reactive groups is combined with two moles of active agent. Exemplary ratios of polymeric reagent to active agent include molar ratios of about 1:1 (polymeric reagent:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymeric reagent remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess polymeric reagent, unconjugated reactants (e.g., active agent), and undesired multi-conjugated species. The resulting conjugates can then be further characterized using analytical methods such as MALDI, capillary electrophoresis, gel electrophoresis, and/or chromatography.

The polymer-active agent conjugates can be purified to obtain/isolate different conjugated species. Alternatively, and more preferably for lower molecular weight (e.g., less than about 20,000 Dalton, more preferably less than about 10,000 Dalton) polymeric reagents used to form conjugates, the product mixture can be purified to obtain the distribution of water-soluble polymer segments per active agent. For example, the product mixture can be purified to obtain an average of anywhere from one, two, three, four or five attachments of the polymeric reagent per active agent (e.g., protein), typically an average of about attachments per active agent (e.g., protein). The strategy for purification of the final conjugate reaction mixture will depend upon a number of factors, including, for example, the molecular weight of the polymeric reagent employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymeric reagent-to-active agent ratios (e.g., 1-mer, 2-mer, 3-mer, and so forth, wherein "1-mer" indicates 1 polymeric reagent to active agent, "2-mer" indicates two polymeric reagents to active agent, and so on) on the basis of their differing molecular weights (where the difference corresponds essentially to the average molecular weight of the water-soluble polymer segments). For example, in an exemplary reaction where a 100,000 Dalton protein is randomly conjugated to a branched PEG having a total molecular weight of about 20,000 Daltons (wherein each polymer "arm" of the branched PEG has a molecular weight of about 10,000 Daltons), the resulting reaction mixture may contain unmodified protein (having a molecular weight of about 100,000 Daltons), monoPEGylated protein (having a molecular weight of about 120,000 Daltons), diPEGylated protein (having a molecular weight of about 140,000 Daltons), and so forth.

While this approach can be used to separate PEG and other polymer-active agent conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem*, 107:60-63), and (iv) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

The polymeric reagents described herein can be attached, either covalently or noncovalently, to a number of entities including films, chemical separation and purification surfaces, solid supports, metal surfaces such as gold, titanium, tantalum, niobium, aluminum, steel, and their oxides, silicon oxide, macromolecules (e.g., proteins, polypeptides, and so forth), and small molecules. Additionally, the polymeric reagents can also be used in biochemical sensors, bioelectronic switches, and gates. The polymeric reagents can also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymeric reagent as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, antibody fragments, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include but are not limited to agalsidase, alefacept, asparaginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, desmopressin, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), somatropin, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFFR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-571, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, $I^{131}$tositumomab, trastuzumab, tuvirumab and visilizumab.

Additional agents suitable for covalent attachment include, but are not limited to, tacrine, memantine, rivastigmine, galantamine, donepezil, levetiracetam, repaglinide, atorvastatin, alefacept, tadalafil, vardenafil, sildenafil, fosamprenavir, oseltamivir, valacyclovir and valganciclovir, abarelix, adefovir, alfuzosin, alosetron, amifostine, amiodarone, aminocaproic acid, aminohippurate sodium, aminoglutethimide, aminolevulinic acid, aminosalicylic acid, amlodipine, amsacrine, anagrelide, anastrozole, aprepitant, aripiprazole, asparaginase, atazanavir, atomoxetine, anthracyclines, bexarotene, bicalutamide, bleomycin, bortezomib, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daptomycin, daunorubicin, deferoxamine, dexamethasone, diclofenac, diethylstilbestrol, docetaxel, doxorubicin, dutasteride, eletriptan, emtricitabine, enfuvirtide, eplerenone, epirubicin, estramustine, ethinyl estradiol, etoposide, exemestane, ezetimibe, fentanyl, fexofenadine, fludarabine, fludrocortisone, fluorouracil, fluoxymesterone, flutamide, fluticazone, fondaparinux, fulvestrant, gamma-hydroxybutyrate, gefitinib, gemcitabine, epinephrine, L-Dopa, hydroxyurea, icodextrin, idarubicin, ifosfamide, imatinib, irinotecan, itraconazole, goserelin, laronidase, lansoprazole, letrozole, leucovorin, levamisole, lisinopril, lovothyroxine sodium, lomustine, mechlorethamine, medroxyprogesterone, megestrol, melphalan, memantine, mercaptopurine, mequinol, metaraminol bitartrate, methotrexate, metoclopramide, mexiletine, miglustat, mitomycin, mitotane, mitoxantrone, modafinil, naloxone, naproxen, nevirapine, nicotine, nilutamide, nitazoxanide, nitisinone, norethindrone, octreotide, oxaliplatin, palonosetron, pamidronate, pemetrexed, pergolide, pentostatin, pilcamycin, porfimer, prednisone, procarbazine, prochlorperazine, ondansetron, palonosetron, oxaliplatin, raltitrexed, rosuvastatin, sirolimus, streptozocin, pimecrolimus, sertaconazole, tacrolimus, tamoxifen, tegaserod, temozolomide, teniposide, testosterone, tetrahydrocannabinol, thalidomide, thioguanine, thiotepa, tiotropium, topiramate, topotecan, treprostinil, tretinoin, valdecoxib, celecoxib, rofecoxib, valrubicin, vinblastine, vincristine, vindesine, vinorelbine, voriconazole, dolasetron, granisetron, formoterol, fluticasone, leuprolide, midazolam, alprazolam, amphotericin B, podophylotoxins, nucleoside antivirals, aroyl hydrazones, sumatriptan, eletriptan; macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, gatifloxacin, gemifloxacin, grepafloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, salmeterol, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO, IFN-α, IFN-β, consensus IFN, Factor VIII, B-domain deleted factor VIII, Factor IX, GCSF, GMCSF, hGH, insulin, FSH, peptides having GLP-1 activity, desmopressin, amdoxivir, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. In addition, the term "active agent" is intended to encompass the active agent prior to conjugation as well as the active agent "residue" following conjugation.

A particularly preferred pharmacologically active agent is a peptide that has agonist or antagonist activity to the glucagon-like peptide (GLP-1) receptor. GLP-1 and its pharmacologically active agonist derivatives thereof stimulate insulin secretion by beta cells and inhibit glucagon secretion in vivo. Such agonists for the GLP-1 recepetor are useful in the regulation of insulin production.

Examples of GLP-1 related agents that are useful as conjugates include, without limitation, the following: native GLP-1; exendin-3; exendin-4; exendin-4 (1-30); exendin-4 (1-30) amide; exendin-4 (1-28) amide; $^{14}$Leu, $^{25}$Phe exendin-4 amide; $^{14}$Leu, $^{25}$Phe exendin-4 (1-28) amide; $^{14}$Leu, $^{22}$Ala, $^{25}$Phe exendin-4 (1-28) amide, or a pharmacologically active derivative thereof. These and other agents having agonist activity for the GLP-1 receptor are described in WO99/07404 and include agents having a structure corresponding to the general formula $Xaa_1$ $Xaa_2$ $Xaa_3$ Gly Thr $Xaa_4$ $Xaa_5$ $Xaa_6$ $Xaa_7$ $Xaa_8$ Ser Lys Gln $Xaa_9$ Glu Glu Glu Ala Val Arg Leu $Xaa_{10}$ $Xaa_{11}$ $Xaa_{12}$ $Xaa_{13}$ Leu Lys Asn Gly Gly $Xaa_{14}$ Ser Ser Gly Ala $Xaa_{15}$ $Xaa_{16}$ $Xaa_{17}$ $Xaa_{18}$-Z, (SEQ. ID. NO.: 1) wherein: $Xaa_1$ is His, Arg or Tyr; $Xaa_2$ is Ser, Gly, Ala or Thr; $Xaa_3$ is Asp or Glu; $Xaa_4$ is Phe, Tyr or naphthylalanine; $Xaa_5$ is Thr or Ser; $Xaa_6$ is Ser or Thr; $Xaa_7$ is Asp or Glu; $Xaa_8$ is Leu, Ile, Val, pentylglycine or Met; $Xaa_9$ is Leu, Ile, pentylglycine, Val or Met; $Xaa_{10}$, is Phe, Tyr or naphthylalanine; $Xaa_{11}$ is Ile, Val, Leu, pentylglycine, tert-butylglycine or Met; $Xaa_{12}$ is Glu or Asp; $Xaa_{13}$ is Trp, Phe, Tyr, or naphthylalanine; $Xaa_{14}$, $Xaa_{15}$, $Xaa_{16}$ and $Xaa_{17}$ are independently Pro, homoproline, 3Hyp, 4Hyp, thioproline, N-alkylglycine, N-alkylpentylglycine or N-alkylalanine; $Xaa_{18}$ is Ser, Thr or Tyr; and Z is —OH or —NH$_2$.

Other GLP-1 agonists are described in U.S. Pat. No. 6,583, 111. Particularly preferred agonists described in this reference include NH$_2$-His$^7$-Ala-Glu-Gly$^{10}$-Thr-Phe-Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-Gly$^{37}$-OH (SEQ ID NO: 2), NH$_2$-His$^7$-Ala-Glu-Gly$^{10}$-Thr-Phe-Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-NH$_2$ (SEQ ID NO: 3), and NH$_2$-His$^7$-Val-Glu-Gly$^{10}$-Thr-Phe- Thr-Ser-Asp$^{15}$-Val-Ser-Ser-Tyr-Leu$^{20}$-Glu-Gly-Gln-Ala-Ala$^{25}$-Lys-Glu-Phe-Ile-Ala$^{30}$-Trp-Leu-Val-Lys-Gly$^{35}$-Arg-Gly$^{37}$-OH (SEQ ID NO: 4)

Additional examples of agents that are useful as conjugates, include, without limitation, those described in WO 01/23420. As described therein, many of following polypeptides can be made by conventional solid state-based synthetic techniques (as described in Peptide Synthesis Protocols (1994), Volume 35 by Micheal W. Pennington & Ben M. Dunn) and/or by recombinant-based techniques. Particularly preferred sequences include:

| Polypeptide | SEQ. ID. No.: |
|---|---|
| Ac-HSDAVFTENYTKLRKQNIeAAKKYLNDLKKGGT-NH$_2$ | 5 |
| Ac-HSDAVFTENYTKLRKQLAAKKYLNDLKKGGT-NH$_2$ | 6 |
| Ac-HSDAVFTENYTKLRKQLAAKKYLNDLKKGGT | 7 |
| HSDAVFTENYTKLRKQLAAKKYLNDLKKGGT | 8 |
| Ac-HSDAVFTEN(CH30-Y)TKLRKQNIeAAKKYLNDLKK-NH$_2$ | 9 |
| HSDAVFTENYTKLRKQLAAKKYLNDLKK | 10 |
| HSDAVFTDNYTRLRKQMAVKKYLNSIKK-NH$_2$ | 11 |
| HSDAVFTDNYTRLRKQMAVKKYLNSIKKGGT | 12 |
| HSDAVFTENYTKLRKQLAAKKYLNDLLNGGT | 13 |
| HSDAVFTDNYTKLRKQLAAKKYLNDILNGGT | 14 |
| HSDAVFTDNYTRLRKQLAAKKYLNDIKKGGT | 15 |
| HSDAVFTDNYTRLRKQLAAKKYLNDIKK-NH$_2$ | 16 |
| HSDAVFTDNYTRLRKQMAVKKYLNDLKKGGT | 17 |
| HSDAVFTENYTKLRKQLAAKKYLNDLKKGGTSWCEPGWCR | 18 |
| HSDAVFTDNYTRLRKQMAAKKYLNDIKKGGT | 19 |
| HSDAVFTDNYTRLRKQLAVKKYLNDIKKGGT | 20 |
| HSDAVFTDNYTRLRKQLAAKKYLNSIKKGGT | 21 |
| HSDAVFTDNYTRLRKQLAAKKYLNDIKNGGT | 22 |
| HSDAVFTDNYTRLRKQLAVKKYLNSIKKGGT | 23 |
| HSDAVFTDNYTRLRKQMAAKKYLNSIKKGGT | 24 |
| HSDAVFTDNYTRLRKQLAVKKYLNDIKNGGT | 25 |
| HSDAVFTDNYTRLRKQLAAKKYLNSIKNGGT | 26 |
| HSDAVFTDNYTRLRKQLAAKKYLNDIKKGG | 27 |
| HSDAVFTDNYTRLRKQLAAKKYLNDIKKG | 28 |
| HSDAVFTDNYTRLRKQLAAKKYLNDIKK | 29 |
| HSDAVFTDNYTRLRKQLAAKKYLNDIKKQ | 30 |
| HSDAVFTDNYTRLRKQLAAKKYLNDIKKNQ | 31 |
| HSDAVFTDNYTRLRKQLAAKKYLNDIKKKRY | 32 |
| HSDAVFTDNYTRLRKQMAVKKYLNSIKK | 33 |
| HSDAVFTDNYTRLRKQMAVKKYLNSIKN | 34 |
| HSDAVFTDNYTRLRKQMAVKKYLNSILK | 35 |
| HSDAVFTDNYTELRKQMAVKKYLNSILN | 36 |
| HSDAVFTDNYTRLREQMAVKKYLNSILN | 37 |
| HSDAVFTDNYTRLRKQLAVKKYLNSILN | 38 |
| HSDAVFTDNYTRLRKQMAAKKYLNSILN | 39 |
| HSDAVFTDNYTRLRKQMAVKKYLNDILN | 40 |
| HSDAVFTDNYTRLRKQMAAKKYLNSIKN | 41 |
| HSDAVFTDNYTRLRKQMAAKKYLNSILK | 42 |
| HSDAVFTDNYTRLRKQMAAKKYLNSIKK | 43 |
| HSDAVFTDNYTRLRKQMAAKKYLNSIKKKRY | 44 |
| HSDAVFTDNYTRLRKQMAAKKYLNSIKKKR | 45 |
| HSDAVFTDNYTRLRKQMAAKKYLNSIKKK | 46 |
| HSDAVFTDNYTRLRKQMAAKKYLNSIKNKRY | 47 |
| HSDAVFTDNYTRLRKQMAVKKYLNSIKKKRY | 48 |
| HSDAVFTDNYTRLRKQMAVKKYLNSIKKKR | 49 |
| DAVFTDNYTRLRKQMAVKKYLNSIKKK | 50 |
| HSDAVFTDNYTRLRKQMAVKKYLNSIKNKRY | 51 |
| HSDAVFTDNYTRLRKQVAAKKYLQSIKK | 52 |
| HSDAVFTDNYTRLRKQIAAKKYLQTIKK | 53 |
| HSDGIFTESYSRYRKQMAVKKYLAALKKKPYKQRVKNK | 54 |
| HSDAVFTENYTRLRKQMAVKKYLNSLKK-NH$_2$ | 55 |
| HSDGIFTDSYSRYRKQMAVKKYLSAVRHGQT-NH$_2$ | 56 |
| HSDGIFTDSYSRYRKQMAVKKYLAAVKQGGT-NH$_2$ | 57 |
| HSDGIFTDSYSRYRKQMAVKKYLAAVKKYLAAVRHG-NH$_2$ | 58 |
| SWCEPGWCRHSDAVFTENYTKLRKQLAAKKYLNDLKKGGT | 59 |
| HSDAVFTDNYTRLRKQLAAKKYLNDILKGGT | 60 |
| HSDAVFTDNYTRLRKQLAAKKYLNDILNGGT | 61 |
| HSDAVFTDNYTRLRKQLAVKKYLNDILKGGT | 62 |
| HSDGIFTDSYSRYRKQLAAKKYLADVKKGGT | 63 |
| HSDGIFTDSYSRYRKQLAAKKYLADVKK | 64 |
| HSDGIFTDSYSRYRKQLAVKKYLAAVKK | 65 |
| HSDGIFTDSYSRYRKQMAVKKYLAAVKK | 66 |
| HSDAVFTDNYTRLRKQVAAKKYLNSIKK | 67 |
| HSDAVFTDNYTRLRKQMAAKKYLNSIKNKR | 68 |
| HSDAVFTDNYTRLRKQVAAKKYLQSIKNKRY | 69 |
| HSDAVFTDNYTRLRKQLAAKKYLNTIKNKRY | 70 |
| HSDAVFTDNYTRLRKQVAAKKYLNSIKNKRY | 71 |
| HSDAVFTDNYTRLRKQMAAKKYLQSIKNKRY | 72 |
| HSDAVFTDNYTRLRKQMAAKKYLNTIKNKRY | 73 |

| Polypeptide | SEQ. ID. No.: |
|---|---|
| HSDAVFTDQYTRLRKQMAAKKYLNSIKNKRY | 74 |
| HSDAVFTDQYTRLRKQLAAKKYLNTIKNKRY | 75 |
| HSDAVFTDNYTRLRKQMAAHKYLNSIKNKRY | 76 |
| HSDAVFTDNYTRLRKQMAAKHYLNSIKNKRY | 77 |
| HSDAVFTDQYTRLRKQLAAHKYLNTIKNKRY | 78 |
| HSDAVFTDQYTRLRKQLAAHKYLNTIKNKRY | 79 |
| HSDAVFTDNYTRLRKQVAAKKYLQSIKKKR | 80 |
| HSDAVFTDNYTRLRKQVAAKKYLNSIKKKR | 81 |
| HSDAVFTDNYTRLRKQVAAKKYLNSIKNKRY | 82 |
| HSDAVFTDNYTRLRKQVAVKKYLQSIKKKR | 83 |
| HSDAVFTDNYTRLRKQVAVKKYLQSIKKK | 84 |
| HSDAVFTDNYTRLRKQVAVKKYLQSIKNKRY | 85 |
| HSDAVFTDNYTRLRKQVAAKKYLQSILKKRY | 86 |
| HSDAVFTDNYTRLRKQVAAKKYLQSILKKR | 87 |
| HSDAVFTDNYTRLRKQVAAKKYLQSILKK | 88 |
| HSDAVFTDNYTRLRKQVAAKKYLQSIKNK | 89 |
| HSDAVFTDNYTRLRKQVAVKKYLQSILKKRY | 90 |
| HSDAVFTDNYTRLRKQVAVKKYLQSILKKR | 91 |
| HSDAVFTDNYTRLRKQVAVKKYLQSILKK | 92 |
| HSDAVFTDNYTRLRKQVAAKKYLQSILNKRY | 93 |
| HSDAVFTDNYTRLRKQVAAKKYLQSILNKR | 94 |
| HSDAVFTDNYTRLRKQVAAKKYLQSILNK | 95 |
| HSDAVFTDNYTRLRKQMACKKYLNSIKNKR | 96 |
| HSDAVFTDNYTRLRKQMADKKYLNSIKNKR | 97 |
| HSDAVFTDNYTRLRKQMAEKKYLNSIKNKR | 98 |
| HSDAVFTDNYTRLRKQMAFKKYLNSIKNKR | 99 |
| HSDAVFTDNYTRLRKQMAGKKYLNSIKNKR | 100 |
| HSDAVFTDNYTRLRKQMAHKKYLNSIKNKR | 101 |
| HSDAVFTDNYTRLRKQMAIKKYLNSIKNKR | 102 |
| HSDAVFTDNYTRLRKQMAKKKYLNSIKNKR | 103 |
| HSDAVFTDNYTRLRKQMALKKYLNSIKNKR | 104 |
| HSDAVFTDNYTRLRKQMAMKKYLNSIKNKR | 105 |
| HSDAVFTDNYTRLRKQMANKKYLNSIKNKR | 106 |
| HSDAVFTDNYTRLRKQMAPKKYLNSIKNKR | 107 |
| HSDAVFTDNYTRLRKQMAQKKYLNSIKNKR | 108 |
| HSDAVFTDNYTRLRKQMARKKYLNSIKNKR | 109 |
| HSDAVFTDNYTRLRKQMASKKYLNSIKNKR | 110 |
| HSDAVFTDNYTRLRKQMATKKYLNSIKNKR | 111 |
| HSDAVFTDNYTRLRKQMAVKKYLNSIKNKR | 112 |
| HSDAVFTDNYTRLRKQMAWKKYLNSIKNKR | 113 |
| HSDAVFTDNYTRLRKQMAYKKYLNSIKNKR | 114 |
| HSDAVFTDNYTRLRKQMAAKKYLNSIANKR | 115 |
| HSDAVFTDNYTRLRKQMAAKKYLNSICNKR | 116 |
| HSDAVFTDNYTRLRKQMAAKKYLNSIDNKR | 117 |
| HSDAVFTDNYTRLRKQMAAKKYLNSIENKR | 118 |
| HSDAVFTDNYTRLRKQMAAKKYLNSIFNKR | 119 |
| HSDAVFTDNYTRLRKQMAAKKYLNSIGNKR | 120 |
| HSDAVFTDNYTRLRKQMAAKKYLNSIHNKR | 121 |
| HSDAVFTDNYTRLRKQMAAKKYLNSIINKR | 122 |
| HSDAVFTDNYTRLRKQMAAKKYLNSIMNKR | 123 |
| HSDAVFTDNYTRLRKQMAAKKYLNSINNKR | 124 |
| HSDAVFTDNYTRLRKQMAAKKYLNSIPNKR | 125 |
| HSDAVFTDNYTRLRKQMAAKKYLNSIQNKR | 126 |
| HSDAVFTDNYTRLRKQMAAKKYLNSIRNKR | 127 |
| HSDAVFTDNYTRLRKQMAAKKYLNSISNKR | 128 |
| HSDAVFTDNYTRLRKQMAAKKYLNSITNKR | 129 |
| HSDAVFTDNYTRLRKQMAAKKYLNSIVNKR | 130 |
| HSDAVFTDNYTRLRKQMAAKKYLNSIWNKR | 131 |
| HSDAVFIDNYTRLRKQMAAKKYLNSIYNKR | 132 |
| HSDAVFTDNYTRLRKQMAAKKYLNSIKNAR | 133 |
| HSDAVFTDNYTRLRKQMAAKKYLNSIKNCR | 134 |
| HSDAVFTDNYTRLRKQMAAKKYLNSIKNDR | 135 |
| HSDAVFTDNYTRLRKQMAAKKYLNSIKNER | 136 |
| HSDAVFTDNYTRLRKQMAAKKYLNSIKNFR | 137 |
| HSDAVFTDNYTRLRKQMAAKKYLNSIKNGR | 138 |
| HSDAVFTDNYTRLRKQMAAKKYLNSIKNHR | 139 |
| HSDAVFTDNYTRLRKQMAAKKYLNSIKNIR | 140 |
| HSDAVFTDNYTRLRKQMAAKKYLNSIKNLR | 141 |
| HSDAVFTDNYTRLRKQMAAKKYLNSIKNMR | 142 |
| HSDAVFTDNYTRLRKQMAAKKYLNSIKNNR | 143 |
| HSDAVFTDNYTRLRKQMAAKKYLNSIKNPR | 144 |
| HSDAVFTDNYTRLRKQMAAKKYLNSIKNQR | 145 |
| HSDAVFTDNYTRLRKQMAAKKYLNSIKNRR | 146 |
| HSDAVFTDNYTRLRKQMAAKKYLNSIKNSR | 147 |
| HSDAVFTDNYTRLRKQMAAKKYLNSIKNTR | 148 |
| HSDAVFTDNYTRLRKQMAAKKYLNSIKNVR | 149 |
| HSDAVFTDNYTRLRKQMAAKKYLNSIKNWR | 150 |

| Polypeptide | SEQ. ID. No.: |
|---|---|
| HSDAVFTDNYTRLRKQMAAKKYLNSIKNYR | 151 |
| HSDAVFTDNYTRLRKQMAAKKYLNSIKNKA | 152 |
| HSDAVFTDNYTRLRKQMAAKKYLNSIKNKD | 153 |
| HSDAVFTDNYTRLRKQMAAKKYLNSIKNKE | 154 |
| HSDAVFTDNYTRLRKQMAAKKYLNSIKNKF | 155 |
| HSDAVFTDNYTRLRKQMAAKKYLNSIKNKG | 156 |
| HSDAVFTDNYTRLRKQMAAKKYLNSIKNKH | 157 |
| HSDAVFTDNYTRLRKQMAAKKYLNSIKNKI | 158 |
| HSDAVFTDNYTRLRKQMAAKKYLNSIKNKK | 159 |
| HSDAVFTDNYTRLRKQMAAKKYLNSIKNKL | 160 |
| HSDAVFTDNYTRLRKQMAAKKYLNSIKNKM | 161 |
| HSDAVFTDNYTRLRKQMAAKKYLNSIKNKN | 162 |
| HSDAVFTDNYTRLRKQMAAKKYLNSIKNKP | 163 |
| HSDAVFTDNYTRLRKQMAAKKYLNSIKNKQ | 164 |
| HSDAVFTDNYTRLRKQMAAKKYLNSIKNKS | 165 |
| HSDAVFTDNYTRLRKQMAAKKYLNSIKNKT | 166 |
| HSDAVFTDNYTRLRKQMAAKKYLNSIKNKV | 167 |
| HSDAVFTDNYTRLRKQMAAKKYLNSIKNKW | 168 |
| HSDAVFTDNYTRLRKQMAAKKYLNSIKNKY | 169 |
| HSDAVFTDNYTRLRKQVAAKKYLQSIKNKRYSWCEPGWCR | 170 |
| HSDAVFTDDYTRLRKEVAAKKYLESIKDKRY | 171 |
| ESDGIFTDSYSRYRKQMAVKKYLAAVL-NH$_2$ | 172 |
| HKDGIFTDSYSRYRKQMAVKKYLAAVL-NH$_2$ | 173 |
| HSKGIFTDSYSRYRKQMAVKKYLAAVL-NH$_2$ | 174 |
| HSDKIFTDSYSRYRKQMAVKKYLAAVL-NH$_2$ | 175 |
| HSDGKFTDSYSRYRKQMAVKKYLAAVL-NH$_2$ | 176 |
| HSDGIKTDSYSRYRKQMAVKKYLAAVL-NH$_2$ | 177 |
| HSDGIFKDSYSRYRKQMAVKKYLAAVL-NH$_2$ | 178 |
| HSDGIFTKSYSRYRKQMAVKKYLAAVL-NH$_2$ | 179 |
| HSDGIFTDKYSRYRKQMAVKKYLAAVL-NH$_2$ | 180 |
| HSDGIFTDSKSRYRKQMAVKKYLAAVL-NH$_2$ | 181 |
| HSDGIFTDSYKRYRKQMAVKKYLAAVL-NH$_2$ | 182 |
| HSDGIFTDSYSEYRKQMAVKKYLAAVL-NH$_2$ | 183 |
| HSDGIFTDSYSRKRKQMAVKKYLAAVL-NH$_2$ | 184 |
| HSDGIFTDSYSRYEKQMAVKKYLAAVL-NH$_2$ | 185 |
| HSDGIFTDSYSRYREQMAVKKYLAAVL-NH$_2$ | 186 |
| HSDGIFTDSYSRYRKKMAVKKYLAAVL-NH$_2$ | 187 |
| HSDGIFTDSYSRYRKQKAVKKYLAAVL-NH$_2$ | 188 |
| HSDGIFTDSYSRYRKQMKVKKYLAAVL-NH$_2$ | 189 |
| HSDGIFTDSYSRYRKQMAKKKYLAAVL-NH$_2$ | 190 |
| HSDGIFTDSYSRYRKQMAVEKYLAAVL-NH$_2$ | 191 |
| HSDGIFTDSYSRYRKQMAVKEYLAAVL-NH$_2$ | 192 |
| HSDGIFTDSYSRYRKQMAVKKKLAAVL-NH$_2$ | 193 |
| HSDGIFTDSYSRYRKQMAVKKYKAAVL-NH$_2$ | 194 |
| HSDGIFTDSYSRYRKQMAVKKYLKAVL-NH$_2$ | 195 |
| HSDGIFTDSYSRYRKQMAVKKYLAKVL-NH$_2$ | 196 |
| HSDGIFTDSYSRYRKQMAVKKYLAAKL-NH$_2$ | 197 |
| HSDGIFTDSYSRYRKQMAVKKYLAAVK-NH$_2$ | 198 |
| HSDAVFTDNYTRLRKQMAAKKYLNSIKNRI | 199 |
| HSDAVFTDNYTRLRKQMAGKKYLNSIKNRI | 200 |
| HSDAVFTDNYTRLRKQMAKKKYLNSIKNRI | 201 |
| HSDAVFTDNYTRLRKQMARKKYLNSIKNRI | 202 |
| HSDAVFTDNYTRLRKQMASKKYLNSIKNRI | 203 |
| HSDAVFTDNYTRLRKQMAAKKYLNSIPNRI | 204 |
| HSDAVFTDNYTRLRKQMAGKKYLNSIPNRI | 205 |
| HSDAVFTDNYTRLRKQMAKKKYLNSIPNRI | 206 |
| HSDAVFTDNYTRLRKQMARKKYLNSIPNRI | 207 |
| HSDAVFTDNYTRLRKQMASKKYLNSIPNRI | 208 |
| HSDAVFTDNYTRLRKQMAAKKYLNSIQNRI | 209 |
| HSDAVFTDNYTRLRKQMAGKKYLNSIQNRI | 210 |
| HSDAVFTDNYTRLRKQMAKKKYLNSIQNRI | 211 |
| HSDAVFTDNYTRLRKQMARKKYLNSIQNRI | 212 |
| HSDAVFTDNYTRLRKQMASKKYLNSIQNRI | 213 |
| HSDAVFTDNYTRLRKQMAAKKYLNSIRNRI | 214 |
| HSDAVFTDNYTRLRKQMAGKKYLNSIRNRI | 215 |
| HSDAVFTDNYTRLRKQMAKKKYLNSIRNRI | 216 |
| HSDAVFTDNYTRLRKQMARKKYLNSIRNRI | 217 |
| HSDAVFTDNYTRLRKQMASKKYLNSIRNRI | 218 |

Further examples of peptide agonists having GLP-1 activity are described in U.S Pat. No. 6,528,486 and include, for example, H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-(Lys)$_6$-NH$_2$ (SEQ ID NO: 219), H-Lys$_6$-His-Gly-Gly-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-(Lys)$_6$-NH$_2$ (SEQ ID NO: 220), H-His-Gly-Glu-Gly-Thr-Phe-Thr-Ser-Asp-Leu-Ser-Lys-Gln-Met-Glu-Glu-Glu-Ala-Val-Arg-Leu-Phe-Ilee-Glu-Trp-Leu-Lys-Asn-Gly-Gly-Pro-Ser-Ser-Gly-Ala-Ser-NH$_2$ (SEQ ID NO: 344), H-Lys-Lys-Lys-Lys-Lys-Lys-His-Gly-Glu-Gly-Thr-Phe-Thr-Ser-Asp-Leu-Ser-Lys-Gln-Met-Glu-Glu-Glu-Ala-Val-Arg-Leu-Phe-Ile- Glu-Trp-Leu-Lys-Asn-Gly-Gly-Pro-Ser-Ser-Gly-Ala-Ser-NH$_2$ (SEQ ID NO: 222), H-Asn-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-NH$_2$ (SEQ ID NO: 223), H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (SEQ ID NO: 224), H-(Lys)$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (SEQ ID NO: 225), and H-Asp-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$-NH$_2$ (SEQ ID NO: 226);

All amino acid abbreviations use conventional and commonly accepted forms, as follows: Phenylalanine is Phe or F; Leucine is Leu or L; Isoleucine is ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Acetylated peptides possess the prefix "Ac".

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents, patent applications, and publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C and pressure is at or near atmospheric pressure at sea level. All reagents were obtained commercially unless otherwise indicated. The following abbreviations are used herein and elsewhere in the specification.

Example 1

Preparation of a Glycerol-based Precursor Molecule

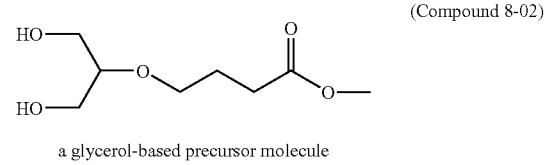

a glycerol-based precursor molecule

A solution of cis-1,3-O-Benzylideneglycerol (7.2 g, 0.040 moles) (Sigma-Aldrich Corporation, St. Louis, Mo.) in toluene (100 ml) was azeotropically dried by distilling off toluene. The dried compound was dissolved in anhydrous toluene (100 ml) and 1.0M solution of potassium tert-butoxide in tert-butanol (60 ml, 0.060 moles) and 1-(3-bromopropyl)-4-methyl-2,6,7-trioxabicyclo[2,2,2]octane (14.0 g, 0.0558 moles) were added and the mixture was stirred overnight at 100° C. under argon atmosphere. The mixture was filtered and the solvent was distilled off under reduced pressure giving 15.7 g of solid product (Compound 5-02). NMR ($d_6$-DMSO): 0.74 ppm (s, 3H), 1.61 ppm (m, 4H), 1.88 ppm (m, 2H), 3.44 ppm (t, 2H), 3.81 ppm(s, 6H), 4.05 ppm (m, 4H), 5.55 ppm (s, 1H), 7.37 ppm (m, 5H).

Schematically, the reaction is represented as follows:

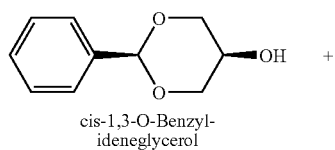

cis-1,3-O-Benzylideneglycerol

1-(3-bromopropyl)-4-methyl-2,6,7-trioxabicyclo[2,2,2]octane

Compound 5-02

Hydrolysis of 5-02. Compound 5-02 (15.0 g) was dissolved in a mixture of acetonitrile (150 ml) and distilled water (35 ml). Next, a 10% solution of $H_3PO_4$ was added to adjust the pH to 4.5. The mixture was stirred for 1 hour at pH=4.5. NaCl (2 g) was added and the pH was adjusted to 7.5. The product was extracted with $CH_2Cl_2$ (600 and 150 ml).

The extract was dried ($MgSO_4$) and the solvent was distilled off under reduced pressure to give a solid product (Compound 6-02). The yield was determined to be 14.2 g. NMR (d6-DMSO): 0.78 ppm (s, 3H), 1.79 ppm (m, 2H), 2.41 ppm (t, 2H), 3.25 ppm (m, 6H), 3.49 ppm (t, 2H), 4.05 ppm (m, 4H), 4.48 ppm (t, 3H), 5.56 ppm (s, 1H), 7.37 ppm (m, 5H).

Schematically, the reaction is represented as follows:

Compound 5-02

Compound 6-02

Compound 6-02 (14.2 g) was dissolved in a mixture of acetonitrile (80 ml) and distilled water (80 ml). Next, a 6% solution of NaOH was added to adjust the pH to 12.5. The solution was stirred for 5.5 hours at pH ranging from 12.3-12.8, which was maintained by periodical additions of a 6% solution of NaOH. NaCl (5 g) was added and the pH was adjusted to 7.5 with 5% $H_3PO_4$. The non-acidic impurities were extracted with $CH_2Cl_2$ (two treatments, a first using 300 ml and a second using 200 ml). The pH of the solution was adjusted to 3 with $H_3PO_4$ and the product was extracted with $CH_2Cl_2$ (two treatments, a first using 200 ml and a second using 100 ml).

The extract was dried ($MgSO_4$) and the solvent was distilled off under reduced pressure. The resulting product (Compound 7-02) had a yield of 8.7 g. NMR (d6-DMSO): 1.76 ppm (m, 2H), 2.31 ppm (t, 2H), 3.46 ppm (t, 2H), 4.05 ppm (m, 4H), 5.56 ppm (s, 1H), 7.37 ppm (m, 5H).

Schematically, the reaction is represented as follows:

Compound 6-02

Compound 7-02

Compound 7-02 (8.0 g) was dissolved in anhydrous methanol (120 ml) and upon dissolution, concentrated $H_2SO_4$ (1.6 ml) was added. The solution was stirred for 4 hours at room temperature. $NaHCO_3$ (8% solution) was added to adjust the pH of the mixture to 7.5. The product was extracted with $CH_2Cl_2$ (two treatments, each using 100 ml).

The extract was dried ($MgSO_4$) and volatile compounds were distilled off under reduced pressure (0.05 mm Hg) at 60° C. The resulting product (Compound 8-02) had a yield of 4.8 g. NMR ($d_6$-DMSO): 1.72 ppm (m, 2H), 2.37 ppm (t, 2H), 3.20 ppm (m, 1H), 3.42 ppm (bm, 4H), 3.49 ppm (t, 2H), 3.59 ppm (s, 3H), 4.46 ppm (t, 2H).

Schematically, the reaction is represented as follows:

Compound 7-02

Compound 8-02

Example 2

Preparation of "mPEG2$_{(40K)}$-Butanoic Acid, N-Hydroxysuccinimide Ester" or "mPEG-2-NHS"

(wherein mPEG$_{20K}$ designates a PEG having a molecular weight of 20,000 Daltons) "mPEG2$_{(40K)}$-Butanoic Acid, N-Hydroxysuccinimide Ester"

Activation of the hydroxyl groups in the precursor molecule. Compound 8-02 (2.0 g, 0.0208 equivalents) was dissolved in anhydrous acetonitrile (50 ml) and anhydrous pyridine (2.2 ml, 0.272 mole) and N,N-disuccinimidyl carbonate (5.86 g, 0.0229 mole, DSC) were added. The solution was stirred overnight at room temperature under argon atmosphere. Next, the mixture was filtered and the solvent was distilled off. The crude product was dissolved in $CH_2Cl_2$ (50 ml) and washed with a 5% $H_3PO_4$ solution. The solution was then dried ($MgSO_4$), and the solvent was distilled off. The resulting product (Compound 9-02) had a yield of 2.8 g. NMR ($d_6$-DMSO): 1.76 ppm (m, 2H), 2.35 ppm (t, 2H), 2.82 ppm (s, 8H), 3.56 ppm (t, 2H), 3.58 ppm (s, 3H), 3.96 ppm (m, 1H), 4.37 ppm (m, 2H), 4.52 ppm (m, 2H).

Schematically, the reaction is represented as follows:

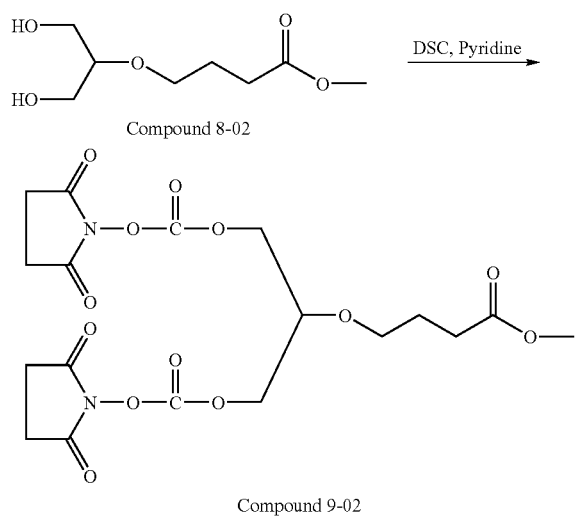

Coupling the activated precursor with an amine-containing water-soluble polymer. To a mixture of mPEG$_{(20K)}$-amine (11 g, 0.00055 mole) (Nektar Therapeutics, Huntsville, Ala.), acetonitrile (70 ml), and triethylamine (0.15 ml), compound 9-02 (0.119 g, 0.00050 equivalents) was added. The mixture was stirred for 3 hours at room temperature under argon atmosphere. Next, the solvent was distilled off under reduced pressure.

Schematically, the reaction is represented as follows:

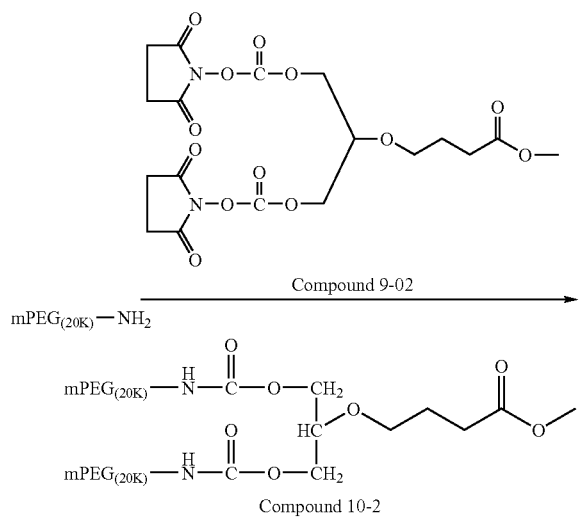

Deprotecting step and chromatographic purification of PEG2$_{(40K)}$-butanoic acid. The obtained Compound 10-2 (herein referred to as PEG2$_{(40K)}$-butanoic acid, methyl ester) was dissolved in 150 ml of distilled water and the pH of the solution was adjusted to 12.2 with a 5% NaOH solution. The solution was stirred for 1.5 hours at a pH in a range of 12.0-12.2. Next, NaCl (10 g) was added and the pH was adjusted to 2.5 with a 5% $H_3PO_4$ solution. The product was extracted with a $CH_2Cl_2$ treatment. The extract was dried ($MgSO_4$), and the solvent was distilled off under reduced pressure giving 9 g of solid product. Ion exchange chromatography: PEG2$_{(40K)}$-butanoic acid 85%, mPEG$_{(20K)}$ amine 10%. The product was purified by ion exchange chromatography as described in U.S. Pat. No. 5,932,462 giving 100% pure product. NMR ($d_6$-DMSO): 1.72 ppm (q, 2H) 2.24 ppm (t, 2H), 3.24 ppm (s, 6H), 3.51 ppm (s, PEG backbone), 3.99 ppm (m, 4H), 7.19 ppm (t, 2H).

Schematically, the reaction is represented as follows:

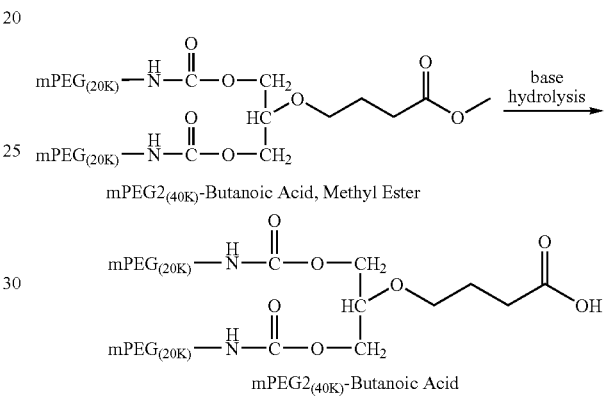

mPEG2$_{(40K)}$-butanoic acid can be used as a polymeric reagent for reactions to form polymer-active agent conjugates. In addition, mPEG2$_{(40K)}$-butanoic acid can be further reacted to provide polymeric reagents having functional groups other than a carboxylic acid. For example, preparation of the corresponding N-hydroxysuccinimide ester of the mPEG2$_{(40K)}$-butanoic acid as well as aldehyde, maleimide, and thiol derivatives are described below.

Preparation of mPEG2$_{(40K)}$-Butanoic Acid, N-Hydroxysuccinimide Ester

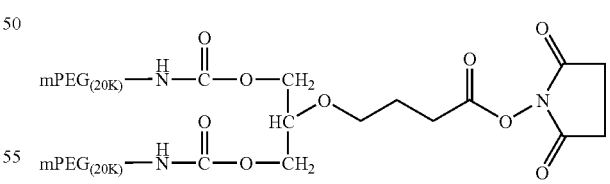

mPEG2$_{(40K)}$-butanoic acid (9.0 g, 0.000225 mole) (prepared as described above) was dissolved in anhydrous dichloromethane (70 ml) and N-hydroxysuccinimide (0.0285 g, 0.000248 mole) and 1,3-dicyclocarboimide (0.0510 g, 0.000247 mole) were added. The mixture was stirred overnight at room temperature under argon atmosphere. Next, part of the solvent was distilled off under reduced pressure and the product was precipitated with isopropyl alcohol at room temperature and dried under vacuum giving 8.6 g of white powder NMR ($d_6$-DMSO): 1.81 ppm (q, 2H) 2.70 ppm (t, 2H), 2.81 ppm (s, 4H), 3.24 ppm (s, 6H), 3.51 ppm (s, PEG backbone), 3.99 ppm (m, 4H), 7.22 ppm (t, 2H).

Example 3

Preparation of a "mPEG2$_{(40K)}$-Butyraldehyde" or "mPEG2-ButyrALD"

Preparation of Tetra(ethylene glycol) mono-butyraldehyde, diethyl acetal

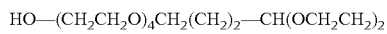

A mixture of tetra(ethylene glycol) (97.1 g, 0.500 moles) and toluene (200 ml) was azeotropically dried by distilling off toluene under reduced pressure (rotary evaporator). The dried tetra(ethylene glycol) was dissolved in anhydrous toluene (180 ml) and 1.0 M solution of potassium tert-butoxide in tert-butanol (120.0 ml, 0.120 moles) and 4-chlorobutyraldehyde diethyl acetal (18.1 g, 0.100 moles) (Alfa Aesar, Ward Hill, Mass.) were added. The mixture was stirred at 95-100° C. overnight under argon atmosphere. After cooling to room temperature, the mixture was filtered and the solvents were distilled off under reduced pressure. The crude product was dissolved in 1000 ml deionized water and the resulting solution was filtered through active carbon. Sodium chloride (100 g) was added and the product was extracted with dichloromethane (250, 200, and 150 ml). The extract was dried (over MgSO$_4$) and the solvent was distilled off under reduced pressure (by rotary evaporation).

The crude product was dissolved in 300 ml 10% phosphate buffer (pH=7.5) and impurities were extracted with ethyl acetate (2×50 ml). The resulting product was extracted with dichloromethane (200, 150, and 100 ml). The extract was dried (over MgSO$_4$) and the solvent was distilled off under reduced pressure (by rotary evaporation). Yield: 20.3 g. NMR (d$_6$-DMSO): 1.10 ppm (t, CH$_3$—C—) 1.51 ppm (m, C—CH$_2$—CH$_2$—), 3.49 ppm (bm, —OCH$_2$CH$_2$O—) 4.46 ppm (t, —CH, acetal), 4.58 ppm (t, —OH). Purity: ~100% (no signs of unreacted starting materials).

Preparation of Tetra(ethylene glycol)-α-mesylate-ω-butyraldehyde, diethyl acetal

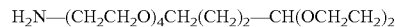

A mixture of tetra(ethylene glycol) mono-butyraldehyde, diethyl acetal (12.5 g, 0.037 moles) and toluene (120 ml) was azeotropically dried by distilling off toluene under reduced pressure (rotary evaporator). The dried tetra(ethylene glycol) mono-butyraldehyde, diethyl acetal was dissolved in anhydrous toluene (100 ml). To the solution was added 20 ml of anhydrous dichloromethane and 5.7 ml of triethylamine (0.041 moles). Then 4.5 g of methanesulfonyl chloride (0.039 moles) was added dropwise. The solution was stirred at room temperature under a nitrogen atmosphere overnight. Next sodium carbonate (5 g) was added, the mixture was stirred for one hour. The solution was then filtered and solvents were distilled off under reduced pressure (rotary evaporator). NMR (d$_6$-DMSO): 1.10 ppm (t, CH$_3$—C—) 1.51 ppm (m, C—CH$_2$—CH$_2$—), 3.17 ppm (s, CH$_3$— methanesulfonate), 3.49 ppm (bm, —OCH$_2$CH$_2$O—), 4.30 ppm (m, —CH$_2$—methanesulfonate), 4.46 ppm (t, —CH, acetal). Purity: ~100%.

Tetra(ethylene glycol)-α-amino-ω-butyraldehyde, diethyl acetal

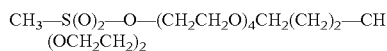

A mixture of tetra(ethylene glycol)-a-mesylate-co-butyraldehyde, diethyl acetal (14.0 g), concentrated ammonium hydroxide (650 ml), and ethyl alcohol (60 ml) was stirred for 42 hours at room temperature. Next, all volatile materials were distilled off under reduced pressure. The crude product was dissolved in 150 ml deionized water and the pH of the solution was adjusted to 12 with 1.0 M NaOH. The product was extracted with dichloromethane (3×100 ml). The extract was dried (MgSO$_4$) and the solvent was distilled off under reduced pressure (rotary evaporator). Yield 10.6 g. NMR (D$_2$O): 1.09 ppm (t, CH$_3$—C—) 1.56 ppm (m, C—CH$_2$—CH$_2$—), 2.69 ppm (t, CH$_2$—N), 3.56 ppm (bm, —OCH$_2$CH$_2$O—), 4.56 ppm (t, —CH, acetal). Purity: ~100%.

Branched mPEG2(40.3 KDa)-butyraldehyde, diethyl acetal

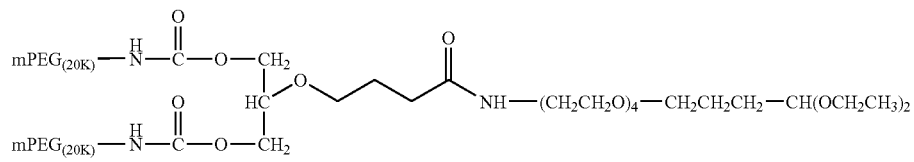

To a solution of mPEG2$_{(40K)}$-butanoic acid, N-hydroxysuccinimide ester (Example 2) (5.0 g, 0.000125 moles) in methylene chloride (100 ml), tetra(ethylene glycol)-α-amino-ω-butyraldehyde, diethyl acetal (0.050 g, 0.000148 moles) and triethylamine (0.035 ml) were added and the reaction mixture was stirred overnight at room temperature under an argon atmosphere. The solvent was evaporated to dryness using a rotary evaporator. The crude product was dissolved in methylene chloride and precipitated with isopropyl alcohol. The wet product was dried under reduced pressure. Yield 4.8 g. NMR (d$_6$-DMSO): 1.10 ppm (t, 6H), 1.51 ppm (m, 4H), 1.67 ppm (m, 2H), 2.12 ppm (t, 2H), 3.12 ppm (q, 4H), 3.24 ppm (s, 3H), 3.51 ppm (s, PEG backbone), 3.99 ppm(m, 4H), 4.46 ppm (t, 1H, acetal). 7.22 ppm (t, 2H), 7.82 ppm (t, 1H). Substitution: ~100%.

Branched mPEG2(40.3 KDa)-butyraldehyde

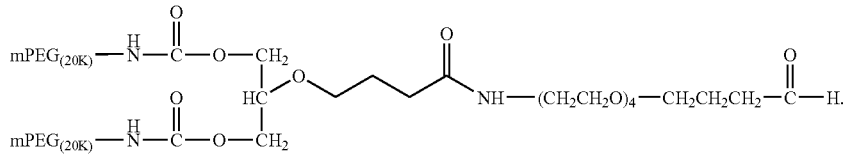

Branched PEG2(40.3 KDa)-butyraldehyde, diethyl acetal (4.8 g) was dissolved in 100 ml water and the pH of the solution was adjusted to 3 with diluted phosphoric acid. The solution was stirred for 3 hours at room temperature, followed by addition of 0.5 M sodium hydroxide sufficient to adjust the pH of the solution to about 7. The product (branched mPEG2 (40.3 KDa)-butyraldehyde) was extracted with methylene chloride, and the extract dried with anhydrous magnesium sulfate. The solvent was distilled off under reduced pressure. Yield 4.2 g. NMR (d$_6$-DMSO): 1.67 ppm (m, 2H), 1.76 ppm (p, —CH$_2$—CH$_2$—CHO—, 2H), 2.11 ppm (t, 2H), 2.44 ppm (dt, —CH$_2$—CHO), 3.24 ppm (s, —OCH$_3$, 6H), 3.51 ppm (s, PEG backbone), 3.99 ppm (m, 4H), 7.24 ppm (t, 2H), 7.83 ppm (t, 1H), 9.66 ppm (t, —CHO). Substitution: ~100%.

Example 4

Preparation of a "mPEG2$_{(40K)}$-Maleimide"

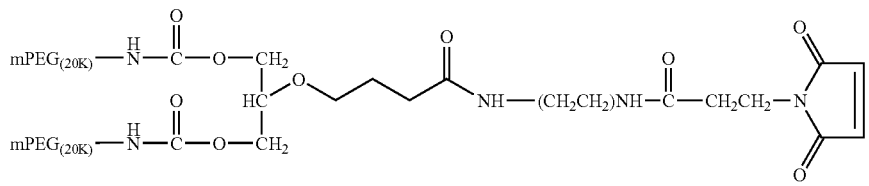

To a solution of mPEG2($_{40}$K)-butanoic acid, N-hydroxysuccinimide ester (Example 2) (5.0 g, 0.000125 moles) in anhydrous acetonitrile (100 ml), N-(3-maleimidepropionamido)ethylenediamide in a form of trifluoroacetic acid salt (0.042 g, 0.000129 moles) and triethylamine (0.050 ml) were added and the reaction mixture was stirred overnight at room temperature under an argon atmosphere. The solvent was evaporated to dryness using a rotary evaporator. The crude product was dissolved in small amount of methylene chloride and precipitated with isopropyl alcohol. The wet product was dried under reduced pressure. Yield 4.7 g. NMR (d$_6$-DMSO): 1.69 ppm (m, 2H), 2.09 ppm (t, 2H) 2.31 ppm (t, 2H), 3.03 ppm (q, 4H), 3.12 ppm (q, 4H), 3.24 ppm (s, 6H), 3.51 ppm (s, PEG backbone), 3.99 ppm (m, 4H), 7.00 ppm (s, 2H, maleimide), 7.21 ppm (t, 2H), 7.75 ppm (t, 1H), 7.96 ppm (t, 1H).

Example 5

Preparation of a "mPEG2$_{(40K)}$-Thiol"

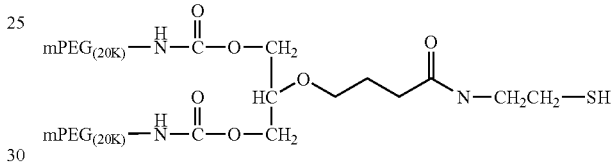

To a solution of mPEG2$_{(40K)}$-butanoic acid, N-hydroxysuccinimide ester (Example 2) (5.0 g, 0.000125 moles) in methylene chloride (50 ml), cystamine dihydrochloride (0.0142 g, 0.000126 equivalents) and triethylamine (0.040 ml) were added and the reaction mixture was stirred overnight at room temperature under an argon atmosphere. Next dithiothreitol (0.054 g, 0.000350 moles) and triethylamine (0.25 ml) were added and the mixture was stirred for 3 hours at room temperature under argon atmosphere. The solvent was evaporated to dryness using a rotary evaporator. The crude product was dissolved in small amount of methylene chloride and precipitated with isopropyl alcohol. The wet product was dried under reduced pressure. Yield 4.8 g. NMR (CDCl$_3$): 1.68 ppm (m, —SH, 1H), 1.35 ppm (t, 2H), 2.65 ppm (q, —CH$_2$SH, 2H), 3.15 ppm (q, 6H), 3.36 ppm (s, 6H), 3.65 ppm (s, PEG backbone), 4.15 ppm(m, 4H). Substitution: ~100%.

Example 6

Preparation of a "mPEG3$_{(60K)}$-Butanoic Acid, N-Hydroxysuccinimide Ester" with Pentaerythritol linker

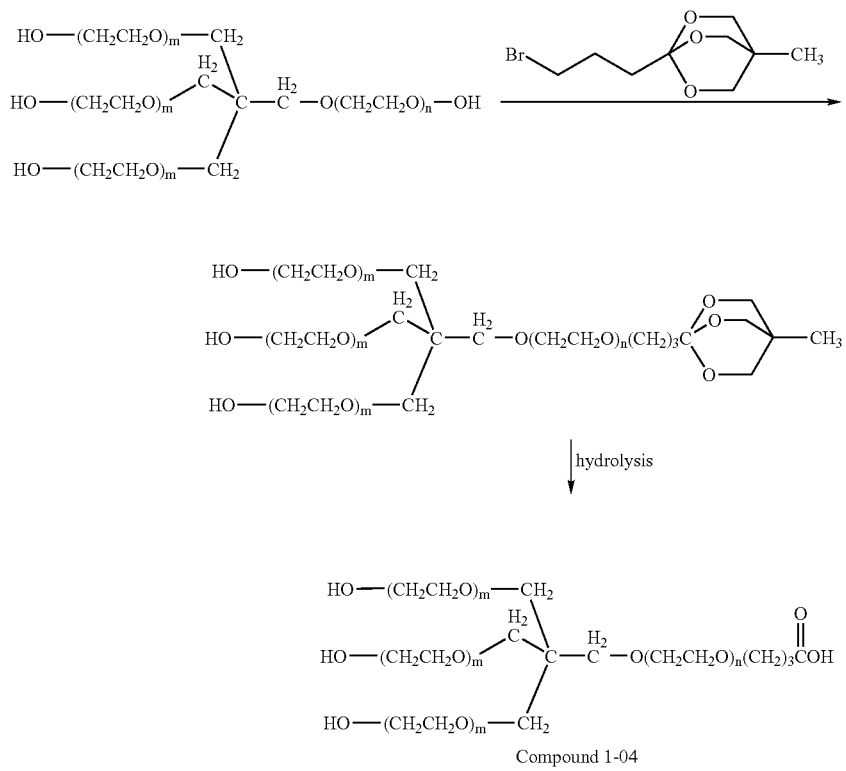

Compound 1-04

A mixture of pentaerythritol ethoxylate (15/4 EO/OH, Mn=797, Sigma-Aldrich) (100 g, 0.125 moles) and toluene (200 ml) was azeotropically dried by distilling off toluene under reduced pressure. The dried pentaerythritol ethoxylate was dissolved in anhydrous toluene (150 ml) and 1.0 M solution of potassium tert-butoxide in tert-butanol (30 ml, 0.03 moles) and 1-(3-bromopropyl)-4-methyl-2,6,7-trioxabicyclo[2,2,2]octane (6.3 g, 0.025 moles) were added. Next, the mixture was stirred at 80-85° C. overnight under an argon atmosphere. After cooling to room temperature, the mixture was filtered and the solvents were distilled off under reduced pressure. The crude product was dissolved in 800 ml deionized water. The pH of the solution was adjusted to 2 with 5% phosphoric acid and the solution was stirred for 15 minutes at room temperature. Next the pH was readjusted to 12 with 1M sodium hydroxide and the solution was stirred for 2 hours keeping the pH at 12 by periodical addition of 1M sodium hydroxide. Sodium chloride (40 g) was added and the unreacted pentaerythritol ethoxylate was extracted with dichloromethane. Next the pH was adjusted to 3 with 5% phosphoric acid and the product was extracted with dichloromethane. The extract was dried with anhydrous magnesium sulfate and the solvent was distilled off under reduced pressure. Yield 15 g. NMR (d$_6$-DMSO): 1.72 ppm (q, 2H) 2.24 ppm (t, 2H), 3.51 ppm (s, 60H), 4.57 ppm (t, 3H).

Preparation of Compound 2-04

Compound 2-04

Compound 1-04 (15 g, 0.017 moles) was dissolved in anhydrous methanol (300 ml) and concentrated sulfuric acid (4 ml) was added. The solution was stirred for 4 hours at room temperature. NaHCO$_3$ (8% solution) was added to adjust the pH of the mixture to 7.5. The product was extracted with CH$_2$Cl$_2$. The extract was dried (MgSO$_4$) and volatile compounds were distilled off under reduced pressure. Yield 13.5 g. NMR (d$_6$-DMSO): 1.72 ppm (q, 2H) 2.37 ppm (t, 2H), 3.51 ppm (s, 60H), 4.57 ppm (t, 3H).

Preparation of Compound 3-04

Compound 3-04

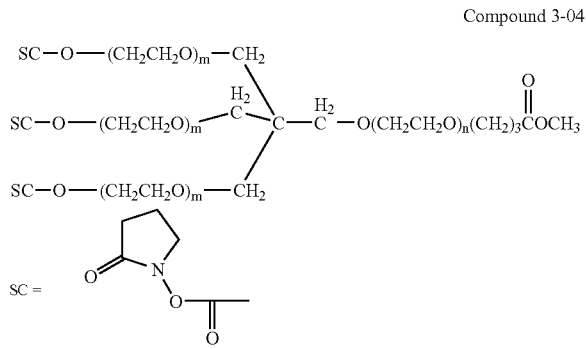

Compound 2-04 (13.5 g, 0.0444 equivalents) was dissolved in anhydrous acetonitrile (100 ml) and anhydrous pyridine (4.4 ml, 0.544 mole) and N,N-disuccinimidyl carbonate (12.40 g, 0.0484 mole) were added. The solution was stirred overnight at room temperature under an argon atmosphere. Next, the mixture was filtered and the solvent was distilled off. The crude product was dissolved in $CH_2Cl_2$ (200 ml) and washed with 5% $H_3PO_4$ solution. The solution was then dried ($MgSO_4$), and the solvent was distilled off. Yield 16.5 g. NMR ($d_6$-DMSO): 1.72 ppm (m, 2H), 2.37 ppm (t, 2H), 2.82 ppm (s, 12H), 3.50 ppm (s, 48H), 3.70 ppm (m, 6H), 4.45 (m, 6H).

Preparation of Compound 4-04, a (PEG3$_{(60K)}$-butanoic acid, methyl ester). To a mixture of mPEG$_{(20K)}$-amine (15 g, 0.00075 mole) (Nektar Therapeutics, Huntsville, Ala.), acetonitrile (70 ml), and triethylamine (0.15 ml), compound 3-04 (0.259 g, 0.00060 equivalents) was added. The mixture was stirred for three hours at room temperature under argon atmosphere. Next, the solvent was distilled off under reduced pressure.

Deprotecting step and chromatographic purification of a PEG3$_{(60K)}$-butanoic acid. Compound 4-04 (referred herein as "PEG3$_{(60K)}$-butanoic acid, methyl ester") was dissolved in 150 ml of distilled water and the pH of the solution was adjusted to 12.2 with a 5% NaOH solution. The solution was stirred for 1.5 hours at a pH in a range of 12.0-12.2. Next, NaCl (10 g) was added and the pH was adjusted to 2.5 with a 5% $H_3PO_4$ solution. The product was extracted with a $CH_2Cl_2$ treatment. The extract was dried ($MgSO_4$), and the solvent was distilled off under reduced pressure giving 13.8 g of solid product. Ion exchange chromatography: PEG3$_{(60K)}$-butanoic acid 82%, M-PEG$_{(20K)}$-amine 18%. The product was purified by ion exchange chromatography as described in U.S. Pat. No. 5,932,462 giving 100% pure product. NMR ($d_6$-DMSO): 1.72 ppm (q, 2H) 2.24 ppm (t, 2H), 3.24 ppm (s, 6H), 3.51 ppm (s, PEG backbone), 3.99 ppm (m, 6H), 7.19 ppm (t, 3H).

Preparation of mPEG3$_{(60K)}$-butanoic Acid, N-hydroxysuccinimide ester. The obtained mPEG3$_{(60K)}$-butanoic acid (previous step) (9.0 g, 0.000225 mole) was dissolved in anhydrous dichloromethane (70 ml) and N-hydroxysuccinimide (0.0285 g, 0.000248 mole) and 1,3-dicyclohexylcarbodiimide (0.0510 g, 0.000247 mole) were added. The mixture was stirred overnight at room temperature under an argon atmosphere. Next, part of the solvent was distilled off under reduced pressure and the product was precipitated with isopropyl alcohol at room temperature and dried under vacuum giving 8.6 g of white powder. NMR ($d_6$-DMSO): 1.81 ppm (q, 2H) 2.70 ppm (t, 2H), 2.81 ppm (s, 4H), 3.24 ppm (s, 6H), 3.51 ppm (s, PEG backbone), 3.99 ppm (m, 4H), 7.22 ppm (t, 2H).

Example 7

Preparation of a Monofunctional mPEG

A polymer of the invention comprising a single water-soluble polymer is prepared. The procedure of Example 2 is followed except that 3-hydroxy-propionic acid, methyl ester is replaced for compound 8-02.

3-hydroxy-propionic acid, methyl ester

The resulting compound ("mPEG-propionic acid, methyl ester") is found to have the following structure:

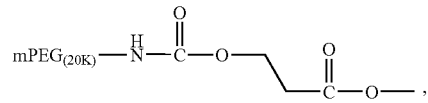

mPEG$_{(20K)}$-Propionic Acid, Methyl Ester mPEG$_{(20K)}$-propionic acid, methyl ester can provide the corresponding carboxylic acid. For example, the methyl ester can be dissolved in distilled water and the pH adjusted to about 12 using a NaOH solution. Thereafter, a salt such as sodium chloride can be added and the pH then adjusted to around 3 using a suitable acid. The corresponding carboxylic acid (mPEG$_{(20K)}$-propionic acid) can be extracted using a methylene chloride treatment, drying, and distilling off any remaining solvent.

The mPEG$_{(20K)}$-propionic acid can be used as a polymeric reagent for reactions to form polymer-active agent conjugates. In addition, mPEG$_{(20K)}$-propionic acid can be further reacted to provide polymeric reagents having functional groups other than a carboxylic acid. For example, using previously described techniques, the corresponding N-hydroxysuccinimide ester (see Example 2), aldehyde (see Example 3), maleimide (see Example 4), and thiol (see Example 5) derivatives of mPEG($_{20}$K) propionic acid can be prepared.

Example 8

Preparation of a Homobifunctional PEG

A homobifunctional polymer of the invention comprising a single water-soluble polymer portion is prepared. The procedure of Example 7 is followed except amine-PEG$_{(20K)}$-amine is substituted for mPEG$_{(20K)}$-amine. The resulting compound is found to have the following structure:

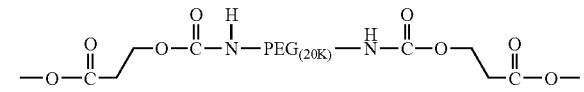

mPEG$_{(20K)}$-Propionic Acid, Methyl Ester (a difunctional polymer)

mPEG$_{(20K)}$-dipropionic acid, methyl ester can provide the corresponding dicarboxylic acid. For example, mPEG$_{(20K)}$-dipropionic acid, methyl ester can be dissolved in distilled water and the pH adjusted to about 12 using a NaOH solution. Thereafter, a salt such as sodium chloride can be added and the pH then adjusted to around 3 using a suitable acid. The corresponding dicarboxylic acid (mPEG$_{(20K)}$-dipropionic acid) can be extracted using a methylene chloride treatment, drying, and distilling off any remaining solvent.

The mPEG$_{(20K)}$-dipropionic acid can be used as a polymeric reagent for reactions to form polymer-active agent conjugates (comprising two active agents). In addition, mPEG$_{(20K)}$-dipropionic acid can be further reacted to provide polymeric reagents having functional groups other than a carboxylic acid. For example, using previously described techniques, the corresponding diN-hydroxysuccinimide ester (see Example 2), dialdehyde (see Example 3), dimaleimide (see Example 4), and dithiol (see Example 5) derivatives of mPEG$_{(20K)}$propionic acid can be prepared.

Example 9

Conjugation mPEG2$_{(40K)}$-maleimide (Example 4) having a sulfhydryl-selective reactive group, is reacted with each of the polypeptide sequences as provided in SEQ. ID. NOS. 1-226.

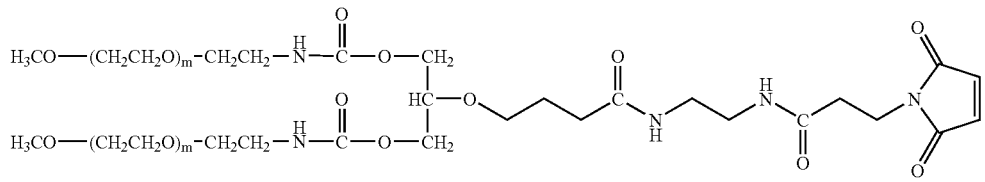

wherein (m), in the above structure, is about 454 and/or the molecular weight of each water-soluble polymer is about 20,000 Daltons, thereby providing a reagent having a molecular weight of about 40,000 Daltons.

To the extent that any particular polypeptide lacks a sulfhydryl group (e.g., the polypeptide lacks both methionine and a cysteine residue), a methionine or a cysteine residue can be added to the polypeptide using conventional synthetic techniques. See, for example, WO 90/12874.

For each polypeptide, an excess of polymer is added to a reaction vessel containing the polypeptide. The reaction conditions include a pH of from about 7 to about 8 at room temperature. After about five hours, a conjugate of the polypeptide and the polymer is produced.

Example 10

Multiarmed Polymer

A multiarmed polymer comprising at least one reactive group is prepared as follows.

Three equivalents of carbonic acid bis-(2,5-dioxo-pyrrolidin-1yl)ester are combined with methyl-D-glucopyranoside in triethylamine to yield a first intermediate, as show below:

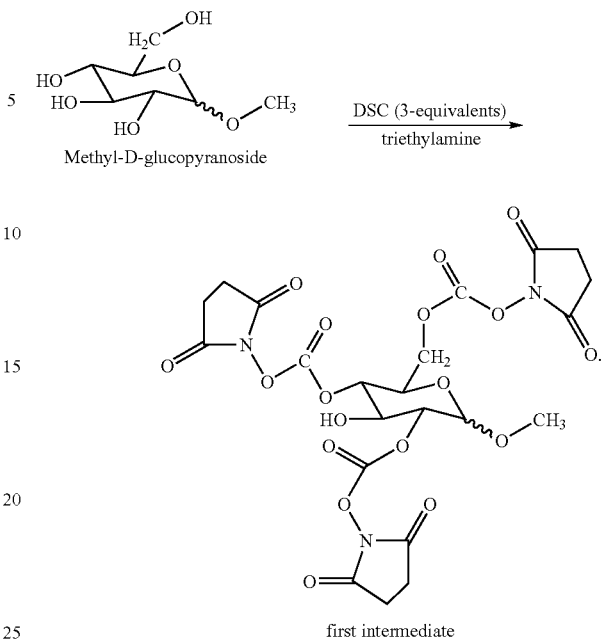

first intermediate

The first intermediate is then exposed to a slight excess of mPEG$_{(10K)}$-amine in the presence of triethylamine to yield a second intermediate, as shown below:

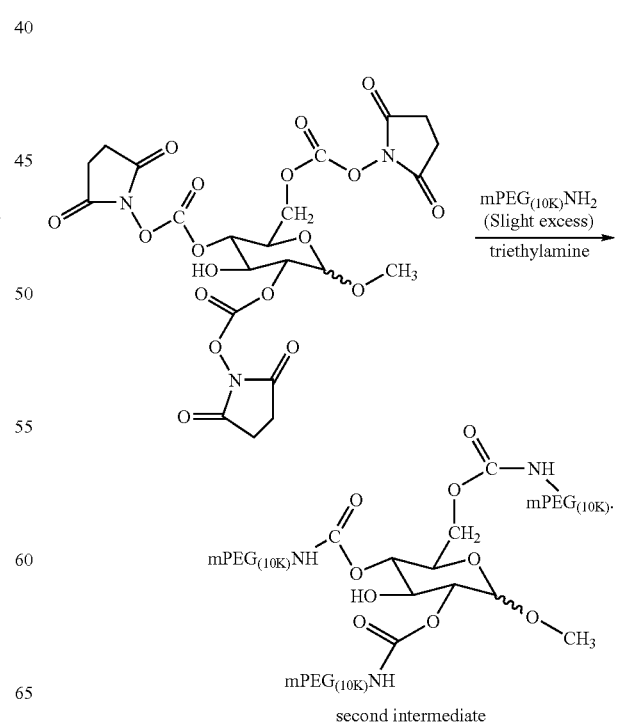

second intermediate

The second intermediate is then subjected to acid-catalyzed hydrolysis to yield the aldehyde and hemiacetal forms, as shown below:

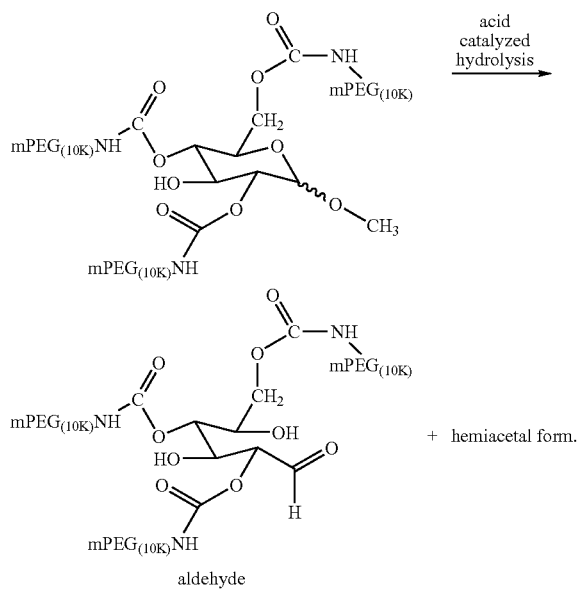

aldehyde

The aldehyde is comprised of three, 10K PEGs, thereby providing an overall 30K branched structure. The aldehyde, in turn, is optionally converted into other derivatives through the acid (e.g., the carboxylic acid formed when the aldehyde is exposed to mild oxidative conditions).

The approach can be used to provide two arms as well as four arms.

During any given procedure, mixtures of the substances (e.g., doubly substituted and some quadruply substituted) can be produced. In addition, positional isomers of any of the polymers are possible.

Example 11

Preparation of Polymer-EPO Conjugate-Random PEGylation of EPO

Recombinant erythropoietin, "EPO" (produced in *E. coli*, mammalian cells such as Chinese hamster ovary cells, or another source) is coupled to a branched mPEG2(40 KDa)-butyraldehyde (prepared as described in Example 3).

EPO (~2 mg) is dissolved in 1 ml of 50 mM phosphate buffer (pH 7.6) and branched PEG2(40 KDa)-butyraldehyde is added at 5× the molar EPO concentration. A reducing agent, NaCNBH$_3$, is added and the solution stirred for 24 hours at room temperature to couple the branched PEG2(40 KDa)-butyraldehyde reagent to the protein via an amine linkage.

The reaction mixture is analyzed by SDS-PAGE to determine the degree of conjugation. Confirmation of the degree of conjugation is done by Matrix Assisted Laser Desorption Ionization Time-of-Flight (MALDI-TOF) mass spectrometry. The displayed peaks for native and monoconjugated species differ by approximately 40,000 Daltons. The resulting reaction mixture contains a mixture of native and monoconjugated protein. Increasing the ratio of PEG reagent to protein increases the degree of conjugation.

The above demonstrates random PEGylation of an illustrative protein of the invention to yield a distribution of PEGylated EPO products. If desired, the reaction mixture can be further separated to isolate the individual isomers as described below.

PEG conjugates having different molecular weights are separated by gel filtration chromatography. The different PEG conjugates are fractionated on the basis of their different molecular weights (in this case, varying by approximately 40,000 Daltons). Specifically, the separation is performed by using a serial column system suitable for effective separation of products in the molecular weight range observed, e.g., a Superdex™200 column (Amersham Biosciences). The products are eluted with 10 ml acetate buffer at a flow rate of 1.5 ml/min. The collected fractions (1 ml) are analyzed by OD at 280 nm for protein content and also using an iodine test for PEG content (Sims et al. (1980) *Anal. Biochem.* 107:60-63). In addition, the results can be visualized by running an SDS PAGE gel, followed by staining with barium iodide. Fractions corresponding to the eluted peaks are collected, concentrated by ultrafiltration using a membrane, and lyophilized. This method results in separation/purification of conjugates having the same molecular weights but does not provide separation of conjugates having the same molecular weight but different PEGylation sites (i.e., positional isomers).

Separation of positional isomers is carried out by reverse phase chromatography using an RP-HPLC C18 column (Amersham Biosciences or Vydac). This procedure is effective for separating PEG-biomolecule isomers having the same molecular weight (positional isomers). The reverse-phase chromatography is carried out using a RP-HPLC C18 preparative column and eluted with a gradient of water/0.05% TFA (Eluent A) and acetonitrile/0.05% TFA (Eluent B).

Fractions corresponding to the eluted peaks are collected, evaporated to eliminate acetonitrile and TFA, followed by removal of solvent to isolate the individual positional PEG-isomers.

This example demonstrates the ability of the polymeric reagents of the invention to be used in forming conjugates of EPO.

Example 12

Preparation of Polymer-EPO Conjugate—N-Terminal PEGylation of EPO

Recombinant erythropoietin, "EPO" (produced in *E. coli*, mammalian cells such as Chinese hamster ovary cells, or another source) is coupled to branched mPEG2(40 KDa)-butyraldehyde (prepared as described in Example 3).

EPO (~2 mg) is dissolved in 1 ml of 0.1 mM sodium acetate (pH 5) and mPEG2(40 KDa)-butyraldehyde is added at 5× the molar EPO concentration. A reducing agent, NaCNBH$_3$, is added and the solution is stirred for 24 hours at 4° C. to couple the mPEG2(40 KDa)-butyraldehyde reagent to the protein via an amine linkage.

The reaction mixture is analyzed by SDS-PAGE to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugated species differ by approximately 40,000 Daltons. The resulting reaction mixture primarily contains a mixture of native and monoconjugated protein. The monoconjugated species are purified by column chromatography to remove free EPO and higher molecular weight species.

Confirmation of N-terminal PEGylation is carried out by peptide mapping. Increasing the ratio of PEG to protein increases the degree of PEGylation, yielding polyconjugated protein.

The above demonstrates PEGylation of an illustrative protein of the invention to yield a predominantly N-terminal single PEGylated protein.

This example demonstrates the ability of the polymeric reagents of the invention to be used in forming conjugates of EPO.

Example 13

N-Terminal PEGylation of GCSF

Recombinant granulocyte colony stimulating factor, "GCSF" (produced in E. coli, mammalian cells such as Chinese hamster ovary cells, or another source) is coupled to mPEG2(40 KDa)-butyraldehyde (prepared as described in Example 3).

GCSF (~2. mg) is dissolved in 1 ml of 0.1 mM sodium acetate (pH 5) and mPEG2(40 KDa)-butyraldehyde is added at 5× the molar GCSF concentration. The reducing agent, NaCNBH$_3$, is added and the solution stirred for 24 hours at 4° C. to couple the mPEG2(40 KDa)-butyraldehyde reagent to the protein via an amine linkage.

The resulting reaction mixture is analyzed by SDS-PAGE to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugated species differ by approximately 40,000 Daltons. The resulting reaction mixture primarily contains a mixture of native and monoconjugated GCSF. The monoconjugated are purified by column chromatography to remove free GCSF and higher molecular weight species. Confirmation of N-terminal PEGylation is conducted by peptide mapping. Increasing the ratio of PEG to protein increases the degree of conjugation yielding polyconjugated protein.

This example demonstrates the ability of the polymeric reagents of the invention to be used in forming conjugates of GCSF.

Example 14

N-Terminal PEGylation of Interferon-α

Recombinant interferon-alfa, "IFN-α" (produced in E. coli, mammalian cells such as Chinese hamster ovary cells, or another source) is coupled to mPEG2(40 KDa)-butyraldehyde (prepared as described in Example 3).

IFN-α (~2. mg) is dissolved in 1 ml of 0.1 mM sodium acetate (pH 5) and mPEG2(40 KDa)-butyraldehyde is added at 5× the molar IFN-α concentration. A reducing agent, NaCNBH$_3$, is added and the solution stirred for 24 hours at 4° C. to couple the mPEG2(40 KDa)-butyraldehyde reagent to the protein via an amine linkage.

The reaction mixture is analyzed by SDS-PAGE to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugated species differ by approximately 40,000 Daltons. The resulting reaction mixture primarily contains a mixture of native and monoconjugated protein. The monoconjugated species are purified by column chromatography to remove free interferon-α and higher molecular weight species. Confirmation of N-terminal PEGylation is conducted by peptide mapping. Increasing the ratio of PEG to protein increases the degree of conjugation yielding polyconjugated IFN-α.

This example demonstrates the ability of the polymeric reagents of the invention to be used in forming conjugates of IFN-α.

Example 15

N-Terminal PEGylation of Human Growth Hormone

Recombinant human growth hormone, "hGH" (produced in E. coli, mammalian cells such as Chinese hamster ovary cells, or another source) is coupled to mPEG2(40 KDa)-butyraldehyde (prepared as described in Example 3).

hGH (~2 mg) is dissolved in 1 ml of 0.1 mM sodium acetate (pH 5) and mPEG2(40 KDa)-butyraldehyde is added at 5× the molar hGH concentration. A 5- to 20-fold molar excess of the reducing agent, NaCNBH$_3$, is added and the solution is stirred for 24 hours at 4° C. to couple the mPEG2(40 KDa)-butyraldehyde reagent to the protein via an amine linkage.

Progress of the reaction is analyzed by SDS-PAGE or MALDI-TOF mass spectrometry to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugated and other species differ by approximately 40,000 Daltons. The resulting reaction mixture primarily contains a mixture of native and monoconjugated protein. The monoconjugated species are purified by column chromatography to remove free hGH and higher molecular weight species. Confirmation of N-terminal conjugation is conducted by peptide mapping. Increasing the ratio of mPEG2(40 KDa)-butyraldehyde to protein increases the degree of conjugation yielding a population of polyconjugated hGH.

This example demonstrates the ability of the polymeric reagents of the invention to be used in forming conjugates of hGH.

Example 16

N-Terminal PEGylation of Interferon-β

Recombinant interferon-β, "IFN-β" (produced in E. coli, mammalian cells such as Chinese hamster ovary cells, or another source) is coupled to mPEG2(40 KDa)-butyraldehyde (prepared as described in Example 3).

IFN-β (~2 mg) is dissolved in 1 ml of 0.1 mM sodium acetate (pH 5) and mPEG2(40 KDa)-butyraldehyde is added at 5× the molar IFN-β concentration. A 5- to 20-fold molar excess of the reducing agent, NaCNBH$_3$, is added and the solution is stirred for 24 hours at 4° C. to couple the mPEG2 (40 KDa)-butyraldehyde reagent to the protein via an amine linkage.

Progress of the reaction is analyzed by SDS-PAGE or MALDI-TOF mass spectrometry to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugated species differ by approximately 40,000 Daltons. The resulting reaction mixture primarily contains a mixture of native and monoconjugated protein. The monoconjugated species are purified by column chromatography to remove free IFN-β and higher molecular weight species. Confirmation of N-terminal PEGylation is conducted by peptide mapping. Increasing the ratio of mPEG2(40 KDa)-butyraldehyde to protein increases the degree of conjugation yielding a population of polyconjugated IFN-β.

This example demonstrates the ability of the polymeric reagents of the invention to be used in forming conjugates of IFN-β.

Example 17

N-Terminal PEGylation of FSH

Recombinant follicle stimulating hormone, "FSH" (produced in *E. coli*, mammalian cells such as Chinese hamster ovary cells, or another source) is coupled to mPEG2(40 KDa)-butyraldehyde (prepared as described in Example 3).

FSH (~2 mg) is dissolved in 1 mL of 0.1 mM sodium acetate (pH 5) and mPEG2(40 KDa)-butyraldehyde is added at 5× the molar FSH concentration. A 5- to 20-fold molar excess of the reducing agent, $NaCNBH_3$, is added and the solution is stirred for 24 hour at 4° C. to couple the mPEG2(40 KDa)-butyraldehyde reagent to the protein via an amine linkage.

Progress of the reaction is analyzed by SDS-PAGE or MALDI-TOF mass spectrometry to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugation and other species differ by approximately 40,000 Daltons. The resulting reaction mixture primarily contains a mixture of native and monoconjugated protein. The monoconjugation species are purified by column chromatography to remove free FSH and higher molecular weight species. Confirmation of N-terminal PEGylation is conducted by peptide mapping. Increasing the ratio of mPEG2(40 KDa)-butyraldehyde to protein increases the degree of conjugation yielding a population of polyconjugated FSH.

This example demonstrates the ability of the polymeric reagents of the invention to be used in forming conjugates of FSH.

Example 18

N-Terminal PEGylation of Factor VIII

Recombinant Factor VIII, "F8" (produced in *E. coli*, mammalian cells such as Chinese hamster ovary cells, or another source) is coupled to mPEG2(40 KDa)-butyraldehyde (prepared as described in Example 3).

F8 (~2 mg) is dissolved in 1 mL of 0.1 mM sodium acetate (pH 5) and mPEG2(40 KDa)-butyraldehyde is added at 5× the molar F8 concentration. A 5- to 20-fold molar excess of the reducing agent, $NaCNBH_3$, is added and the solution is stirred for 24 hour at 4° C. to couple the mPEG2(40 KDa)-butyraldehyde reagent to the protein via an amine linkage.

Progress of the reaction is analyzed by SDS-PAGE or MALDI-TOF mass spectrometry to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugation and other species differ by approximately 40,000 Daltons. The resulting reaction mixture primarily contains a mixture of native and monoconjugated protein. The monoconjugation species are purified by column chromatography to remove free F8 and higher molecular weight species. Confirmation of N-terminal PEGylation is conducted by peptide mapping. Increasing the ratio of mPEG2(40 KDa)-butyraldehyde to protein increases the degree of conjugation yielding a population of polyconjugated F8.

This example demonstrates the ability of the polymeric reagents of the invention to be used in forming conjugates of F8.

Example 19

N-Terminal PEGylation of B-Domain Deleted Factor VIII

Recombinant B-domain deleted Factor VIII, "BDD F8" (produced in *E. coli*, mammalian cells such as Chinese hamster ovary cells, or another source) is coupled to mPEG2(40 KDa)-butyraldehyde (prepared as described in Example 3).

BDD F8 (~2 mg) is dissolved in 1 mL of 0.1 mM sodium acetate (pH 5) and mPEG2(40 KDa)-butyraldehyde is added at 5× the molar BDD F8 concentration. A 5- to 20-fold molar excess of the reducing agent, $NaCNBH_3$, is added and the solution is stirred for 24 hour at 4° C. to couple the mPEG2(40 KDa)-butyraldehyde reagent to the protein via an amine linkage.

Progress of the reaction is analyzed by SDS-PAGE or MALDI-TOF mass spectrometry to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugation and other species differ by approximately 40,000 Daltons. The resulting reaction mixture primarily contains a mixture of native and monoconjugated protein. The monoconjugation species are purified by column chromatography to remove free BDD F8 and higher molecular weight species. Confirmation of N-terminal PEGylation is conducted by peptide mapping. Increasing the ratio of mPEG2(40 KDa)-butyraldehyde to protein increases the degree of conjugation yielding a population of polyconjugated BDD F8.

This example demonstrates the ability of the polymeric reagents of the invention to be used in forming conjugates of BDD F8.

Example 20

PEGylation of Factor VIII Using $mPEG2_{(40K)}$-Butanoic Acid, N-Hydroxysuccinimide Ester Recombinant Factor VIII, "F8" (produced in *E. coli*, mammalian cells such as Chinese hamster ovary cells, or another source) is coupled to $mPEG2_{(40K)}$-butanoic acid, N-hydroxysuccinimide ester (prepared as described in Example 2).

F8 is dissolved in an aqueous liquid and $mPEG2_{(40K)}$-butanoic acid, N-hydroxysuccinimide ester is added at one to ten times the molar F8 concentration to form a reaction solution. The pH of the reaction solution is adjusted to around 8 to 9.5 and the temperature is maintained at room temperature. The reaction solution is stirred for several hours to allow for coupling of the polymeric reagent to F8 via an amide linkage. Upon testing of the reaction solution, it is determined that conjugation has occurred at both N-terminal and lysine sites.

This example demonstrates the ability of the polymeric reagents of the invention to be used in forming conjugates of F8.

Example 21

PEGylation of B-Domain Deleted Factor VIII Using mPEG2$_{(40K)}$-Butanoic Acid, N-Hydroxysuccinimide Ester Recombinant B-domain deleted Factor VIII, "BDD F8" (produced in *E. coli*, mammalian cells such as Chinese hamster ovary cells, or another source) is coupled to mPEG2$_{(40K)}$-butanoic acid, N-hydroxysuccinimide ester (prepared as described in Example 2).

BDD F8 is dissolved in an aqueous liquid and mPEG2$_{(40K)}$-butanoic acid, N-hydroxysuccinimide ester is added at one to ten times the molar F8 concentration to form a reaction solution. The pH of the reaction solution is adjusted to around 8 to 9.5 and the temperature is maintained at room temperature. The reaction solution is stirred for several hours to allow for coupling of the polymeric reagent to BDD F8 via an amide linkage. Upon testing of the reaction solution, it is determined that conjugation has occurred at both N-terminal and lysine sites.

This example demonstrates the ability of the polymeric reagents of the invention to be used in forming conjugates of BDD F8.

Example 22

N-Terminal PEGylation of Desmopressin

Desmopressin is coupled to mPEG2(40 KDa)-butyraldehyde (prepared as described in Example 3).

Desmopressin (~2 mg) is dissolved in 1 mL of 0.1 mM sodium acetate (pH 5) and mPEG2(40 KDa)-butyraldehyde is added at 5× the molar BDD F8 concentration. A 5- to 20-fold molar excess of the reducing agent, NaCNBH$_3$, is added and the solution is stirred for 24 hour at 4° C. to couple the mPEG2(40 KDa)-butyraldehyde reagent to the protein via an amine linkage.

Progress of the reaction is analyzed by SDS-PAGE or MALDI-TOF mass spectrometry to determine the degree of conjugation. Confirmation of the degree of conjugation is carried out by Matrix Assisted Laser Desorption Ionization Time-of-Flight (MALDI-TOF) mass spectrometry. The displayed peaks for native and monoconjugation and other species differ by approximately 40,000 Daltons. The resulting reaction mixture primarily contains a mixture of native and monoconjugated protein. The monoconjugation species are purified by column chromatography to remove free desmopressin and higher molecular weight species. Confirmation of N-terminal PEGylation is conducted by peptide mapping. Increasing the ratio of mPEG2(40 KDa)-butyraldehyde to protein increases the degree of conjugation yielding a population of polyconjugated desmopressin.

This example demonstrates the ability of the polymeric reagents of the invention to be used in forming conjugates of desmorpessin.

Example 23

PEGylation of Desmopressin Using mPEG2$_{(40K)}$-Butanoic Acid, N-Hydroxysuccinimide Ester Desmopressin is coupled to mPEG2$_{(40K)}$-butanoic acid, N-hydroxysuccinimide ester (prepared as described in Example 2).

Desmopressin is dissolved in an aqueous liquid and mPEG2$_{(40K)}$-butanoic acid, N-hydroxysuccinimide ester is added at one to ten times the molar desmopressin concentration to form a reaction solution. The pH of the reaction solution is adjusted to around 8 to 9.5 and the temperature is maintained at room temperature. The reaction solution is stirred for several hours to allow for coupling of the polymeric reagent to desmopressin via an amide linkage. Upon testing of the reaction solution, it is determined that conjugation has occurred.

Example 24

PEGylation of Amdoxivir (DAPD)

Amdoxivir (DAPD) is coupled to mPEG2(40 KDa)-butyraldehyde (prepared as described in Example 3).

Amdoxivir (~2 mg) is dissolved in 1 mL of 0.1 mM sodium acetate (pH 5) and mPEG2(40 KDa)-butyraldehyde is added at 5× the molar amdoxivir concentration. A 5- to 20-fold molar excess of the reducing agent, NaCNBH$_3$, is added and the solution is stirred for 24 hour at 4° C. to couple the mPEG2(40 KDa)-butyraldehyde reagent to the protein via an amine linkage.

Progress of the reaction is analyzed by SDS-PAGE or MALDI-TOF mass spectrometry.

This example demonstrates the ability of the polymeric reagents of the invention to be used in forming conjugates of amdoxivir.

Example 25

PEGylation of Amdoxivir (DAPD) Using mPEG2$_{(40K)}$-Butanoic Acid, N-Hydroxysuccinimide Ester Amdoxivir (DAPD) is coupled to mPEG2$_{(40K)}$-butanoic acid, N-hydroxysuccinimide ester (prepared as described in Example 2).

Amdoxivir is dissolved in an aqueous liquid and mPEG2$_{(40K)}$-butanoic acid, N-hydroxysuccinimide ester is added at one to ten times the molar amdoxivir concentration to form a reaction solution. The pH of the reaction solution is adjusted to around 8 to 9.5 and the temperature is maintained at room temperature. The reaction solution is stirred for several hours to allow for coupling of the polymeric reagent to amdoxivir via an amide linkage. Upon testing of the reaction solution, it is determined that conjugation has occurred.

This example demonstrates the ability of the polymeric reagents of the invention to be used in forming conjugates of amdoxivir.

Example 26

PEGylation of hGH with Branched mPEG-N-Hydroxysuccinimide Derivative, 40 kDa

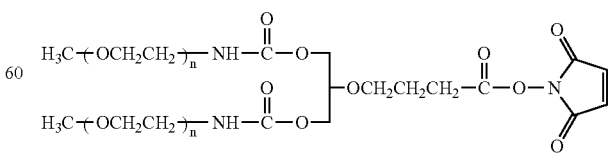

Branched mPEG-N-Hydroxysuccinimide Derivative, 40kDa, ("mPEG-2-NHS")

Native, recombinant human growth hormone ("hGH") was used in Examples 26 and 27. The hGH stock solution contained sodium phosphate buffer (pH 7.2) at a concentration of 7 mg/mL. Conjugation reactions were quenched with Tris [Tris(hydroxyl methyl) amino methane]. SDS-PAGE analysis of certain samples was analyzed by sodium dodecyl sulfate-polyacrylamide gel electrophoresis using a Bio-Rad system (Mini-PROTEAN III Precast Gel Electrophoresis System). Samples are mixed with sample buffer. Then, the prepared samples are loaded onto a gel and run for approximately thirty minutes. Anion Exchange Chromatograhy was carried out using a Hitrap Q Sepharose FF anion exchange column (5 ml, Amersham Biosciences) with the AKTAprime system (Amersham Biosciences) to purify the PEG-hGH conjugates of Examples 26 and 27. For each conjugate solution prepared, the conjugate solution was loaded on a column that was pre-equilibrated in 20 mM Tris buffer, pH 7.5 (buffer A) and then washed with nine column volumes of buffer A to remove any unreacted PEG reagent. Subsequently, a gradient of buffer A with 0-100% buffer B (20 mM Tris with 0.5 M NaCl buffer pH 7.5) was raised. The eluent was monitored by UV detector at 280 nm. Any higher-mers (e.g., 3-mers, 4-mers, and so forth) and 2-mers were eluted first, followed by 1-mers, and finally the unconjugated hGH. The fractions hGH or diPEGylated) species. The total percentages in FIG. 2A do not add to 100% due to rounding.

Anion-exchange chromatography was used to purify the conjugates. FIG. 2B shows the chromatogram following anion-exchange purification. The conjugate fractions were collected and analyzed by SEC-HPLC. The purified 1-mer, mono(mPEG-2-NHS-40k) hGH, (MW: 65 kDa, per MALDI-TOF), was shown to be 98% pure (FIG. 2C), while the purified 2-mer, di(mPEG-2-NHS-40k) hGH (MW: 108 kDa, per MALDI-TOF), was shown to be 93% pure (FIG. 2D).

mPEG-2-NHS provided a relatively large molecular volume of active N-hydroxysuccinimide ("NHS") ester, which selectively reacted with lysine and terminal amines. This is because the PEGylation reaction was carried out at pH 6.7 to 6.8, which favors N-terminal directed modification in conjunction with internal lysine modification.

Using this same approach, other conjugates can be prepared using mPEG-2-NHS having other weight average molecular weights.

Example 27

PEGylation of hGH with Branched mPEG-Butyraldehyde Derivative, 40 kDa

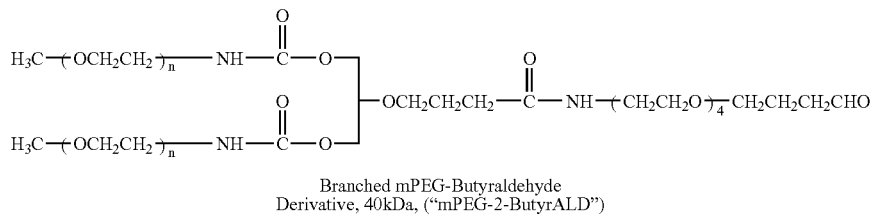

Figure 5:
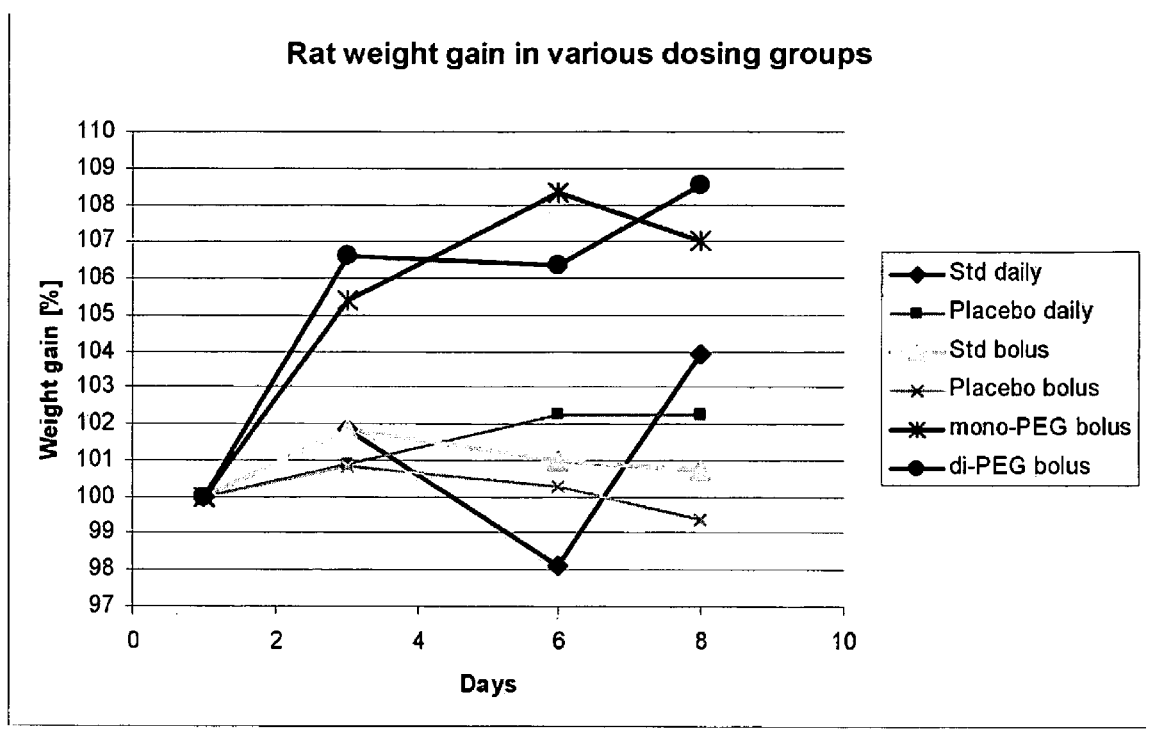
FIG. 5 is a plot demonstrating weight gain in rats over an eight day time course for six different groups dosed with either hGH, mono(mPEG-2-NHS-40k) hGH, di(mPEG-2-NHS-40k) hGH, or placebo, in different dosing regimens as described in Example 30.

Branched mPEG-Butyraldehyde
Derivative, 40kDa, ("mPEG-2-ButyrALD")

were pooled and the purity of the individual conjugate was determined by SEC-HPLC (FIG. 5). SEC-HPLC Analysis (size-exclusion chromatography) was performed on certain samples using an Agilent 1100 HPLC system (Agilent). Samples were analyzed using a Shodex protein KW-804 column (300×8 mm, Phenomenex), and a mobile phase consisting of 90% phosphate buffered saline and 10% ethanol, pH 7.4. The flow rate for the column was 0.5 ml/min. Eluted protein and PEG-protein conjugates were detected using UV at 280 nm.

mPEG-2-NHS, 40 kDa, stored at −20° C. under argon, was warmed to ambient temperature. A five-fold excess (relative to the amount of hGH in a measured aliquot of the stock hGH solution) of the warmed mPEG-2-NHS was dissolved in 10 mM sodium phosphate (pH 4.9) to form a 10% reagent solution. The 10% reagent solution was quickly added to the aliquot of stock hGH solution and nixed well. After the addition of the mPEG-2-NHS, the pH of the reaction mixture was determined and adjusted to 6.7 to 6.8 using conventional techniques. To allow for coupling of the mPEG-2-NHS to hGH via an amide linkage, the reaction solution was stirred for five hours at room temperature in the dark, thereby resulting in a conjugate solution. The reaction was quenched with Tris buffer. The conjugate solution was characterized.

Lane 2 in FIG. 1 shows the SDS-PAGE analysis of this conjugate solution.

Figure 2A:
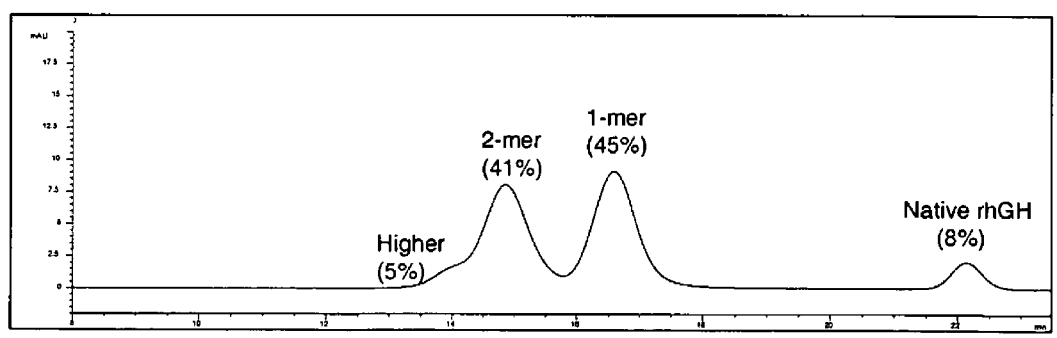
FIGS. 2A-2D correspond to the following chromatograms.
Figure 2B:
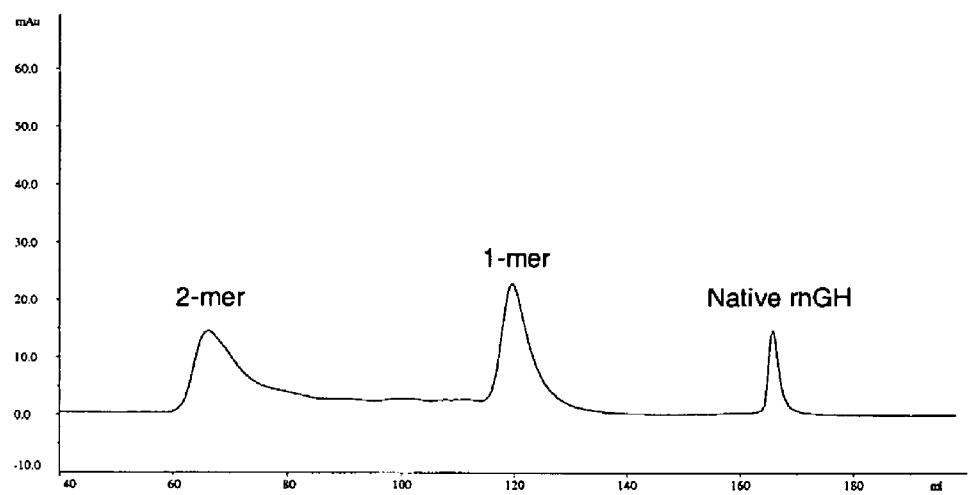
Figure 2C:
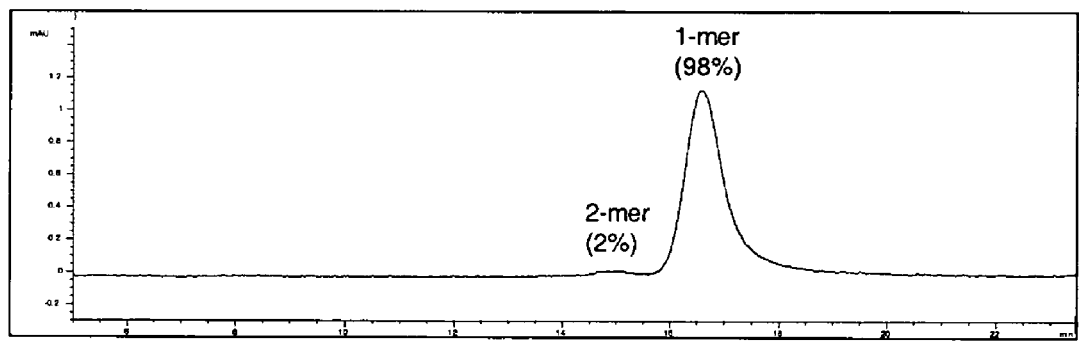
Figure 2D:
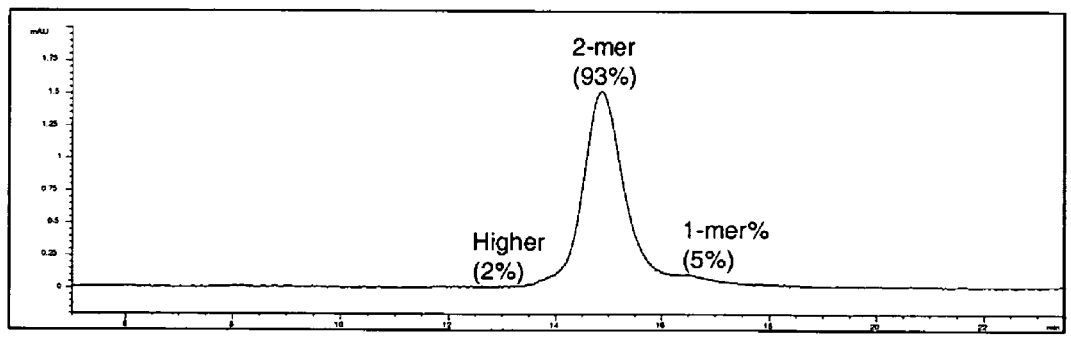

FIG. 2A shows the chromatogram following the SEC-HPLC analysis of the conjugate reaction mixture. The PEGylation reaction yielded 45% 1-mer (one PEG attached to hGH or monoPEGylated) and 41% 2-mer (two PEGs attached to mPEG-ButyrALD, 40 kDa, stored at −20° C. under argon, was warmed to ambient temperature. A ten-fold excess (relative to the amount of hGH in a measured aliquot of the stock hGH solution) of the warmed mPEG-ButryALD was dissolved in 10 mM sodium phosphate (pH 7.2) to form a 10% reagent solution. The 10% reagent solution was quickly added to the stock hGH solution and mixed well. After the addition of the mPEG2-ButryALD, the pH of the reaction mixture was determined and adjusted to 7.2 to 7.3 using conventional techniques, followed by mixing for thirty minutes. A reducing agent, sodium cyanoborohydride (NaCNBH$_3$), was added at about seventy molar excess relative to the hGH (with the pH tested and adjusted using conventional techniques to ensure a pH of about 7.2 to 7.3). To allow for coupling of the mPEG2-ButryALD to hGH via a secondary amine linkage, the reaction solution was stirred for five hours at room temperature in the dark and thereafter stirred overnight at 3-8° C. in a cold room in the dark, thereby resulting in a conjugate solution. The reaction was quenched with Tris buffer. The conjugate solution was characterized.

Lane 1 in FIG. 1 shows the SDS-PAGE analysis of this conjugate solution.

Figure 3:
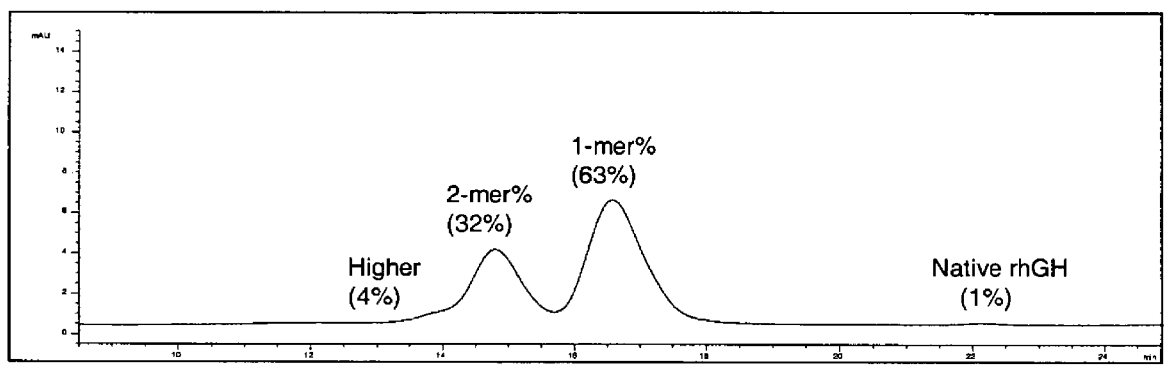
FIG. 3 is a reproduction of the SEC-HPLC chromatogram of an exemplary conjugate solution prepared by reacting hGH with mPEG2-ButyrALD, as described in greater detail in Example 27.

The aldehyde group of mPEG2-ButyrALD can react with the primary amines associated with hGH and covalently bond to them via a secondary amine upon reduction by a reducing reagent such as sodium cyanoborohydride. This is because the PEGylation reaction was carried out at pH 7.2 to 7.3, which favors internal lysine modification in conjunction with N-terminal modification. FIG. 3 shows the SEC-HPLC chromatogram of the conjugate solution. The PEGylation reaction yielded 63% 1-mer (one PEG attached to hGH or monoPEGylated), mono(mPEG-2-ButyrALD-40k) hGH, and 32% 2-mer (two PEGs attached to hGH or diPEGylated), di(mPEG-2-ButyrALD-40k) hGH. An anion-exchange chromatography method using Q Sepharose Fast Flow and Tris buffer was also developed to purify the conjugates. The profile of the purified conjugates was similar to that shown in FIG. 2B. The purified conjugates were up to 100% pure.

Using this same approach, other conjugates can be prepared using mPEG2-BuryrALD having other weight average molecular weights.

Example 28

In Vitro Activity of Exemplary (hGH)-PEG Conjugates

The in vitro activities of the (hGH)-PEG conjugates described in preceding Examples 26 and 27 are determined using one or more standard assays for assessing biological activity in vitro. Standard assays that may be employed include cell proliferation assays using, e.g., FDC-P1 cells (see, e.g., Clark et al., *Journal of Biological Chemistry*, 271: 21969-21977, 1996), or Ba/F3-hGHR cells, which express receptors for hGH, hGH delta 135-146, or Nb2 rat lymphoma cells, which proliferate in response to hGH via the lactogenic receptors (see, e.g., Alam, K. S., et al., *J. Biotech* 2000, Feb. 28, 78(1), 49-59). Receptor binding assays (see, e.g., U.S. Pat. No. 5,057,417), and hypophysectomized rat growth (Clark, et al., *Journal of Biological Chemistry, ibid*) may also be used.

All of the hGH conjugates described above are believed to be bioactive.

Example 29

Additional Characterization of Exemplary (hGH)-PEG Conjugates

Additional physiochemical analyses were conducted on the conjugates described in the preceding examples.

The table below provides a cross-reference for each of the conjugates analyzed and the corresponding Example in which its preparation and purification is described.

TABLE 1

Cross-Reference Information for Exemplary hGH Conjugates

| Conjugate Designation | Sample Abbreviation | Example Cross Reference | Description |
|---|---|---|---|
| mono(mPEG-2-NHS-40k) hGH | 1M | Example 26 | purified monomer |
| di(mPEG-2-NHS-40k) hGH | 1D | Example 26 | purified dimer |
| mono(mPEG-2-ButyrALD-40k) hGH | 4M | Example 27 | purified monomer |
| di(mPEG-2-ButyrALD-40k) hGH | 4D | Example 27 | purified dimer |

A. Protein Content

The hGH content of PEGylated and control samples was determined by several methods including the Bradford method (Bradford, M M. *Analytical Biochemistry* 72: 248-254. 1976), UV analysis at a wavelength of 280 nm in microtiter-plate format (5-point calibration), and by size exclusion chromatography with subsequent UV detection (280, 214 nm). The results confirmed covalent attachment of PEG; protein content for all samples was found to be in good agreement across the various methods employed.

B. SDS-PAGE Analysis

SDS-PAGE analysis, conducted under reducing conditions using both PEG stain and silver stain, was conducted on the purified conjugates described in Table 1 above. The observations based on the SDS-PAGE results were as follows:

For samples 1M and 1D: the analysis demonstrated that hGH was successfully PEGylated. The purified monomer, 1M, contained a small amount of dimer, while the purified dimer, 1D, contained a small amount of monomer and higher molecular weight PEGylated species (high-mers).

For samples 4M and 4D: the analysis demonstrated that hGH was successfully PEGylated. The purified monomer, 4M, contained a small amount of dimer. The purified dimer, 4D, contained a small amount of monomer and trimer, and traces of higher molecular weight PEGylated products (high-mers).

C. Size Exclusion Chromatography

Size exclusion chromatography of the PEG conjugates provides information on purity, size distribution, and content. Although baseline separation of the main component and reaction by-products (mono-, di-, tri- PEGylated species, etc.) was not achieved under the conditions employed, qualitative information regarding size distribution in relation to unmodified hGH and estimates regarding purity were obtained.

For samples 1M and 1D: The purified monomer, 1M, showed a well-separated by-product of higher molecular weight, interpreted to be dimer. The purified dimer, 1D, exhibited a significant tailing, which most likely reflects the presence of monomer and/or a broader molecular weight distribution of the PEG-moiety.

For samples 4M and 4D: The purified monomer, 4M, showed a well-separated by-product of higher molecular weight, interpreted as the dimer. The purified dimer, 4D, showed a moderately separated by-product of lower molecular weight, interpreted as the monomer.

Generally, the purity of the purified conjugate samples appeared higher in the monomer samples than in the dimer samples. A summary of calculated purity assessments based on SEC and UV-detection (214 nm) is provided in Table 2.

TABLE 2

Purity of Various hGH Conjugates

| Sample Description | Calculated Purity, % | Number of Impurities, >0.1% |
|---|---|---|
| 1M | 94.1 | 4 |
| 1D | 99.5 | 2 |
| 4M | 94.5 | 2 |
| 4D | 84.3 | 2 |

In general, with the exception of sample 4D, the purity of of the conjugates in all cases was about 90% or higher, and in some cases, was about 95% or higher, with the respect to type of conjugate (e.g., monoPEGylated—i.e., having only one PEG moiety attached to hGH, diPEGylated—having two PEG moieties attached to hGH, etc.).

Example 30

Biological Evaluations of Exemplary (hGH)-PEG Conjugates

A. In Vitro Assay

The biological activity of hGH and the conjugates described in Table 1 was assessed in vitro using an NB2-11 rat lymphoma cell proliferation assay. Briefly, NB2-11 cells derived from a rat lymphoma were incubated with hGH, which leads to binding of the hGH molecule to its receptor on the cell surface. Receptor binding induces the signal transduction cascade, which results in proliferation of the cells. Assay results were based on determined protein content, and a 100% bioactivity of unmodified hGH. A summary of results is provided in Table 3.

TABLE 3

In vitro Activity of Exemplary hGH Conjugates

| Sample Description | Activity, % | Number of Assays |
|---|---|---|
| 1M | 3.6 | 2 |
| 1D | 0.4 | 1 |
| 4M | 2.5 | 2 |
| 4D | 0.2 | 1 |

In general, these preliminary results suggest that the dimers (di-PEGylated species) exhibited an approximate 7-fold decrease in in vitro activity compared to the corresponding monomers, while conjugates prepared using higher molecular weight PEGs (e.g., 40 kD versus 30 kD) exhibited an approximate 5-fold reduction in in vitro activity relative to conjugates prepared using the lower molecular weight PEGs.

B. In vivo Assay

Conjugates 1M and 1D were further evaluated in a preliminary in vivo bioassay (hypophysectomized rat, USP monograph for Somatotropin®). Six groups of each of five animals received either hGH, 1M, 1D, or placebo in different dosing regimes. Weight gain as a pharmacodynamic output was measured on day 1, 3, 6, and 8. Additional details are provided in Table 7 below.

TABLE 4

In vivo Study Details

| Study Group | Sample | Application | Dose | Cumulative Dose |
|---|---|---|---|---|
| Std daily | hGH Standard | daily | 5 µg | 35 µg |
| Placebo daily | placebo | daily | 0 µg | 0 µg |
| Std bolus | hGH Standard | single dose day 1 | 110 µg | 110 µg |
| Placebo bolus | placebo | single dose day 1 | 0 µg | 0 µg |
| 1M bolus | 1M | single dose day 1 | 110 µg | 110 µg |
| 1D bolus | 1D | single dose day 1 | 110 µg | 110 µg |

Figure 4:
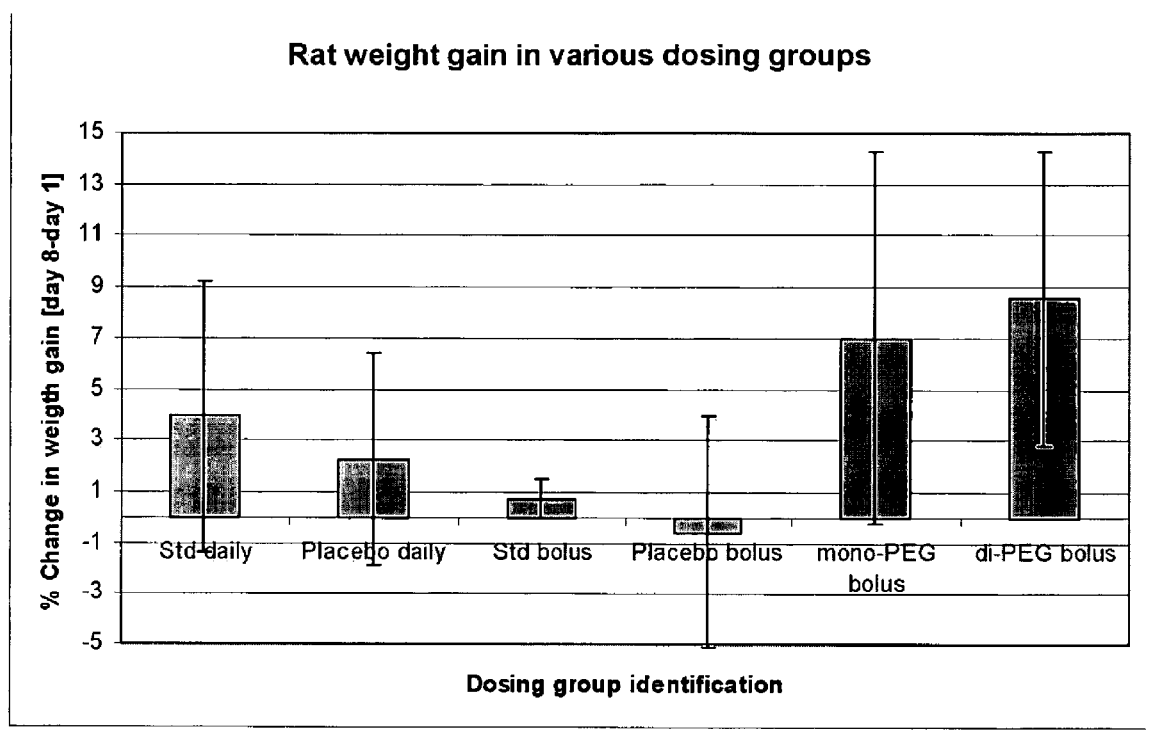
FIG. 4 is a plot demonstrating weight gain in rats following day 8 for six different groups dosed with either hGH, mono (mPEG-2-NHS-40k) hGH, di(mPEG-2-NHS-40k) hGH, or placebo, in different dosing regimes as described in Example 30.

The results of the experiment are summarized in FIG. 4 (weight gain following day 8) and FIG. 5 (weight gain over time course of study). Data in FIG. 4 are given as mean±standard deviation, where n=5, except for the di-PEGylated sample, 1D, where n=4, due to the death of one animal. Placebo and a single high dose of hGH resulted in no or moderate weight gain during the eight days. Daily dosing of 5 µg of the hGH standard induced an overall weight gain of 4% on day 8, whereas the single high dose of 110 µg of 1M and 1D produced an increase of weight of 7% and 9% respectively (FIG. 4). Comparing the time course of weight gain, it appears that the PEGylated hGH conjugates evoke a similar but superior response in the hypophysectomized rat (FIG. 5).

Although the preliminary in vitro results suggest that increasing the amount of PEG attached to hGH reduces its ability to stimulate the hGH receptor, based on the preliminary in vivo results, it appears that a reduction in bioactivity is more than balanced by increased half-life and/or plasma availability, thus leading to a conclusion that the conjugates provided herein possess a superior pharmacodynamic effect in vivo when compared to unmodified hGH at an identical dosing regimen.

What is claimed is:

1. A conjugate of the following structure:

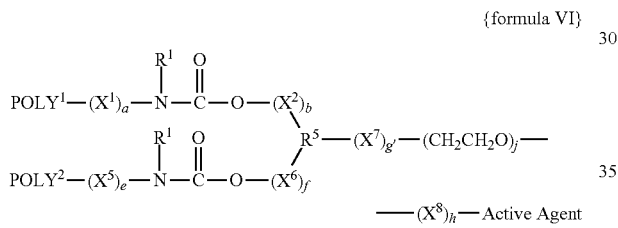

{formula VI} wherein:

POLY$^1$ is a water-soluble polymer selected from the group consisting of poly(alkylene glycols), poly(vinyl pyrrolidone), poly(vinyl alcohol), polyoxazoline and poly(N-acryloylmorpholine);

POLY$^2$ is a water-soluble polymer selected from the group consisting of poly(alkylene glycols), poly(vinyl pyrrolidone), poly(vinyl alcohol), polyoxazoline and poly(N-acryloylmorpholine);

(a) is 0, 1, 2 or 3;
(b) is 0, 1, 2 or 3;
(e) is 0, 1, 2 or 3;
($f^1$) is 0, 1, 2 or 3;
($g^1$) is 0, 1, 2 or 3;
(h) is 0, 1, 2 or 3;
(j) is 0, 1, 2 or 3;

Each R$^l$ is independently H or an organic radical selected from the group consisting of alkyl, substituted alkyl, alkenyl, substituted alkenyl, alkynyl, substituted alkynyl, aryl and substituted aryl;

X$^1$, when present, is a first spacer moiety;
X$^2$, when present, is a second spacer moiety;
X$^5$, when present, is a fifth spacer moiety;
X$^6$, when present, is a sixth spacer moiety;
X$^7$, when present, is a seven spacer moiety;
X$^8$, when present, is an eight spacer moiety;

R$^1$ is a branching moiety selected from the group consisting of

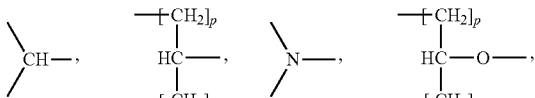

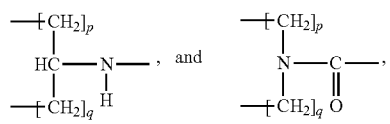

wherein (p) is 1-10 and (q) is 1-10; and

Active Agent is a residue of a pharmacologically active agent.

2. The conjugate of claim 1, wherein each R$^1$ is H.

3. The conjugate of claim 1, wherein each water-soluble polymer is a poly(alkylene glycol).

4. The conjugate of claim 3, wherein each poly(alkylene glycol) is a poly(ethylene glycol).

5. The conjugate of claim 4, wherein each poly(ethylene glycol) is terminally capped with methoxy.

6. The conjugate of claim 4, wherein each poly(ethylene glycol) has a molecular weight of from about 100 Daltons to about 100,000 Daltons.

7. The conjugate of claim 6, wherein each poly(ethylene glycol) has a molecular weight of from about 1,000 Daltons to about 60,000 Daltons.

8. The conjugate of claim 7, wherein each poly(ethylene glycol) has a molecular weight of from about 2,000 Daltons to about 50,000 Daltons.

9. The conjugate of claim 1, has the following structure:

[Chemical structure: H₃CO—(CH₂CH₂O)ₙ—CH₂CH₂—NH—C(=O)—O— and H₃CO—(CH₂CH₂O)ₙ—CH₂CH₂—NH—C(=O)—O— both connected to —O—(X⁷)_{g'}—(CH₂CH₂O)_j—(X⁸)_h—Active Agent]

when the branching moiety R⁵ is:

[Structure: —[CH₂]_p / HC—O— / —[CH₂]_q]

and,

[Chemical structure similar to above with —O—(X⁷)_{g'}—(CH₂CH₂O)_j—[CR²R³]_c—NH₂—Active Agent]

wherein:
(m) is 2 to 4000;
(g¹) is 0, 1, 2 or 3;
(h) is 0, 1, 2 or 3;
(j) is 0 to 20;
(p) is 1;
(q) is 1; and
Active Agent is a residue of a pharmacologically active agent.

10. The conjugate of claim 9, of the following structure:

[Chemical structure with —O—(X⁷)_{g'}—(CH₂CH₂O)_j—[CR²R³]_c—C(=O)—NH—Active Agent]

(m) is 2 to 4000;
(g¹) is 0, 1, 2 or 3;
(c) is 1 to 10;
each R² is H or an organic radical selected from the group consisting of alkyl, substituted alkyl, alkenyl, substituted alkenyl, alkynyl, substituted alkynyl, aryl and substituted aryl;
each R³ is H or an organic radical selected from the group consisting of alkyl, substituted alkyl, alkenyl, substituted alkenyl, alkynyl, substituted alkynyl, aryl and substituted aryl;
(j) is 0 to 20; and Active Agent is a residue of a pharmacologically active agent.

11. The conjugate of claim 9, wherein the pharmacologically active agent is selected from the group consisting of erythropoietin, granulocyte colony stimulating factor, interferon-α, human growth hormone, interferon-β, follicle stimulating hormone, Factor VIII, B-domain deleted Factor VIII, desmopressin and amdoxivir.

12. The conjugate of claim 9, of the following structure:

[Chemical structure with —O—(X⁷)_{g'}—(CH₂CH₂O)_j—[CR²R³]_c—NH₂—Active Agent]

wherein:
(m) is 2 to 4000;
(g¹) is 0, 1, 2 or 3;
(c) is 1 to 10;
each R² is H or an organic radical selected from the group consisting of alkyl, substituted alkyl, alkenyl, substituted alkenyl, alkynyl, substituted alkynyl, aryl and substituted aryl;
each R³ is H or an organic radical selected from the group consisting of alkyl, substituted alkyl, alkenyl, substituted alkenyl, alkynyl, substituted alkynyl, aryl and substituted aryl;
(j) is 0 to 20; and
Active Agent is a residue of a pharmacologically active agent.

13. The conjugate of claim 12, wherein the pharmacologically active agent is selected from the group consisting of erythropoietin, granulocyte colony stimulating factor, interferon-α, human growth hormone, interferon-β, follicle stimulating hormone, Factor VIII, B-domain deleted Factor VIII, desmopressin and amdoxivir.

14. The conjugate of claim 9, of the following structure:

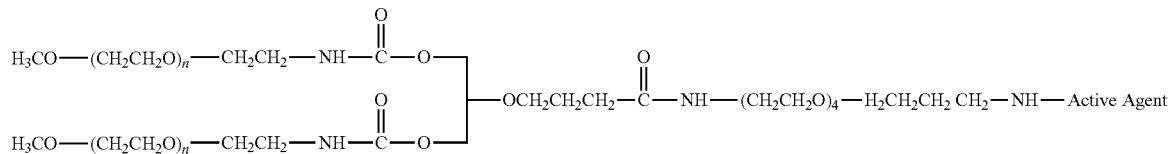

wherein:
(m) is 2 to 4000; and
Active Agent is a residue of a pharmacologically active agent.

15. The conjugate of claim 14, wherein the pharmacologically active agent is selected from the group consisting of human growth hormone.

16. The conjugate of claim 1, wherein the pharmacologically active agent is selected from the group consisting of erythropoietin, granulocyte-colony stimulating factor, interferon-α, human growth hormone, interferon-β, follicle stimulating hormone, Factor VIII, B-domain deleted Factor VIII, desmopressin and amdoxivir.

17. The conjugate of claim 1, wherein each $R^1$ is H.

18. The conjugate of claim 1, wherein each $R^1$ is an organic radical and is selected from the group consisting of alkyl, substituted alkyl, alkenyl, substituted alkenyl, alkynyl substituted alkynyl, aryl and substituted aryl.

* * * * *